United States Patent [19]
Gee et al.

[11] Patent Number: 6,162,931
[45] Date of Patent: *Dec. 19, 2000

[54] FLUORINATED XANTHENE DERIVATIVES

[75] Inventors: Kyle R. Gee, Springfield; Martin Poot, Eugene; Dieter H. Klaubert, Eugene; Wei-Chuan Sun, Eugene; Richard P. Haugland, Eugene; Fei Mao, Eugene, all of Oreg.

[73] Assignee: Molecular Probes, Inc., Eugene, Oreg.

[ * ] Notice: This patent is subject to a terminal disclaimer.

[21] Appl. No.: 08/631,202

[22] Filed: Apr. 12, 1996

[51] Int. Cl.[7] .................. C07D 311/82; C07D 311/78; C07D 311/88; C07D 471/00

[52] U.S. Cl. .................. 549/223; 435/6; 430/345; 430/915; 430/925; 568/700; 568/707; 544/150; 546/41; 549/224; 549/225; 549/226; 549/227

[58] Field of Search .................. 435/6; 568/700, 568/707; 430/345, 915, 925; 544/150; 546/41; 549/223, 224, 225, 226, 227

[56] References Cited

U.S. PATENT DOCUMENTS

| | | | |
|---|---|---|---|
| 3,996,345 | 12/1976 | Ullman et al. | 424/12 |
| 4,199,559 | 4/1980 | Ullman et al. | 424/8 |
| 4,213,904 | 7/1980 | Haugland et al. | 260/326.5 |
| 4,318,846 | 3/1982 | Khanna et al. | 260/112 B |
| 4,420,568 | 12/1983 | Wang et al. | 436/536 |
| 4,439,356 | 3/1984 | Khanna et al. | 260/112 R |
| 4,510,251 | 4/1985 | Kirkemo et al. | 436/536 |
| 4,609,740 | 9/1986 | Rotman | 549/223 |
| 4,711,955 | 12/1987 | Ward et al. | 536/29 |
| 4,997,928 | 3/1991 | Hobbs | 536/27 |
| 5,047,519 | 9/1991 | Hobbs, Jr. et al. | 536/23 |
| 5,049,673 | 9/1991 | Tsien et al. | 546/107 |
| 5,171,534 | 12/1992 | Smith et al. | 422/82.05 |
| 5,208,148 | 5/1993 | Haugland et al. | 435/14 |
| 5,227,487 | 7/1993 | Haugland et al. | 546/15 |
| 5,332,666 | 7/1994 | Prober et al. | 435/91.5 |
| 5,352,803 | 10/1994 | Mattingly | 549/220 |
| 5,362,628 | 11/1994 | Haugland et al. | 435/18 |
| 5,401,847 | 3/1995 | Glazer et al. | 546/107 |
| 5,405,975 | 4/1995 | Kuhn et al. | 549/347 |
| 5,442,045 | 8/1995 | Haugland et al. | 530/391.3 |
| 5,451,343 | 9/1995 | Neckers et al. | 252/582 |
| 5,453,517 | 9/1995 | Kuhn et al. | 549/227 |
| 5,459,268 | 10/1995 | Haugland et al. | 546/37 |

FOREIGN PATENT DOCUMENTS

WO 94/05688  3/1994  WIPO.
WO 97/36960  10/1997  WIPO.

OTHER PUBLICATIONS

Rink, et al., J. Cell Biol. 95, 189 (1982).
Haugland, et al., Molecular Probes Handbook of Fluorescent Probes and Research Chemicals (1992).
Wittung, et al., Nature 368, 561 (1994).
Raju, et al., Am. J. Physiol. 256, C540 (1989).
Brinkley, et al., Bioconjugate Chem. 3, 2 (1992).
Durrani, et al., J. Chem. Soc. Perkin Trans. I, 1658 (1980).
Patrick, et al., J. Org. Chem. 51, 3242 (1986).
Lerman, et al., J. Org. Chem. 49, 806 (1984).
Gee, et al., Synthetic Communications, 23(3), 357 (1993).
Emmons, et al., J. Am. Chem. Soc., 79, 5528 (1957).
Gilbert, et al., J. Org. Chem., 44, 659 (1979).
Bagal, et al., J. Org. Chem. USSR, 5, 1767 (1969).
Tsien, et al., Meth. Enzym. 172, 230 (1989).
Amlaiky, et al., FEBS Lett, 176, 436 (1984).
Kendall, et al., J. Biol. Chem. 257, 13892 (1982).
Szoka, Jr., et al., Proc. Natl. Acad. Sci. USA 75, 4194 (1978).
Szoka, Jr., et al., Ann. Rev. Biophys. Bioeng. 9, 467 (1980).

*Primary Examiner*—Jezia Riley
*Attorney, Agent, or Firm*—Anton E. Skaugset; Allegra J. Helfenstein

[57] ABSTRACT

The family of dyes of the invention are fluoresceins and rhodols that are directly substituted on one or more aromatic carbons by fluorine. These fluorine-substituted fluorescent dyes possess greater photostability and have lower sensitivity to pH changes in the physiological range of 6–8 than do non-fluorinated dyes, exhibit less quenching when conjugated to a substance, and possess additional advantages. The dyes of the invention are useful as detectable tracers and for preparing conjugates of organic and inorganic substances.

107 Claims, 5 Drawing Sheets

FLUORINATED XANTHENE DERIVATIVES

FIELD OF THE INVENTION

The invention relates to novel fluorinated xanthene dyes (including fluorescein and rhodol dyes), reactive dye derivatives, dye-conjugates and dyes that are enzyme substrates; as well as to the use of the fluorinated xanthenes. Additionally a facile synthesis for fluorinated resorcinols and aminophenols is provided.

BACKGROUND OF THE INVENTION

Fluorescent dyes are known to be particularly suitable for biological applications in which a highly sensitive detection reagent is desirable. Fluorescent dyes are used to impart both visible color and fluorescence to other materials.

The dyes of this invention are fluorine-substituted analogs of xanthene-based dyes that are typically fluorescein or rhodol derivatives. Fluoresceins and rhodols are known to strongly absorb visible light and, in most cases, to be highly fluorescent. Polychlorinated, polybrominated and polyiodinated analogs of fluorescein dyes are known to shift the spectrum to longer-wavelengths than the unsubstituted dyes. Polybrominated and polyiodinated analogs of fluorescein dyes have much lower fluorescence yields, higher phosphorescence yields and are effective photosensitizers of certain chemical reactions. The preparation and use of reactive rhodol dyes and their conjugates was disclosed in U.S. Pat. Nos. 5,227,487 (1993) and 5,442,045 (1995) to Haugland et al. (each incorporated by reference). Both fluorescein and rhodol are considered "xanthene" dyes. That is, they are characterized by structural similarity to, or derivation from, xanthene.

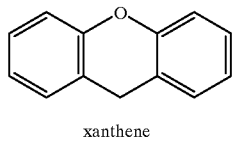

xanthene

"Fluorescein" dyes include derivatives of 3H-xanthen-6-ol-3-one that are substituted at the 9-position by a 2-carboxyphenyl group, while "rhodol dyes" include derivatives of 6-amino-3H-xanthen-3-one that are substituted at the 9-position by a 2-carboxyphenyl group.

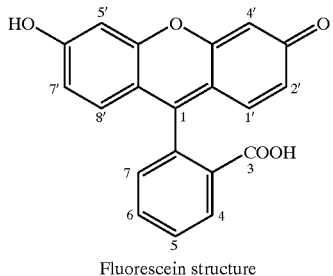

Fluorescein structure

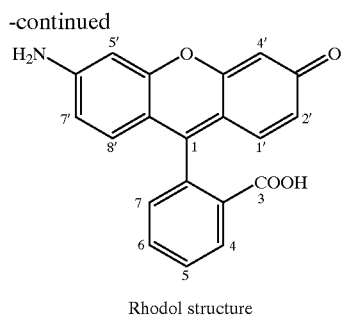

Rhodol structure

When substituted at the 1-position by a derivative capable of forming a 5- or 6-membered lactone or lactam ring alternative structures for fluorescein and rhodol dyes are possible:

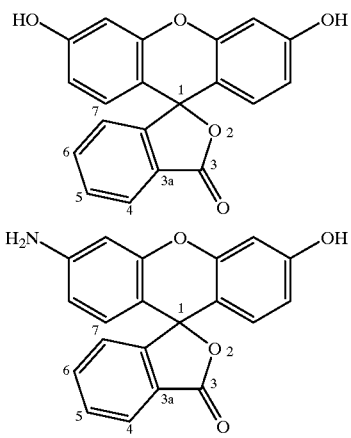

Despite their widespread use in biological assays, fluorescein-based dyes have certain well-known deficiencies. In particular, it is widely recognized that fluorescein conjugates are unstable with respect to the intense illumination produced in most fluorescence instrumentation. The result is irreversible photobleaching, which typically results in a rapid decrease in fluorescent signal. In a fluorescence microscope the amount of irreversible bleaching may reach essentially 100% in less than one minute. This susceptibility to photobleaching considerably reduces the utility of fluorescein fluorophores for quantitative assays. A second problem of fluorescein is that its $pK_a$ (acid dissociation constant) is approximately 6.4 in water (see FIG. 3), making its absorbance and fluorescence properties quite pH dependent in the physiological pH range, so much so that certain fluoresceins are utilized as fluorescent pH indicators (for example BCECF, Rink et al. J. CELL BIOL. 95, 189 (1982)). This pH sensitivity also reduces the utility of fluoresceins for quantitative assays (See FIG. 3). A third difficulty that is recognized when using fluorescein dyes is the tendency of fluorescein conjugates to exhibit fluorescence that is highly quenched relative to that of the free fluorophore. This typically quickly leads to protein conjugates of fluorescein exhibiting less fluorescence even when more dye molecules are conjugated to the protein (see FIG. 1), reducing the sensitivity that is possible for assays using fluorescein conjugates. A highly desirable class of fluorophores would retain the favorable characteristics of fluorescein, including generally high absorbance and fluorescence of fluorescein, the ability to be excited using the 488-nm line of the argon-ion laser, and the ability to use standard optical filters for fluorescein that are already available for most fluorescence microscopes, while simultaneously possessing characteristics that improve on the deficiencies of fluorescein.

Fluorination of fluorescein-like dyes simultaneously improves all three of these known deficiencies of fluorescein dyes, while generally retaining the other desirable spectral properties of fluorescein-like dyes. In particular, fluorinated analogs of fluorescein are typically more photostable than the corresponding nonfluorinated analogs. In addition, the conjugates of fluorinated fluorescein dyes typically exhibit higher fluorescence than those of nonfluorinated dyes. In some cases the fluorescence of the protein conjugates of the fluorinated dyes is not quenched at degrees of substitution that strongly quench the fluorescence of conjugates of the corresponding nonfluorinated dyes (for example, see FIG. 1). The $pK_a$ of the fluorinated dyes is significantly lower than that of the nonfluorinated analogs (>1.5 pH units on the otherwise unsubstituted dyes, see FIG. 3). Furthermore, we found that fluorination of fluoresceins at the 2'- and 7'-positions unexpectedly had virtually no effect on either the absorption spectrum, the fluorescence spectrum or the quantum yield of the dye relative to the nonfluorinated versions, and additionally, the conjugates of these fluorinated fluoresceins tend to be more fluorescent than the nonfluorinated versions (for example, see FIG. 1) making these dyes preferred substitutes for fluoresceins. All other reported substitutions at the 2'- and 7'-positions of fluorescein, including halogenation with Cl, Br or I, have been reported to shift the spectra of the dye toward longer wavelengths.

Additionally, fluorescein analogs that are polyfluorinated on the phenyl substituent that is typically present in most fluorescein and rhodol dyes are subject to nucleophilic displacement reactions, providing a novel route to reactive derivatives and conjugates. Certain types of the fluorinated xanthenes unexpectedly give products that are well-retained in live biological cells. This reactivity is not observed with the nonfluorinated xanthenes.

In addition to the fluorinated dyes of the invention, we hereby also provided a means to prepare derivatives of fluorescein that are substituted at the 1'- and/or 8'-positions; molecules that do not appear to have been previously described.

Analogs of fluorescein dyes with fluorine atoms substituted onto the xanthene portion of the dye have been generically included as claimed embodiments in various patents describe, typically by claiming "halogens" as permitted substituents on the dye. However these patents do not describe either the highly advantageous properties of these fluorinated fluorophores and their conjugates, and typically require other structural limitations not required by the present invention. In particular these patents do not describe the lack of spectral shift and enhanced photostability that typifies several of the dyes of the current invention. Also, these patents do not require that the dye be substituted by at least one fluorine atom. Furthermore, these patents fail to describe methods that are suitable for synthesis of the dyes the invention, as the unique chemistry of fluorine in organic chemistry does not permit utilization of the methods that are typically used to prepare chlorine, bromine or iodine substituted fluorescein derivatives. While halogenated rhodol dyes have been described previously (U.S. Pat. Nos. 5,227,487 (1993) and 5,442,045 (1995) to Haugland et al., the properties and syntheses of fluorinated analogs of rhodol dyes have not previously been described. In particular, efficient methods for preparing the requisite fluororesorcinols and fluoroaminophenols have not previously been described. It was found that a more facile method of preparing these intermediates was required in order to efficiently prepare the wide variety of dyes described herein.

The preparation and use of fluorescein dyes and conjugates of fluorescein dyes is already well-known in the art, as described in U.S. Pat. No. 4,213,904 to Haugland et al. (1980), U.S. Pat. No. 3,996,345 to Ullman et al. (1976), U.S. Pat. No. 4,199,559 to Ullman et al. (1980)), U.S. Pat. No. 5,352,803 to Mattingly (1993), U.S. Pat. No. 4,420,568 to Wang et al. (1983), U.S. Pat. No. 5,332,666 to Prober et al. (1994), U.S. Pat. No. 4,997,928 to Hobbs (1991), U.S. Pat. No. 4,439,356 to Khanna et al. (1984), U.S. Pat. No. 4,510,251 to Kirkemo et al. (1985), U.S. Pat. No. 4,609,740 to Rotman (1986), U.S. Pat. No. 4,318,846 to Khanna et al. (1982), and U.S. Pat. No. 5,451,343 to Neckers et al. (1995), all of which are incorporated by reference, and International Publication No. WO 94/05688 by Menchen et al. (1994).

We have demonstrated the use of the fluorinated dyes for the preparation of a wide variety of reactive derivatives that utilize chemistry mostly analogous to that used to prepare known reactive fluorescein and rhodol dyes. We have also demonstrated a heretofor unknown reactivity toward nucleophilic displacement possessed by fluorinated dye derivatives that are fluorinated on the 9-aryl portion of the dyes. We have further demonstrated that the improved properties of the fluorinated dyes are retained in their conjugates and that these conjugates have properties that are typically superior to those prepared from the corresponding nonfluorinated dyes. The dyes of the invention are suitable for substitution for fluoresceins and rhodols in all their known applications except those requiring sensitivity to pH changes near pH 7.

For the practical preparation of the fluorinated dyes it was necessary to develop a novel general synthesis of fluorinated resorcinol and aminophenol derivatives that would yield isomer-free products in good yield. Previous methods give low yields of products that usually consist of difficult-to-separate isomer mixtures and require the use of generally obnoxious fluorinating agents. Our novel method uses generally available precursors and standard laboratory reagents and equipment to reproducibly produce these essential precursors in relatively large quantities.

It is an object of this invention to provide novel and advantageous fluorinated fluorescein and rhodol dyes suitable for use as tracers, labels or synthetic intermediates. It is an additional object of this invention to provide reactive derivatives of fluorinated fluorescein and rhodol dyes useful for the preparation of fluorescent dye-conjugates. It is yet another object of this invention to provide usefully labeled dye-conjugates of fluorinated fluorescein and rhodol dyes that possess the novel and advantageous properties of the novel dyes. It is a further object of the invention to provide versions of fluorinated fluorophores that are useful for detecting enzymes, particularly within live cells and cellular organelles. It is also an object of the invention to provide a novel synthesis of fluorinated resorcinols and aminophenols, greatly simplifying the preparation of the fluorinated fluorescein and rhodol dyes of the invention.

Figure 2:
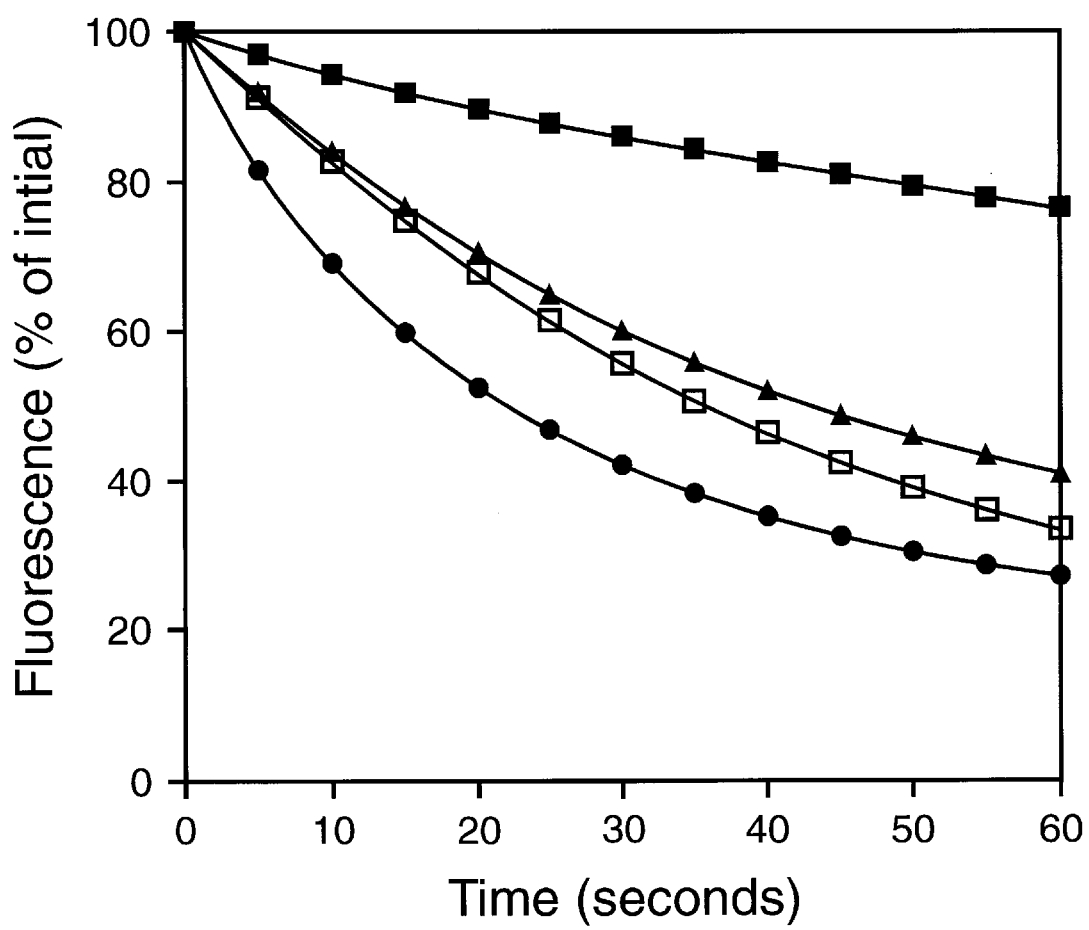

FIG. 2: A comparison of photostability of green immunofluorescent staining dyes, as described in Example 124. Goat anti-mouse IgG conjugates of fluorinated dyes exhibit enhanced photostability relative to non-fluorinated dyes: 6-carboxymethylthio-2',4,5,7,7'-pentafluorofluorescein (Compound 59) (■), 9-(4-carboxy-2-sulfophenyl)-2',7'-difluoro-6-hydroxy-3H-xanthen-3-ol-6-one (▲), 6-carboxy-2',7'-difluorofluorescein (□) or 6-carboxyfluorescein (●).

Figure 3:
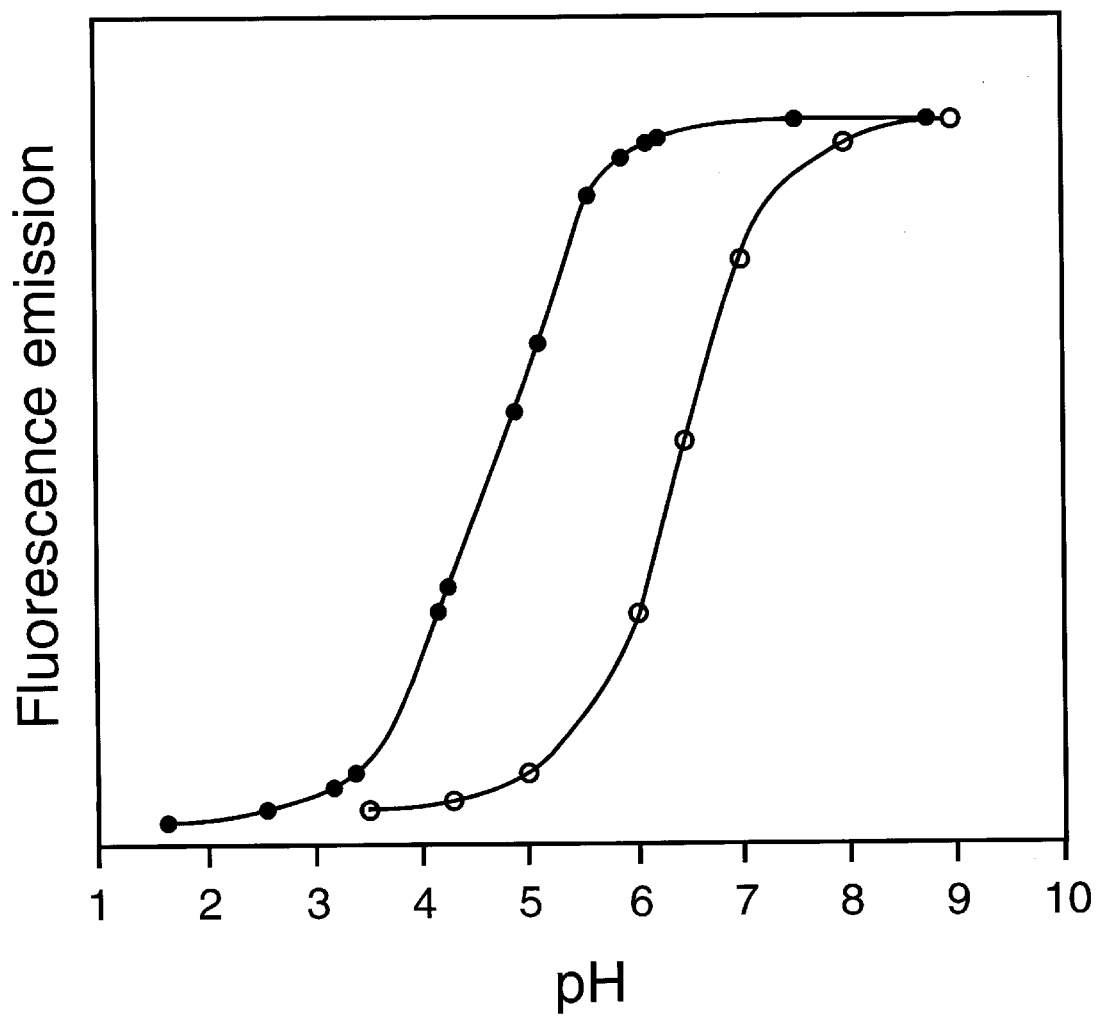

FIG. 3: A comparison of pH-dependent fluorescence, as described in Example 136. Fluorescence intensities were measured for equal concentrations of 6-carboxy-2',7'-difluorofluorescein (●), and 6-carboxyfluorescein (○) using excitation/emission at 490/520 nm.

Figure 4:
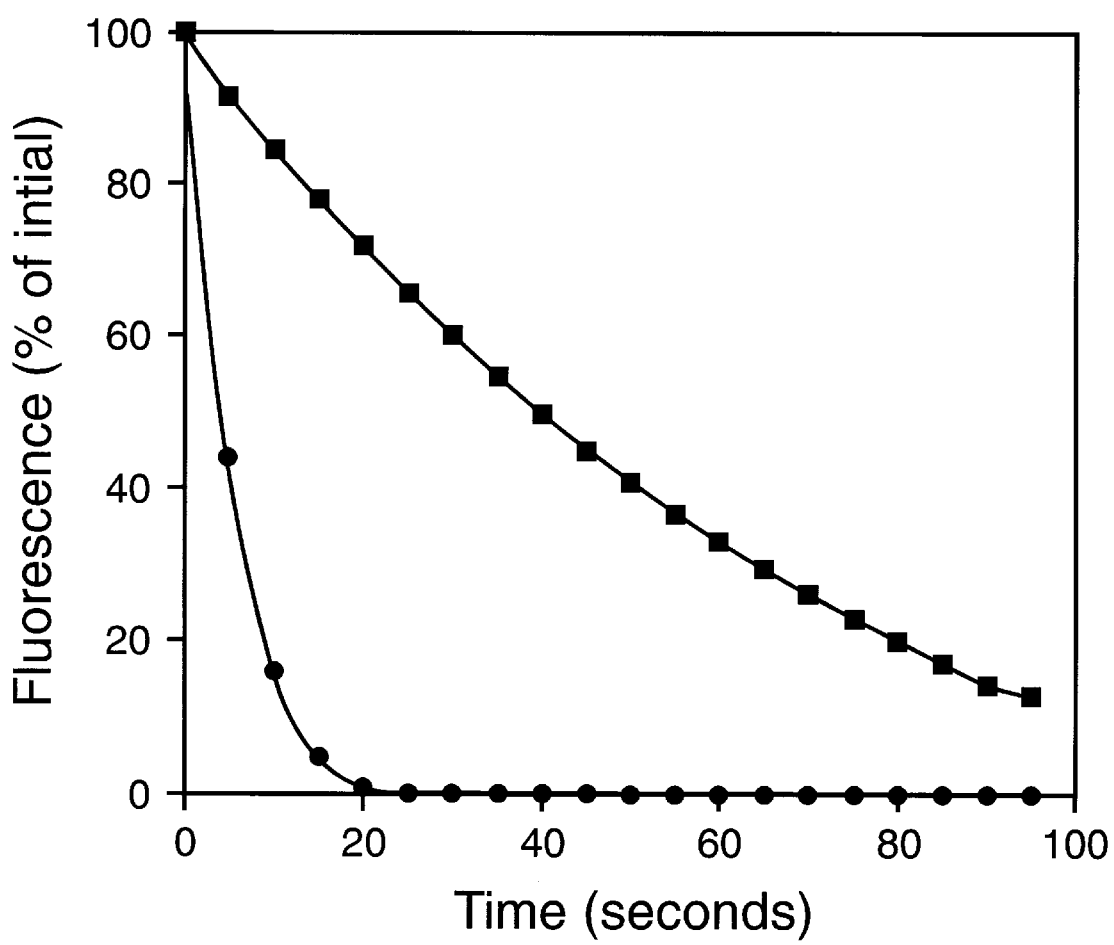

FIG. 4: A comparison of photostability of phalloidin conjugates of 6-carboxymethylthio-2',4,5,7,7'-pentafluorofluorescein (■) and 6-carboxyfluorescein (●). Samples were continuously illuminated and viewed as described in Example 116.

Figure 5:
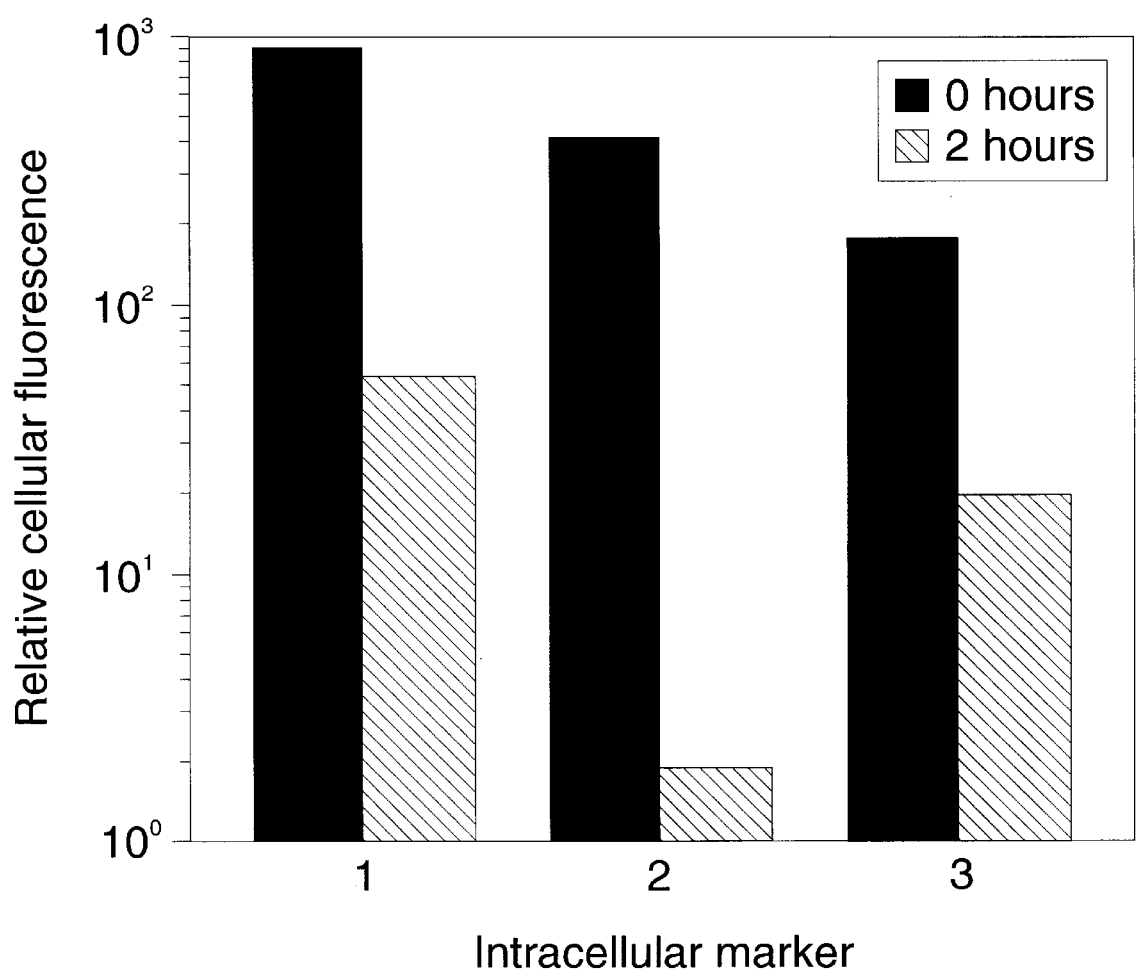

FIG. 5: A comparison of retained fluorescence in cells treated with 1) 4,5,6,7-tetrafluorofluorescein diacetate (TFFDA), 2) fluorescein diacetate (FDA) and 3) 2',4,5,6,7,7'-hexafluorofluorescein diacetate (HFFDA), as described in Example 132.

SUMMARY OF THE INVENTION AND DESCRIPTION OF PREFERRED EMBODIMENTS

The family of dyes of the invention are fluoresceins and rhodols that are directly substituted at one or more aromatic carbons by fluorine. These fluorine-substituted fluorescent dyes typically possess greater photostability and lower pH sensitivity than non-fluorinated dyes, exhibit less quenching when conjugated to a substance, and possess additional advantages.

As used herein, carboxy shall be taken to mean a carboxylic acid (—COOH), biologically compatible salt of a carboxylic acid, or a biologically compatible ester of a carboxylic acid. As used herein, sulfo shall be taken to mean a sulfonic acid (—$SO_3H$), or a biologically compatible salt of a sulfonic acid. A biologically compatible salt means a non-toxic salt of carboxylic acid that is stable and synthetically accessible, and that is not deleterious to biological systems. Examples of biologically compatible salts include $K^+$, $Na^+$, $Cs^+$, $Li^+$, $Ca^{2+}$, $Mg^{2+}$, $NR_4^+$ salts, where R=H, $C_1$–$C_4$ alkyl, or $C_2$–$C_4$ alkanol or combinations thereof, or combinations of acid salts of these counterions plus free acid groups. A biologically compatible ester means a readily hydrolyzable esters as are known and used in biological systems, such as alpha-acyloxyalkyl esters, typically alpha-acyloxyalkyl esters (—$CH_2$—O—(C=O)—$R^{18}$, where $R^{18}$ is an alkyl having 1–4 carbons), especially acetoxymethyl ($CH_3CO_2CH_2$—) esters.

In one embodiment of the invention, the dyes have the formula

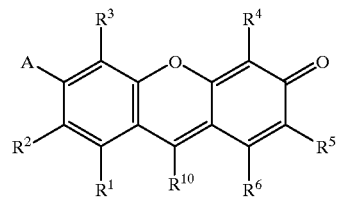

Formula I

The ring substituents $R^1$ and $R^6$ are independently H, F, Cl, Br, I, $C_1$–$C_{18}$ alkyl or $C_1$–$C_{18}$ alkoxy. Typically, $R^1$ and $R^6$ are H or F.

The ring substituents $R^2$, $R^3$, $R^4$ and $R^5$ are independently H, F, Cl, Br, I or CN. Additionally, any of $R^2$, $R^3$, $R^4$ and $R^5$ are optionally alkyl groups, alkoxy groups or alkylthio groups, each having 1–18 carbons. Where the dye substituent is an alkylalkoxy, or alkylthio that substituent is optionally further substituted by F, Cl, Br, I, carboxy, sulfo, amino, alkylamino, dialkylamino or alkoxy, the alkyl portions of each independently having 1–6 carbons. Additionally, dye substituents $R^3$ and $R^4$ are optionally each —$CH_2$—N—($CH_2COOR^{17}$), where $R^{17}$ is H, a biologically compatible counterion, a linear or branched alkyl having 1–6 carbons, or alpha-acyloxyalkyl ester (—$CH_2$—O—(C=O)—$R^{18}$, where $R^{18}$ is an alkyl having 1–4 carbons).

The substituent A, covalently attached by a formal single bond, is either $OR^7$ or the substituted amine $NR^8R^9$, where $R^7$ is H, $C_1$–$C_{18}$ alkyl or $C_1$–$C_{18}$ acyl, the alkyl portions of which independently have 1–6 carbons, and are optionally substituted by amino, hydroxy or carboxy, or $R^7$ is a trialkylsilyl moiety, the alkyl portions of which have 1–6 carbons. The amine substituents $R^8$ and $R^9$ are independently H, an alkyl having 1–6 carbons, or acyl having 1–18 carbons. Where one or both of $R^8$ and $R^9$ are alkyl or acyl, the alkyl portions are optionally further substituted by carboxy or sulfo. Additionally, $R^8$ when taken in combination with $R^2$, or $R^9$ when taken in combination with $R^3$, or both, form a saturated 5- or 6-membered ring that is optionally substituted by one or more methyls. Additionally and optionally, the amine substituents $R^8$ and $R^9$, when taken in combination, form a saturated 5- or 6-membered heterocycle that is a piperidine, a morpholine, a pyrrolidine or a piperazine that is optionally substituted by methyl, or carboxy.

The substituent $R^{10}$ is H, CN, F, carboxy, or an alkyl, alkenyl or alkynyl group having 1–18 carbons. Where $R^{10}$ is an alkyl, it is optionally substituted by F, Cl, Br, carboxy, sulfo, amino, alkylamino or dialkylamino where the alkyl portions of each substituent have 1–6 carbons. Alternatively, $R^{10}$ is a substituted aryl of the formula

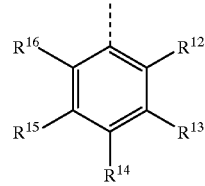

Where $R^{10}$ is a substituted aryl, it is sometimes referred to as the "bottom ring". Ring substituents $R^{12}$, $R^{13}$, $R^{14}$, $R^{15}$ and $R^{16}$ are independently H, F, Cl, Br, I, carboxy, sulfo, CN, nitro, hydroxy, azido, amino or hydrazino. Additionally, the ring substituents $R^{12}$, $R^{13}$, $R^{14}$, $R^{15}$ and $R^{16}$ are optionally $C_1$–$C_{18}$ alkyl, $C_1$–$C_{18}$ alkoxy, $C_1$–$C_{18}$ alkylthio, $C_1$–$C_{18}$ alkylamino, $C_1$–$C_{18}$ alkylester, $C_1$–$C_{18}$ alkylamido or $C_1$–$C_{18}$ arylamido, the alkyl or aryl portions of which are optionally substituted by F, Cl, Br, I, hydroxy, carboxy, sulfo, amino, alkylamino, dialkylamino or alkoxy, the alkyl portions of which have 1–6 carbons. Alternatively, any two adjacent substituents of $R^{13}$, $R^{14}$, $R^{15}$ and $R^{16}$, when taken in combination, form a fused 6-membered aromatic ring (making $R^{10}$ a naphthyl) that is optionally further substituted by carboxy.

In one embodiment of the invention, $R^{10}$ is a substituted aryl, preferably phenyl, $R^{12}$ is a carboxy, and $R^{13}$, $R^{14}$, $R^{15}$ and $R^{16}$ are independently H, F, or carboxy. In another embodiment of the invention, $R^{12}$ is a carboxy or a sulfo, and none of $R^{13}$, $R^{14}$, $R^{15}$ or $R^{16}$ is F. In yet another embodiment, three of $R^{13}$, $R^{14}$, $R^{15}$ and $R^{16}$ are F, and $R^{12}$ is a carboxy or a sulfo.

In another embodiment of the invention, the dyes have the formula

Formula II

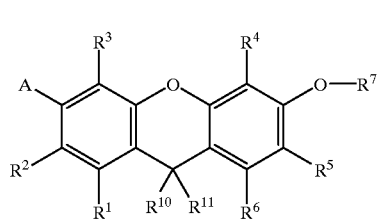

The ring substituents $R^1$, $R^2$, $R^3$, $R^4$, $R^5$ and $R^6$ are as defined previously.

Substituent A is independently $OR^7$ or $NR^8R^9$, where $R^7$, $R^8$ and $R^9$ are as defined previously.

$R^{10}$ is as defined previously. $R^{11}$ is H, hydroxy, CN or alkoxy having 1–6 carbons, or $R^{10}$ in combination with $R^{11}$ forms a 5-membered spirolactone ring, or $R^{11}$ in combination with $R^{12}$ forms a 5- or 6-membered spirolactone ring, or a 5- or 6-membered sultone ring. Spirolactone and spirosultone rings are depicted in the simplified formulas below (additional substituents are not shown). The methylene carbons of the spirolactone ring or spirosultone ring are optionally and independently substituted by H, F or $CH_3$.

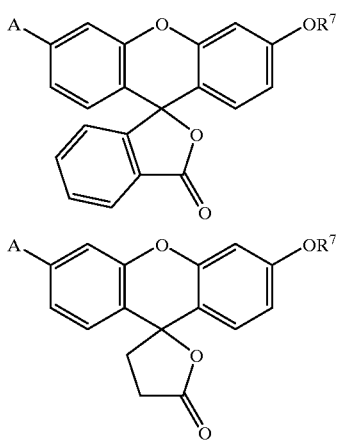

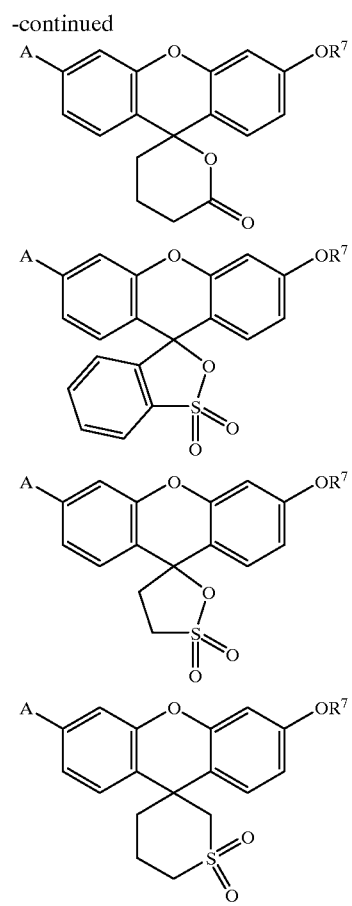

Alternatively, $R^{10}$ when taken in combination with $R^{11}$, is a carbonyl oxygen, according to the simplified formula below (additional substituents are not shown).

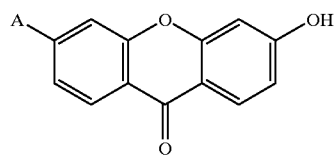

Dye embodiments that incorporate a spirolactone ring are representative of a structural isomer that may exist in equilibrium with the isomer wherein $R^{12}$ is a carboxylic acid, or $R^{10}$ is a propionic or butyric acid. Dyes that incorporate a spirosultone ring may exist in equilibrium with the isomer wherein $R^{12}$ is a sulfonic acid, or $R^{10}$ is a sulfonic acid-substituted ethyl or propyl. Isomers that incorporate a spirolactone or spirosultone ring are non-fluorescent until the ring is opened.

Where A is $OR^7$, $R^{10}$ is aryl and $R^{12}$ is carboxy, the described dye is a fluorescein (Formula I) or a dihydrofluorescein (Formula II). Where A is $NR^8R^9$, $R^{10}$ is aryl and $R^{12}$ is carboxy, the described dye is a rhodol (Formula I) or a dihydrorhodol (Formula II).

The fluorinated xanthenes described thus far are optionally modified to possess a reactive group that is bound directly to the fluorophore by a single bond or by a linking moiety. Such a reactive dye may be used to prepare a dye-conjugate (as described below). The dyes are optionally substituted by an $R^7$ substituent that modifies the spectral properties of the dye, that makes the dye a substrate for an enzyme, makes the dye more cell-permeant, or makes the dye photoactivatible.

For all embodiments of the invention, at least one of the dye substituents $R^1$, $R^2$, $R^3$, $R^4$, $R^5$, $R^6$, $R^{10}$, $R^{12}$, $R^{13}$, $R^{14}$, $R^{15}$ or $R^{16}$ is required to be a covalently bound fluorine (F).

In one embodiment, one or more of $R^1$, $R^2 R^3$, $R^4$, $R^5$ and $R^6$ is F. In an additional embodiment, where at least one of $R^2$, $R^3$, $R^4$ and $R^5$ is F, none of $R^{12}$, $R^{13}$, $R^{14}$, $R^{15}$ and $R^{16}$ is F. In yet another embodiment, where at least one of $R^2$, $R^3$, $R^4$ and $R^5$ is F, at least one of $R^{12}$, $R^{13}$, $R^{14}$, $R^{15}$ and $R^{16}$ is F. In another embodiment at least one of the substituents (other than $R^3$ and $R^4$) is F.

Typically, where A=$OR^7$, either $R^2$ and $R^5$ are each F, or $R^3$ and $R^4$ are each F, or all of $R^2$, $R^3$, $R^4$ and $R^5$. Where A=$OR^7$, fluorination at $R^2$ and $R^5$ alone is preferred over fluorination at $R^3$ and $R^4$ alone because, inter alia, fluorination at $R^2$ and $R^5$ alone results in improved and greater photostability, lower pKa, higher quantum yield, and greater degree of substitution on polymers without quenching of fluorescence, relative to fluorescein, while maintaining substantially identical wavelengths of maximum absorption and emission. Fluorination at $R^3$ and $R^4$ alone, in contrast, results in improved photostability and a lower pKa relative to fluorescein, but with a lower quantum yield, no increase in useful degree of substitution and a shift in maximal absorption wavelength of about 20 nm, relative to carboxyfluorescein. Fluorination at each of $R^2$ and $R^3$ and $R^4$ and $R^5$, however, improves the photostability and lowers the pKa relative to either pair of fluorine substituents; but still shifts the absorption peak, shows no increase in useful degrees of substitution, and results in a lower quantum yield, relative to fluorescein.

Where A=$NR^8R^9$, preferably $R^5$ is F, resulting in a drop in the pKa of the dye relative to the non-fluorinated analog. Where $R^2$ is F, the pKa is comparable to that of the non-fluorinated compound; with both groups of compounds having comparable wavelengths of maximal absorption and emission relative to non-fluorinated compounds.

In another embodiment, at least one of $R^{12}$, $R^{13}$, $R^{14}$, $R^{15}$ and $R^{16}$ is F. In one embodiment, four of $R^{12}$, $R^{13}$, $R^{14}$, $R^{15}$ and $R^{16}$ is F. In another embodiment, each of $R^{13}$, $R^{14}$, $R^{15}$ and $R^{16}$ is F. In another embodiment, where at least one of $R^{12}$, $R^{13}$, $R^{14}$, $R^{15}$ and $R^{16}$ is F, none of $R^1$, $R^2$, $R^3$, $R^4$, $R^5$ and $R^6$ is F. For both A=$NR^8R^9$ and A=$OR^7$, where each of $R^{13}$ through $R^{16}$ is fluorinated, the resulting dyes react readily with nucleophiles, and where in addition $R^{11}$ and $R^{12}$, taken in combination, are spirolactone, the resulting dyes are well retained in cells or attach readily to biological molecules, relative to the non-fluorinated analogs. Dye conjugates of these polyfluorinated dyes exhibit increased fluorescence, and achieve higher degrees of fluorophore substitution before fluorescence quenching begins to occur. The dyes also possess increased photostability relative to non-fluorinated analogs. Where both the pendent aryl and xanthene rings are fluorinated, the photostability of the dye increases and its pKa decreases, relative to less-fluorinated and non-fluorinated compounds. In addition, where A=$OR^7$, the wavelength of maximum absorption shifts and the pKa and quantum yield are slightly lower than that of fluorescein.

In yet another embodiment of the invention, $R^1$ and $R^6$ are H, and $R^2$, $R^3$, $R^4$, and $R^5$ are H, F, Cl, Br or I, provided that at least one of the substituents is F, as permitted. In yet another embodiment, $R^{10}$ is F.

In another embodiment of fluorinated xanthenes, each $R^7$ is H and $R^{11}$ is H, and one or more of the remaining substituents are F, as permitted, resulting in a dye that has no visible fluoresceince until oxidized.

In one preferred embodiment of the invention, the dyes of the invention possess a quantum yield in aqueous solution (pH=6) of greater than 0.50. In another preferred embodiment of the invention, the dyes of the invention possess a pKa of less than 5.0. In another preferred embodiment of the invention, the extinction coefficient of the preferred dyes measured at a wavelength greater than 490 nm at pH 6.0 is greater than 60,000 $cm^{-1}M^{-1}$. In yet another preferred embodiment of the invention, the fluorinated dyes of the invention exhibit a fluorescence emission maximum that is shifted less than 15 nm relative to that of the non-fluorinated analog.

The spectral properties of selected embodiments of the dyes of the present invention are given in Table 1.

TABLE 1

Spectral properties of selected fluorinated fluoresceins and rhodols

| Dye | $\epsilon \times 10^{-3}$ $(cm^{-1}M^{-1})$ | Abs. (nm) | Em. (nm) | Quantum Yield | photo-decomposition* | pKa |
| --- | --- | --- | --- | --- | --- | --- |
| fluorescein | 82.2 | 490 | 514 | 0.92 | 17 | 6.5 |
| 2',7'-difluorofluorescein (29) | 84.7 | 490 | 513 | 0.97 | 8.0 | 4.7 |
| 4,5,6,7-tetrafluorofluorescein (34) | 85.6 | 508 | 527 | 0.85 | 6.6 | 6.1 |
| 2',4,5,6,7'-hexafluorofluorescein (26) | 81.2 | 508 | 527 | 0.96 | 4.0 | 4.8 |
| 5-(and-6)-carboxyfluorescein | 82.0 | 492 | 516 | 0.92 | 17 | 6.4 |
| 5-(and-6)-carboxy-2',7'-dichlorofluorescein | 80.3 | 504 | 530 | 0.75 | — | — |
| 5-(and-6)-carboxy 2',7'-difluorofluorescein (35, 36) | 85.9 | 492 | 516 | 0.92 | 9.0 | 4.8 |
| 5-(and-6)-carboxy-4',5'-difluorofluorescein (41) | 84.2 | 510 | 534 | 0.43 | 11 | 5.2 |
| 5-(and-6)-carboxy-2',4',5',7'-tetrafluorofluorescein (40) | 81.3 | 510 | 533 | 0.59 | 6.0 | 3.7 |
| 2',7'-dichlorofluorescein | — | — | — | — | — | 5.1 |
| 2',7'-dichloro-4,5,6,7-tetrafluorofluorescein (37) | 88.5 | 520 | 538 | 0.80 | 3.0 | 4.2 (6.2) |
| 6-carboxymethylthio-4,5,7-trifluorofluorescein (58) | 63.5 | 507 | 526 | 0.88 | 5.0 | 4.5 |
| 6-carboxymethylthio-2',4,5,7,7'-pentafluorofluorescein (59) | 87.5 | 507 | 526 | 0.86 | — | — |
| 6-azido-4,5,7-trifluorofluorescein (78) | 79.9 | 507 | 527 | 0.92 | — | — |

TABLE 1-continued

Spectral properties of selected fluorinated fluoresceins and rhodols

| Dye | $\epsilon \times 10^{-3}$ (cm$^{-1}$M$^{-1}$) | Abs. (nm) | Em. (nm) | Quantum Yield | photo-decomposition* | pKa |
|---|---|---|---|---|---|---|
| 6-amino-4,5,6-trifluorofluorescein | 77.5 | 503 | 522 | 0.053 | — | — |
| 9-(4-carboxy-2-sulfo)-6-hydroxy-2,7-difluoro-3H-xanthene-3-one | 83.8 | 497 | 517 | 0.92 | 7.3 | 4.3 |
| 1,2,4,5,7,8-hexafluoro-6-hydroxy-9 pentafluorophenyl-3H-xanthene-3-one (50) | — | — | — | 0.11 | 4.0 | 2.8 |
| 5-(and-6)-carboxy-N,N-dimethylrhodol | — | 518 | 544 | 0.26 | — | — |
| 5-(and-6)-carboxy-N,N-dimethyl-2'-fluororhodol | — | 519 | 553 | — | 5.0 | 4.2 |
| 5-(and-6)-carboxy-N,N-dimethyl-7'fluororhodol | — | 520 | 546 | — | 5.0 | 5.3 |
| 5-(and-6)-carboxyrhodol | 69.6 | 494 | 521 | 0.89 | 4.0 | 5.6 |
| 5-(and-6)-carboxy-2'-fluororhodol (55) | — | 495 | 518 | — | 4.0 | 3.8 |
| 5-(and-6)-carboxy-7'-fluororhodol | — | 494 | 519 | — | 4.0 | 5.2 |

*% of decreased fluorescence intensity after 33 minutes of illumination in fluorometer at wavelength of maximum excitation Reactive Dyes Useful for Dye Conjugates In one embodiment of the invention, the fluorophore contains at least one reactive group that is represented by —L—$R_x$ where L is a covalent linkage attaching the reactive group to the fluorinated fluorophore, and $R_x$ is the reactive group. In certain embodiments (see, for example Examples 64 and 73) the reactive group $R_x$ is attached to the dye by multiple intervening atoms that serve as a spacer to separate the resulting conjugated substance from the dye itself. Such separation frequently improves the properties of conjugates by reducing quenching of the dye's fluorescence, by removing the large dye from a site required for use of the conjugate in an enzymatic reaction or by reducing the effect of the dye on binding of a labeled ligand to its receptor. This covalent linkage, L, is also useful in improving the accessibility of the dye to an antibody that binds to the dye.

The covalent linkage L is optionally a single covalent bond, such that the reactive group $R_x$ is bound directly to the fluorophore at any of $R^2$–$R^5$ or $R^7$–$R^{16}$, preferably at one of $R^{13}$–$R^{16}$, more preferably at $R^{14}$ or $R^{15}$, or is present as a substituent on an alkyl, alkoxy, alkylthio or alkylamino substituent. The linkage L is typically selected so as to link the dye to the reactive group $R_x$ with stable chemical bonds, typically including carbon-carbon bonds, carbon-nitrogen bonds, nitrogen-nitrogen bonds, carbon-oxygen bonds and carbon-sulfur bonds. In addition to single, double, triple or aromatic carbon-carbon bonds, L typically includes ether, thioether, carboxamide, sulfonamide, urea, urethane or hydrazine functional moieties. Preferred L moieties have 1–20 nonhydrogen atoms selected from the group consisting of C, N, O and S. These preferred L moieties are composed of any combination of chemical bonds, including ether, thioether, amine, ester, carboxamide, sulfonamide, hydrazide bonds and aromatic or heteroaromatic bonds. Preferred L moieties are composed of any combination of single carbon-carbon bonds and carboxamide or thioether bonds. The longest linear segment of the linkage L preferably contains 4–10 nonhydrogen atoms including one or two heteroatoms.

Specific examples of L optionally include substituted or unsubstituted polymethylene, arylene, alkylarylene or arylenealkyl. In one embodiment of the invention, L contains 1–6 carbon atoms. In another embodiment of the invention, L is a single covalent bond. In yet another embodiment of the invention, L has the formula —$(CH_2)_a(CONH(CH_2)_b)_z$—, where a has any value from 0–5, b has any value from 1–5 and z is 0 or 1. In yet another embodiment of the invention, L is a thioether linkage.

The dyes of the invention that contain a reactive group, $R_x$, possess particular utility for the attachment of the fluorinated fluorophore to desired substances. The desired substances are typically organic substances but may also be inorganic substances such as glass or silicon derivatives. The reactive dyes of the invention fluorescently label a wide variety of substances, provided that the substance to be labeled contains a functional group that possesses suitable reactivity with at least one reactive group ($R_x$) on the dye. Typically, the reactive group is selected to possess suitable reactivity with a functional group already on the substance to be derivatized. The reactive group and functional group are typically an electrophile and a nucleophile that readily react to generate a covalent linkage. Typically, but not exclusively, the reactive group on the fluorophore is an electrophile, and the functional group on the substance to be derivatized is a nucleophile. Alternatively, the reactive group is a photoactivatable group, such as an azide, diazirinyl or azidoaryl derivative, and becomes chemically reactive only after illumination with light of an appropriate wavelength.

Generally, amines, thiols, and alcohols are the preferred nucleophilic functional groups for conjugation, as they are both more reactive and more commonly available for the modification of biomolecules. However, a wide variety of other functional groups, including carboxylic acids, aldehydes and ketones, react under conditions well understood by one skilled in the art. Selected examples of functional groups and linkages are shown in Table 2, where the reaction of an electrophilic group and a nucleophilic group yields a covalent linkage. The specific covalent linkage that attaches the fluorinated fluorophore to the conjugated substance typically depends on the functional group that is naturally present on the substance to be conjugated or is present as a result of derivatization of the substance to be conjugated according to methods generally known in the art. The functional group on the organic substance may be attached directly, or attached via any useful spacer or linker as defined below. A dye-conjugate is prepared from either a readily-available organic or inorganic substance, or from an initially non-reactive organic or inorganic substance that has been derivatized by an appropriate functional group.

TABLE 2

Examples of some routes to useful covalent linkages

| Electrophilic Group | Nucleophilic Group | Resulting Covalent Linkage |
|---|---|---|
| activated esters* | amines/anilines | carboxamides |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| azindines | thiols | thioethers |
| boronates | glycols | boronate esters |
| carboxylic acids | amines/anilines | carboxamides |
| carboxylic acids | alcohols | esters |
| carboxylic acids | hydrazines | hydrazides |
| carbodiimides | carboxylic acids | N-acylureas or anhydrides |
| diazoalkanes | carboxylic acids | esters |
| epoxides | thiols | thioethers |
| haloacetamides | thiols | thioethers |
| halotriazines | amines/anilines | ammotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a good leaving group (e.g. oxysuccinimidyl (—OC$_4$H$_4$O$_2$) oxysulfosuccinimidyl (—OC$_4$H$_3$O$_2$—SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$^a$ or —OCNR$^a$NHR$^b$, where R$^a$ and R$^b$, which may be the same or different, are C$_1$-C$_6$ alkyl, C$_1$-C$_6$ perfluoroalkyl, or C$_1$-C$_6$ alkoxy; or cyctohexyl, 3-dimethylaminopropyl, or N-morpholinoethyl).
**Acyl azides can also rearrange to isocyanates The types of functional groups typically present on the organic or inorganic substance to be conjugated include, but are not limited to, amines, thiols, alcohols, phenols, aldehydes, ketones, phosphates, imidazoles, hydrazines, hydroxylamines, disubstituted amines, halides, epoxides, sulfonate esters, purines, pyrimidines, carboxylic acids, or a combination of these groups. Amines, thiols, and alcohols are the preferred functional groups for conjugation, as they are both more reactive and more commonly available for the modification of biomolecules.

Other types of reactions that are useful for preparing dye-conjugates, especially of polymers, include catalyzed polymerizations or copolymerizations of alkenes and reactions of dienes with dienophiles, transesterifications or transaminations.

Dyes that are selected to conjugate with substances or materials having free amine groups are typically those dyes of the invention wherein $R_x$ is a carboxylic acid, a derivative of a carboxylic acid, or an activated ester of a carboxylic acid, preferably a succinimidyl or sulfosuccinimidyl ester. Amine-reactive dyes are of particular relevance as they are commonly used to label proteins and polypeptides, which possess free amine groups. Amine-reactive dyes are additionally used to label materials that have been substituted with free amine groups, such as amino-dextrans, or amine containing nucleotides, oligonucleotides, nucleic acids, amine-derivatized polymers or glasses, or amine-containing haptens.

Dyes that are selected to conjugate with materials having free thiol groups are preferably those dyes of the invention wherein $R_x$ is a haloalkyl, haloacetamide, halomethylbenzamide, a maleimido group, an epoxide or a sulfonate ester, wherein the sulfonic acid is an alkylsulfonic acid, perfluoroalkylsulfonic acid or an arylsulfonic acid. More preferably, the $R_x$ is an iodoacetamide, maleimido or a halomethylbenzamide. Additionally, the dyes of the invention where at least one of $R^{13}$–$R^{16}$ is fluorine react spontaneously with certain nucleophiles, including thiols, to yield stable dye-conjugates. Preferably such dyes are of Formula II, where A is $OR^7$, $R^7$ is a BLOCK, and $R^{10}$ and $R^{12}$, when taken in combination, form a spirolactone ring or spirosultone ring, wherein 1–4 of $R^{13}$, $R^{14}$, $R^{15}$ and $R^{16}$ is F.

Preferred alcohol- and phenol-reactive dyes are those dyes of the invention wherein $R_x$ is an isocyanate, a 3,5-dichloro-2,4,6-triazine, an acyl nitrile or a phosphoramidite.

Where dye-conjugates are prepared using a photoreactive dye of the invention, (wherein $R_x$ is an azide, diazirinyl or azidoaryl derivative), the conjugation reaction requires illumination of the reactive dye by light having a suitable wavelength, typically <400 nm. Where $R_x$ is a photoreactive group, $R_x$ is preferably an azide or an azidoperfluorobenzamido group.

Typically, $R_x$ is a reactive group that will form a covalent linkage with an amine, a thiol or an alcohol. Preferably, the reactive group $R_x$ is a carboxylic acid, an activated ester of a carboxylic acid, an acyl azide, an acyl halide, a symmetric or asymmetric anhydride, an acrylamide, an alcohol, a thiol, an aldehyde, an amine, an azide, an imido ester, a sulfonate ester, a haloacetamide, an alkyl halide, a sulfonyl halide, a hydrazine, an isocyanate, an isothiocyanate, or a maleimide group. More preferably, $R_x$ is a carboxylic acid, a succinimidyl ester, an amine, a haloacetamide, an alkyl halide, a sulfonyl halide, an isothiocyanate, a maleimide group or an azidoperfluorobenzamido group. Typically, where $R_x$ is an activated ester of a carboxylic acid, $R_x$ is a succinimidyl ester.

In one embodiment, $R_x$ is a reactive group that is an acrylamide, an activated ester of a carboxylic acid, an acyl azide, an acyl nitrile, an aldehyde, an alkyl halide, an amine, an anhydride, an aniline, an aryl halide, an azide, an aziridine, a boronate, a carboxylic acid, a diazoalkane, a haloacetamide, a halotriazine, a hydrazine, an imido ester, an isocyanate, an isothiocyanate, a maleimide, a phosphoramidite, a sulfonyl halide, or a thiol group.

Typically, the reactive group $R_x$ is the simplest version of the reactive group that still retains appropriate reactivity. Imido esters and ketones are typically esters of ketones of lower alkyls or aromatics.

In one embodiment of the invention, exactly one of $R^{13}$, $R^{14}$, $R^{15}$ and $R^{16}$ is a —L—$R_x$ moiety. In another embodiment of the invention, exactly one of $R^2$, $R^3$, $R^4$, $R^5$, $R^7$, $R^8$, $R^9$ or $R^{10}$ is an —L—$R_x$ moiety. In another embodiment, where $R^{12}$ is a carboxylic acid or sulfonic acid, there is an additional —L—$R_x$ moiety on the fluorinated dye.

The following specific examples of chemically reactive fluorinated dyes are examples of some preferred embodiments of the present invention:

5-(acryloylamino)fluorescein
4'-(((acryloyl)amino)methyl)fluorescein
6-amino-9-(2,4-dicarboxyphenyl)-3H-xanthene-3-one, succinimidyl ester
5-amino-2',7'-difluorofluorescein
6-amino-2',7'-difluorofluorescein
5-amino-2',4',5',7'-tetrafluorofluorescein
5-azido-2',7'-difluorofluorescein
4'-aminomethyl-2',7'-difluorofluorescein
5-aminomethyl-2',7'-difluorofluorescein
4',5'-bis(aminomethyl)-2',7'-difluorofluorescein
5-bromomethyl-2',7'-difluorofluorescein
9-(4-carboxy-2-sulfophenyl)-2,7-difluoro-6-hydroxy-3H-xanthene-3-one
9-(4-carboxy-2-sulfophenyl)-2,7-difluoro-6-hydroxy-3H-xanthene-3-one, succinimidyl ester
6-(carboxymethyl)thio-2',4,5,7,7'-pentafluorofluorescein, succinimidyl ester
6-(carboxymethyl)thio-2',4,5,7,7'-pentafluorofluorescein diacetate, succinimidyl ester
4-(carboxymethyl)thio-2',4,5,7,7'-pentafluorofluorescein diacetate, succinimidyl ester
6-(carboxymethyl)thio-4,5,7-trifluorofluorescein diacetate, succinimidyl ester
4-(carboxymethyl)thio-5,6,7-trifluorofluorescein diacetate, succinimidyl ester
6-(carboxymethyl)thio-4,5,7-trifluorofluorescein, succinimidyl ester
4-(carboxymethyl)thio-5,6,7-trifluorofluorescein, succinimidyl ester
6-(carboxymethyl)thio-4,5,6,7-tetrafluoro-2',4',5',7'-tribromo-fluorescein, succinimidyl ester
9-(2-carboxyphenyl)-2,7-difluoro-3,6-dihydroxy-9H-xanthene, succinimidyl ester
9-(2-carboxyphenyl)-2',7'-difluoro-3,6-dihydroxy-9H-xanthene diacetate, succinimidyl ester
5-((4-(chloromethyl)benzoyl)amino)-2',7-difluorofluorescein
5-((4-(chloromethyl)benzoyl)amino)-2',7-difluorofluorescein diacetate
5-chloromethyl-2',7'-difluorofluorescein
5-chloromethyl-2',7'-difluorofluorescein diacetate
5-(4,6-dichlorotriazinyl)amino-2',7'-difluorofluorescein
2-((((2',7'-difluorofluorescein-5-amino)carbonyl)methyl)thio)acetic acid, succinimidyl ester
6-(2',7'-difluorofluorescein-5-carbonyl)aminohexanoic acid, succinimidyl ester
2',7'-difluorofluorescein-5-carboxylic acid, succinimidyl ester
2',7'-difluorofluorescein-5-carboxylic acid, sulfosuccinimidyl ester, sodium salt
2',7'-difluorofluorescein-5-carboxylic acid, pentafluorophenyl ester
2',7'-difluorofluorescein-5-carboxylic acid, p-nitrophenyl ester
2',7'-difluorofluorescein-6-carboxylic acid, succinimidyl ester
2',7'-difluorofluorescein-5-carboxylic acid diacetate, succinimidyl ester
2',7'-difluorofluorescein-6-carboxylic acid diacetate, succinimdyl ester
2',7'-difluorofluorescein-5-iodoacetamide
2',7'-difluorofluorescein-6-iodoacetamide
2',7'-difluorofluorescein-5-isothiocyanate
2',7'-difluorofluorescein-6-isothiocyanate
2',7'-difluorofluorescein-5-maleimide
2',7'-difluorofluorescein-5-thiosemicarbazide
2',7'-difluoro-5-((pentafluorobenzoyl)amino)fluorescein
2',7'-difluoro-5-((pentafluorobenzoyl)amino)fluorescein diacetate
6-(((hydrazino)carbonyl)methyl)thio-4,5,7-trifluorofluorescein
4'-((iodoacetyl)amino)methyl-2',7'-difluorofluorescein
2',4',5',7'-tetrafluorofluorescein-5-carboxylic acid, succinimidyl ester
4',5'-difluoro-2',7'-dimethoxyfluorescein-5-carboxylic acid, succinimidyl ester Dye-Conjugates The reactive fluorinated xanthene dyes of the invention are useful for preparing dye-conjugates. Where a single fluorinated fluorophore is covalently conjugated to a substance, the conjugated substance is typically represented by —L—$S_c$, where $S_c$ is the conjugated substance itself, and —L— is a covalent linkage attaching the conjugated substance to the fluorinated fluorophore, as described previously.

Any organic or inorganic substance that contains an appropriate functional group with suitable cross-reactivity may be conjugated with a dye of the present invention. A conjugated substance may be conjugated to more than one fluorophore, which may be the same or different, or to a substance that is additionally modified by a hapten, such as biotin or digoxigenin. The preparation of conjugates of fluorescein and rhodol dyes is well-known in the art (Haugland et al., MOLECULAR PROBES HANDBOOK OF FLUORESCENT PROBES AND RESEARCH CHEMICALS, (1992); U.S. Pat. No. 5,442,045 to Haugland et al. (1995), incorporated by reference). However, the preparation of conjugates of the fluorinated fluorophores of the present invention impart the highly advantageous properties of the novel fluorinated fluorophores onto the resulting dye-conjugate.

Useful dye-conjugates of the present invention include conjugates of antigens, steroids, vitamins, drugs, haptens, metabolites, toxins, environmental pollutants, amino acids, peptides, proteins, nucleic acids, nucleic acid polymers, carbohydrates, lipids, ion-complexing moieties, polymers, or cells or cellular components.

In one embodiment of the invention, the conjugated substance ($S_c$) is an amino acid, protected amino acid, peptide, or protein. By amino acid is meant any of the natural amino acids or their optical isomers, as well as synthetic variations commonly known and utilized in the art. Common synthetic variations include amino acids that are protected on their amino, carboxylic acid, hydroxy, thiol, imidazole or other functional group. Other modified amino acids may be substituted by phosphate, or through glycosylation or acylation with a $C_1$ to $C_{22}$ carboxylic acid. Both peptides and proteins fall under the general category of peptides. While the specific demarcation line between peptides and proteins is not exact, it is typically recognized in the art that peptides have molecular weights of less than about 5,000 to 10,000 daltons, and proteins have molecular weights greater than about 5,000 to 10,000 daltons. Proteins typically possess at least secondary structure, and most often tertiary and quaternary structure.

Although peptides include molecules as small as dipeptides, where $S_c$ is a peptide, it is preferred that the peptide contain at least five amino acids, more preferably 5 to 36 amino acids. Preferred peptides to be conjugated to the dyes of the invention include, but are not limited to, neuropeptides, chemotactic peptides, cytokines (such as lymphokines), gastrointestinal peptides, toxins, protease substrates, synthetic peptides, experimental peptides, endothelin and protein kinase substrates. Dye-peptide conjugates of this invention include those labeled with at least one dye of the present invention in combination with a second fluorescent or nonfluorescent dye to form an energy transfer pair, or to a hapten such as biotin or digoxigenin, or to a reactive group $R_x$.

The protein conjugates of the present invention encompass a variety of proteins, including but not limited to enzymes, antibodies, catalytic antibodies, kinases, lectins, glycoproteins, histones, albumins, lipoproteins, avidin, strepavidin, protein A, protein G, phycobiliproteins, hormones, toxins and growth factors. By enzyme is meant any of a group of molecules that are typically but not exclusively produced by living cells, that function as catalysts for biochemical reactions. Some enzymes require small organic molecular cofactors for their activity. Antibodies, as used herein, are any of various proteins synthesized by animals in response to the presence of a foreign substance, for example, immunoglobulin G (IgG) and its fragments, monoclonal antibodies, "humanized" antibodies and catalytic antibodies. A kinase is one of a number of enzymes that catalyze the transfer of a phosphate group from ATP to another substrate, including polynucleotide kinase, protein kinase A and protein kinase C. Lectins, as used herein, are any of various proteins that selectively bind carbohydrates, such as cell surface carbohydrates, which can be used to identify cell type. Appropriate lectins are typically isolated from plants, preferably legumes, or from bacteria, fish or invertebrates. Preferred lectins are wheat germ agglutinin and concanavalin A. Glycoproteins, as used herein, are any of a class of conjugated proteins containing both carbohydrate and protein units. Lipoproteins, as used herein, are any class of conjugated proteins containing both lipid and protein units. Phycobiliproteins are any of several proteins isolated from algae, including but not limited to B-phycoerythrin, R-phycoerythrin, C-phycocyanine or allophycocyanin. In a preferred embodiment of the invention, the conjugated substance is an antibody, an antibody fragment, avidin, streptavidin, α-bungarotoxin, epidermal growth factor or a phallotoxin.

In another embodiment of the invention, the conjugated substance ($S_c$) is a single nucleic acid base, single nucleoside, single nucleotide or a nucleic acid polymer. By nucleotide is meant the basic structural unit of a nucleic acid, comprising an ester of a nucleoside and one or more phosphoric acid or polyphosphoric acid groups, optionally containing an additional linker or spacer for attachment of a fluorophore or other ligand, such as an alkynyl linkage (U.S. Pat. No. 5,047,519 to Hobbs, Jr. et al., (1991), incorporated by reference), an aminoallyl linkage (U.S. Pat. No. 4,711, 955 to Ward et al. (1987), incorporated by reference) or other linkage. Nucleotides, as used herein, include natural and synthetic derivatives, including deoxynucleotides, dideoxynucleotides, cyclonucleotides and abasic nucleotide analogs, wherein the base is replaced by a fluorophore or hapten. Preferably, the conjugated nucleotide is a mono-, di- or triphosphate ester of an adenosine, a guanosine, a uridine, a cytidine or a thymidine. More preferably, the conjugated nucleotide is a nucleoside triphosphate or a deoxynucleoside triphosphate or a dideoxynucleoside triphosphate.

Nucleic acid polymers are typically large, chainlike molecules containing phosphoric acid esters, sugars, and purine and pyrimidine bases. Polymers that are oligonucleotides are typically composed of fewer than 50 nucleotides, more typically composed of fewer than 25 nucleotides. Oligonucleotides are optionally deoxyribonucleic acid polymers (DNA) or ribonucleic acid polymers (RNA), or a hybrid thereof. Suitable oligonucleotides are optionally antisense oligonucleotides, or strands of DNA having a sequence identical to messenger RNA. DNA polymers are optionally single-stranded (ss), double-stranded (ds), triple-stranded or quadruple-stranded DNA. RNA is optionally single-stranded or double-stranded nucleic acid polymers. The nucleic acid polymer may be a natural polymer (biological in origin) or a synthetic polymer (modified or prepared artificially). The nucleic acid polymer optionally incorporates an unusual linker such as morpholine derivatized phosphates (AntiVirals, Inc., Corvallis Oreg.), or peptide nucleic acids such as N-(2-aminoethyl)glycine units (Wittung, et al., NATURE 368, 561 (1994)). In one embodiment of the invention, the dye is attached to the nucleotide, oligonucleotide or nucleic acid polymer via one or more purine or pyrimidine bases through an amide, ester, ether or thioether bond. In another embodiment of the invention, the dye is attached to the phosphate or carbohydrate by a bond that is an ester, thioester, amide, ether or thioether. In another embodiment of the invention at least one dye of the invention is conjugated to an oligonucleotide that is simultaneously labeled with at least a second dye to form a fluorescence energy transfer pair (as described in Ju et al., PROC. NATL. ACAD. SCI. USA 92, 4347 (1955), or to a hapten such as biotin or digoxigenin, or to an enzyme such as alkaline phosphatase, or to a protein such as an antibody.

In another embodiment of the invention, the conjugated substance ($S_c$) is a carbohydrate. By carbohydrate is meant any of the group of organic compounds composed of carbon, hydrogen and oxygen and occasionally nitrogen or sulfur, that include sugars, starches and celluloses. In one embodiment the conjugated sugar is an α- or β-glycoside or an aminoglycoside antibiotic. The conjugated substance is optionally a polysaccharide, such as dextran, FICOL, heparin, glycogen, amylopectin, mannan, inulin, starch, agarose and cellulose. All of these polysaccharides are readily available at low cost, high purity, low background absorbance and fluorescence and have relatively uniform physical properties. Where the conjugated substance is a polysaccharide, preferably the polysaccharide conjugate is a dextran or FICOL conjugate, more preferably a dextran conjugate.

In another embodiment of the invention, the conjugated substance ($S_c$), is a lipid. By lipid is meant one of a class of compounds that contains long-chain saturated or unsaturated aliphatic hydrocarbons (typically having 6–25 carbons) and their derivatives, such as fatty acids, alcohols, amines, amino alcohols, and aldehydes. The class of lipids include glycolipids, phospholipids and sphingolipids. Glycolipids are lipids that additionally contain carbohydrate units. Phospholipids are lipids containing esters of phosphoric acid containing one or two molecules of fatty acid or fatty alkyl ethers, an alcohol, and generally a nitrogenous base. Sphingolipids are lipids, such as sphingomyelin, that yield sphingosine or one of its derivatives as a product of hydrolysis. Alternatively, the conjugated substance is a lipid vesicle, such as a liposome or lipoprotein (as in Examples 121 and 122).

The conjugated substance is optionally an ion-complexing moiety. While any chelator that binds an ion of interest and gives a change in its fluorescence properties is a suitable conjugate, preferred ion-complexing moieties are crown ether, including diaryldiaza crown ethers, as described in U.S. Pat. No. 5,405,975 to Kuhn et al. (1995); derivatives of 1,2-bis-(2-aminophenoxyethane)-N,N,N',N'-tetraacetic acid (BAPTA) (Examples 103–105 and Example 104), as described in U.S. Pat. No. 5,453,517 to Kuhn et al. (1995) (incorporated by reference) and U.S. Pat. No. 5,049,673 to Tsien et al. (1991); derivatives of 2-carboxymethoxy-aniline-N,N-diacetic acid (APTRA), as described by Ragu et al. AM. J. PHYSIOL. 256, C540 (1989); and pyridyl-based and phenanthroline metal ion chelators (Example 106), as described in U.S. Pat. No. 5,648,270 to Kuhn et al. (1997) (incorporated by reference). Preferably the conjugated ion-complexing moiety is a diaryldiaza crown ether chelator or a BAPTA chelator. Fluorescent conjugates of ion-complexing moieties possess utility as indicators for the presence of a desired metal ion. While fluorescent ion-indicators are known in the art the incorporation of the fluorinated fluorophores of the present invention imparts the highly advantageous properties of the instant fluorophores onto the resulting ion indicator. In particular, the lower $pK_a$ of the dyes of the invention result in less sensitivity of the fluorescence of the ion indicator to changes in intracellular pH and the reduced photobleaching properties improves the ability to quantitate the fluorescence response of the indicator. Furthermore, conjugates based on 2',7'-difluorofluorescein are better excited by the 488-nm excitation line of the argon-ion laser than are the conjugates of 2',7'-dichlorofluorescein that were described by Tsien et al. (1991) (supra). These ion-sensing conjugates are optionally prepared in chemically reactive forms and further conjugated to polymers such as dextrans to improve their utility as sensors as described in U.S. Pat. Nos. 5,405,975 and 5,453,517 (supra).

Alternatively, the conjugates of the present invention are conjugates of cells, cellular systems, cellular fragments, or subcellular particles. Examples of this type of conjugated material include virus particles, bacterial particles, virus components, biological cells (such as animal cells, plant cells, bacteria, or yeast), or cellular components. Examples of cellular components that can be labeled, or whose constituent molecules can be labeled, include but are not limited to lysosomes, endosomes, cytoplasm, nuclei, histones, mitochondria, Golgi apparatus, endoplasmic reticulum and vacuoles.

Finally, the conjugates of the present invention are optionally dye-conjugates of polymers, polymeric particles, polymeric microparticles including magnetic and non-magnetic microspheres, polymeric membranes, conducting and non-conducting metals and non-metals, and glass and plastic surfaces and particles. Conjugates are optionally prepared by copolymerization of a fluorinated dye that contains an appropirate functionality while preparing the polymer, or by chemical modification of a polymer that contains functional groups with suitable chemical reactivity. In another embodiment of the invention, the conjugated substance is a glass or silica, which may be formed into an optical fiber or other structure.

In one embodiment of the invention, exactly one of $R^2$, $R^3$, $R^4$, $R^5$, $R^7$, $R^9$, $R^{10}$, $R^{11}$, $R^{13}$, $R^{14}$, $R^{15}$ or $R^{16}$ is a —L—$S_c$ moiety. In another embodiment of the invention, exactly one of $R^{13}$, $R^{14}$, $R^{15}$, or $R^{16}$ is an —L—$S_c$ moiety. Where exactly one of $R^{13}$, $R^{14}$, $R^{15}$, or $R^{16}$ is an —L—$S_c$ moiety, typically either each of the remaining of $R^{13}$, $R^{14}$, $R^{15}$, or $R^{16}$ is fluorine, or each of the remaining of $R^{13}$, $R^{14}$, $R^{15}$, or $R^{16}$ is hydrogen.

Preferably the conjugated substance is an amino acid, peptide protein, polysaccharide, ion-complexing moiety, nucleotide, oligonucleotide, nucleic acid, hapten, drug, lipid, phospholipid, lipoprotein, lipopolysaccharide, liposome, lipophilic polymer, polymer, polymeric microparticle, animal cell, plant cell, bacterium, yeast or virus.

Preparation of Dye-Conjugates

Conjugates of most low molecular weight drugs, peptides, toxins, nucleotides, phospholipids and other organic molecules are prepared by organic synthesis methods using the reactive dyes of the invention, by means well recognized in the art (Haugland, MOLECULAR PROBES HANDBOOK, supra, Sets 1–7, (1992)). Preferably, conjugation to form a covalent bond consists of simply mixing the reactive dyes of the present invention in a suitable solvent in which both the reactive dye and the substance to be conjugated are soluble. The reaction preferably proceeds spontaneously without added reagents at room temperature or below. For those reactive dyes that are photoactivated, conjugation requires illumination of the reaction mixture to activate the reactive dye. Chemical modification of water-insoluble substances, so that a desired dye-conjugate may be prepared, is preferably performed in an aprotic solvent such as dimethylformamide, dimethylsulfoxide, acetone, ethyl acetate, toluene, or chloroform. Similar modification of water-soluble materials is readily accomplished through the use of the instant reactive dyes to make them more readily soluble in organic solvents. Many of the dyes of the present invention are readily dissolved in aqueous solution by adjusting the pH of the solution to about 6 or higher.

Figure 1:
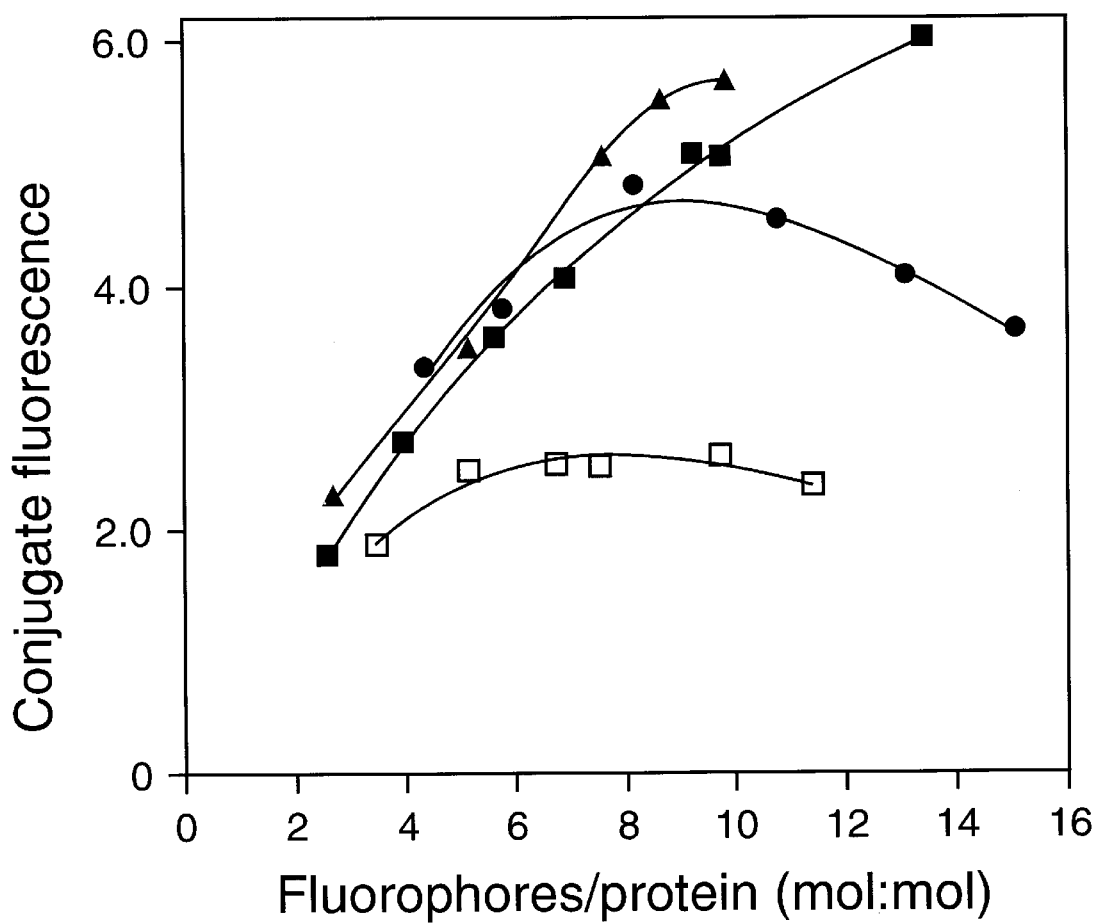
FIG. 1: A comparison of relative fluorescence as a function of the number of fluorophores attached per protein for goat anti-mouse IgG conjugates, as described in Example 112, prepared using 9-(4-carboxy-2-sulfophenyl)-2,7-difluoro-6-hydroxy-3H-xanthen-3-ol-6-one, succinimidyl ester (▲), 6-carboxymethylthio-2',4,5,7,7'- pentafluorofluorescein, succinimidyl ester (Compound 64) (■), 6-carboxy-2',7'-difluorofluorescein, succinimidyl ester (Compound 61) (●) and fluorescein isothiocyanate (FITC, □). Conjugate fluorescence is determined by measuring the fluorescence quantum yield of the conjugated dye relative to that of the free dye and multiplying by the number of fluorophores per protein.

Preparation of peptide or protein conjugates typically comprises first dissolving the protein to be conjugated in aqueous buffer at ~1–10 mg/mL at room temperature or below. Bicarbonate buffers pH ~8.3 are especially suitable for reaction with succinimidyl esters, phosphate buffers pH ~7.2–8 for reaction with thiol-reactive functional groups and carbonate or borate buffers pH ~9 for reaction with isothiocyanates and dichlorotriazines. The appropriate reactive dye is then dissolved in a nonhydroxylic solvent (usually DMSO or DMF) in an amount sufficient to give a suitable degree of conjugation when added to a solution of the protein to be conjugated. The appropriate amount of dye for any protein or reactive dyes is predetermined by experimentation in which variable amounts of the dye are added to the protein, the conjugate is chromatographically purified to separate unconjugated dye and the dye-protein conjugate is tested in its desired application (see for example FIG. 1). Following addition of the reactive dye to the protein solution, the solution is incubated for a suitable period (typically ~1 hour at room temperature to several hours on ice), the excess dye is removed by gel filtration, dialysis, HPLC, adsorption on an ion exchange or hydrophobic polymer or other suitable means. The dye-protein conjugate is used in solution or lyophilized. In this way, suitable conjugates can be prepared from antibodies, antibody fragments, avidins, lectins, enzymes, proteins A and G, cellular proteins, albumins, histones, growth factors, hormones, and other proteins. The approximate degree of dye substitution is determined from the long wavelength absorption of the dye-protein conjugate by using the extinction coefficient of the unreacted dye at its long wavelength absorption peak, the unmodified protein's absorption peak in the ultraviolet and by correcting the UV absorption of the conjugate for absorption by the dye in the UV. In this way data as in FIG. 1 are obtained.

Conjugates of polymers, including biopolymers and other higher molecular weight polymers are typically prepared by means well recognized in the art (for example, Brinkley et al., BIOCONJUGATE CHEM., 3, 2 (1992)). In these cases, a single type of reactive site may be available, as is typical for polysaccharides) or multiple types of reactive sites (e.g. amines, thiols, alcohols, phenols) may be available, as is typical for proteins. Selectivity of labeling is best obtained by selection of an appropriate reactive dye. For example, modification of thiols with a thiol-selective reagent such as a haloacetamide or maleimide, or modification of amines with an amine-reactive reagent such as an activated ester, acyl azide, isothiocyanate or 3,5-dichloro-2,4,6-triazine. Partial selectivity can also be obtained by careful control of the reaction conditions.

When modifying polymers with the dyes, an excess of dye is typically used, relative to the expected degree of dye substitution. Any residual, unreacted dye or a dye hydrolysis product is typically removed by dialysis, chromatography or precipitation (Example 111). Presence of residual, unconjugated dye can be detected by thin layer chromatography using a solvent that elutes the dye away from its conjugate. In all cases it is usually preferred that the reagents be kept as concentrated as practical so as to obtain adequate rates of conjugation.

In one aspect of the invention, the conjugate of the invention is associated with an additional substance, that binds either to the fluorophore or the conjugated substance through noncovalent interaction. In a specific embodiment, the additional substance is an antibody, an enzyme, a hapten, a lectin, a receptor, an oligonucleotide, a nucleic acid, a liposome, or a polymer. The additional substance is optionally used to probe for the location of the dye-conjugate, for example, as a means of enhancing the signal of the dye-conjugate.

In another embodiment of the invention, one of the reactive dyes of the invention is provided with instructions for conjugating the dye to any substance possessing an appropriate functional group, and optionally for recovering or purifying the materials labeled thereby. This combination of reactive dye and instructions therefore comprise a kit for labeling an appropriate substance. Selected appropriate substances include, but are not limited to, polymers of biological molecules (e.g. proteins, oligonucleotides or carbohydrates), polymeric resins and plastics (e.g. polystyrene), metals, glasses, and other organic or inorganic substances. The dyes of the present invention are well-suited for the preparation of such a kit.

BLOCKED dyes

In another embodiment of the invention, each $R^7$ substituent is optionally a BLOCK moiety, such that when BLOCK is present, the fluorescence of the fluorophore is substantially altered or diminished. In addition, one of $R^8$ or $R^9$ may be a BLOCK moiety. Typically BLOCK is a monovalent moiety derived by removal of a hydroxy group from phosphate or from sulfate, or a biologically compatible salt thereof; or a monovalent moiety derived by removal of a hydroxy group from a carboxy group of an aliphatic or aromatic carboxylic acid or of an amino acid, protected amino acid, peptide, or protected peptide; or a monovalent moiety derived by removal of a hydroxy group from an alcohol or from a mono- or polysaccharide. In each of these embodiments, BLOCK is selected to be removable from said compound by action of an appropriate enzyme.

Where $R^7$ is a BLOCK, the BLOCK-fluorophore bond is typically an ether or ester bond. Where $R^8$ or $R^9$ is a BLOCK, the BLOCK-fluorophore is typically an amide bond resulting from removal of a hydroxy group from the carboxylic acid on an amino acid or peptide, and a hydrogen atom from the amino moiety on the xanthene dye.

In another embodiment of the invention, the BLOCK moiety is selected to be a photolabile caging group. The dye-conjugates of the present invention have particular utility where the conjugated substances is removable by action of an enzyme in solution, in a biological fluid, in a cell or a cell extract or immobilized on a polymer such as a biological membrane. In this case the preferred conjugated moieties are those that significantly reduce or eliminate the long wavelength fluorescence of the parent dye and that upon action of the enzyme restore this fluorescence (a BLOCK moiety).

It is generally recognized that dihydroxyxanthenes derivatives can form mono or disubstituted ethers or esters with one or both of its hydroxyl groups and that when both hydroxyl groups are blocked the product is typically a colorless lactone that is devoid of long wavelength fluorescence. For the dyes of the invention that are fluoresceins, this corresponds to those dye conjugates where each $R^7$ is a BLOCK moiety, which may be the same or different (as shown below). For the dyes of the invention that are aminohydroxyxanthenes; such as rhodols, at least one of the substituents on the nitrogen atom is hydrogen and one of $R^8$ or $R^9$ is a BLOCK (as shown below).

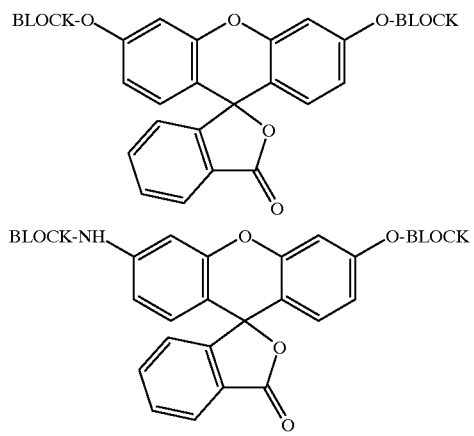

Numerous examples of useful enzyme substrates based on fluorescein dyes are known, including examples in which the fluorescein dye is conjugated as an alkyl ether (formally derived by removal of a hydroxy group from an alcohol), or to the anomeric hydroxyl group of a carbohydrate, as an ester of a phosphate or sulfate, or as an ester of an aliphatic carboxylic acid (such as acetate) or an aromatic carboxylic acid (such as p-guanidinobenzoate). Enzymes that are known to cleave these conjugated moieties back to the free dye include microsomal dealkylases (for example, cytochrome P450 enzymes), glycosidases (for example β-galactosidase, β-glucosidase, α-fucosidase, β-glucosaminidase), phosphatases, sulfatases, esterases, lipases, guanidinobenzoatases and others. Conjugates of rhodol dyes that are amides of aliphatic or aromatic carboxylic acids, amino acids or peptides are typically useful as peptidase substrates. In addition, those substrates that are rhodol dyes that are blocked as an amide of a carboxylic acid are optionally additionally blocked on the rhodol oxygen atom by an additional BLOCK that is the same or different. Preferably the enzyme substrates of the present invention are fluorinated on the aryl ring portion of the dye.

Particularly preferred are derivatives that comprise two identical BLOCK moieties that are acetate or a glycoside, such as β-D-galactopyranoside that are at least tetrafluorinated on the aryl substituent. As with their known nonfluorinated analogs, for example fluorescein diacetate (FDA) and fluorescein digalactoside (FDG), these derivatives can be used for detecting enzymes in live cells. However, the polyfluorinated aryl derivatives yield fluorescent products that are much better retained in cells than are the corresponding nonfluorinated dyes, making them useful for cell tracing (Example 132), as probes for study of cell efflux mechanisms (Example 134) and for detecting enzymatic activity in cells (Examples 129 and 132). Selected examples of the substrates such as 6-methoxy-4,5,7-trifluorofluorescein di(β-D-galactopyranoside) yield exceptionally high fluorescence in cells possessing lyosomal β-galactosidase activity (Example 130).

Tetrafluorination of the blocked substrate was shown to yield at least some products that were thiol adducts of glutathione, an abundant intracellular tripeptide in most cells (Example 133), and of proteins, most likely conjugated through thiol groups (Example 113). This reaction, which makes use of an unexpected property of the aryl-ring tetrafluorinated dyes, is not possible using the nonfluorinated analogs or with analogs that are only fluorinated in the xanthene portion.

Additionally preferred for detection of enzymes that have maximal turnover rates below pH 7 are substrates that are fluorinated at the 2' and 7' positions, in particular wherein BLOCK is phosphate or BLOCK is β-D-galactopyranoside. Because of both the lower $pK_a$ of the hydrolysis product and faster turnover rates, these substrates have greater utility in continuous assays of enzymatic activity that are made near the pH optimum of the enzymes when that pH optimum is below 7. In particular, these substrates are superior for detection of acid phosphatase activity (Example 128) and an acidic β-galactosidase from bovine testes (Example 129).

When the substrate is a fluorinated rhodol dye, the amine is preferably an amide of a carboxylic acid, amino acid or peptide and the hydroxy function is preferably an ether so that the hydrolysis product is a rhodol ether. Alternatively, the amine is an amide and the oxygen function is a phosphate ester or a glycoside. In either case, the aryl substituent is preferably tetrafluorinated and the substrate is a lactone.

Particular examples of preferred fluorinated dyes that incorporate at least one BLOCK include, but are not limited to:

3'-acetoxy-6'-acetylamino-4,5,6,7-tetrafluorospiro (isobenzofuran)-1(3),9'-(9H)xanthen-3-one
6'-acetylamino-3'-phosphoryloxy-4,5,6,7-tetrafluorospiro (isobenzofuran)-1(3H),9'-(9B)xanthen-3-one, disodium salt
6'-amino-3'-methoxy-4,5,6,7-tetrafluorospiro (isobenzofuran)-1(3H),9'-(9H)xanthen-3-one
5-chloromethyl-2',7'-difluorofluorescein diacetate
5-chloromethyl-2',7'-difluorofluorescein di-β-D-galactopyranoside
2',7'-difluoro-5-dodecanoylaminofluorescein di-β-D-galactopyranoside
2',7'-difluorofluorescein diacetate
2',7'-difluorofluorescein-5-carboxylic acid diacetate
2',7'-difluorofluorescein-5-carboxylic acid diacetate, succinimidyl ester
2',7'-difluorofluorescein-5-carboxylic acid di(2-nitrobenzyl ether)
2',7'-difluorofluorescein dibutyrate
2',7'-difluorofluorescein di(4,5-dimethoxy-2-nitrobenzyl ether)
2',7'-difluorofluorescein diethyl ether
2',7'-difluorofluorescein dioctadecanoate
2',7'-difluorofluorescein di-β-D-galactopyranoside
2',7'-difluorofluorescein di-β-D-glucuronide
2',7'-difluorofluorescein di(4-guanidinobenzoate)
2',7'-difluorofluorescein diphosphate, tetrasodium salt
2',7'-difluorofluorescein mono(4-guanidinobenzoate)
2',7'-difluoro-3-O-methylfluorescein phosphate
2',7'-difluoro-5-((pentafluorobenzoyl)amino)fluorescein diacetate
2',4,5,6,7,7'-hexafluorofluorescein diacetate
6'-L-leucylamino-3'-methoxy-4,5,6,7-tetrafluorospiro (isobenzofuran)-1(3H),9'-(9H)xanthen-3-one
2',4',5',7'-tetrafluorofluorescein diacetate
2',7'-difluorosulfonefluorescein diacetate
2',7'-difluorosulfonefluorescein diphosphate
4,5,6,7-tetrafluorofluorescein di-β-D-galactopyranoside
4,5,6,7-tetrafluorofluorescein diphosphate, tetraammonium salt In general these enzyme substrates are prepared by chemistry that has previously been demonstrated for fluorescein dyes and tested for their suitability as enzyme substrates by methods commonly practiced in the art. In many cases, however, the lower $pK_a$ that is typical of the dyes of this invention facilitates continuous measurement of enzyme activity at a lower pH than is possible with the fluorescein analog. This is particularly important for use in monitoring the activity of enzyme such as prostatic acid phosphatase that has a low pH optimum (Example 128). Furthermore the greater photostability that is typical of many of the dyes of this invention make them more reliable for quantitative assays.

When these "blocked" dyes are further substituted by a reactive group that is a haloalkyl, haloacetamide, halomethylbenzamide or by a lipophilic moiety, the conjugates not only possess utility as reporter molecules for a particular enzyme of interest, but are also well-retained in cells due to the conjugation of the dye to intracellular thiols, among which is glutathione, as described in U.S. Pat. No. 5,208,148 to Haugland et al. (1993), U.S. Pat. No. 5,362,628 to Haugland et al. (1994) and U.S. Pat. No. 5,576,424 to Mao et al. (1996), all incorporated by reference. "Blocked" dyes that are enzyme substrates that are additionally polyfluorinated at positions $R^{13}$–$R^{16}$ also possess utility as enzyme reporters that are well-retained in cells, due to the spontaneous reaction of these "bottom-ring" fluorine substituents with certain nucleophiles, including thiols, to yield stable dye-conjugates with intracellular components.

In an additional embodiment of the invention, the BLOCK moiety is a photolabile caging group, such that the fluorescence of the "blocked dye" is restored by photolytic illumination. Typically a caged dye is a dye wherein one or more $R^7$ substituents is a BLOCK that is a cage that is a substituted or unsubstituted derivative of o-nitroarylmethine, including α-carboxy o-nitroarylmethine and bis-(5-t-butoxycarbonylmethoxy)-2-nitrobenzyl (Example 101), a substituted or unsubstituted derivative of 2-methoxy-5-nitrophenyl or a substituted or unsubstituted derivative of desyl. Where the BLOCK is present as $R^8$ or $R^9$, the caging group is typically attached to the amine of the fluorophore via an intermediate carboxyl linker (i.e. via a carbamate linkage). The caged dyes and dye-conjugates of the present invention possess advantageous properties with respect to conventional caged fluoresceins, as the enhanced photostability of the free dyes is better able to withstand the intense illumination sometimes required to photolyse the caging group.

Applications of the Dye-Conjugates/Method of Use

The compounds of the present invention are generally utilized to stain a sample to give a detectable optical response under desired conditions by a) preparing a dye solution comprising a dye compound described above, at a concentration sufficient to yield a detectable optical response under the desired conditions; combining the sample of interest with the dye solution for a period of time sufficient for the dye compound to yield a detectable optical response under the desired conditions; and c) illuminating the sample at a wavelength selected to elicit the optical response. Optionally, the sample is washed to remove residual, excess or unbound dye. The dye compound typically forms a covalent or non-covalent association or complex with an element of the sample, or is simply present within the bounds of the sample or portion of the sample. In one embodiment, the staining is used to determine a specified characteristic of the sample by further comparing the optical response with a standard or expected response. For example, the dye solution is used to monitor specific components of the sample with respect to their spatial and temporal distribution in the sample. Alternatively, the dye compound preferentially binds to a specific ingredient in a sample, enabling the researcher to determine the presence or quantity of that specific ingredient. In another alternative, the dye compound is used to analyze the sample for the presence of a mechanism that responds specifically to the dye compound. The desired analysis to be performed determines the composition of the dye solution and chemical nature of the dye itself. In another example, the dye is bound by an antibody directed against the dye itself, typically resulting the fluorescence quenching of the dye (as in Example 135).

For biological applications, the dye solution is typically an aqueous or mostly aqueous solution that comprises one or more of the described dye compounds. In one aspect of the invention, the dye solution comprises a fluorinated fluorophore of Formula I or Formula II described above; alternatively, the dye solution comprises a dye compound that is a reactive dye analog of Formula I or Formula II dyes, as previously described; in yet another aspect of the invention, the dye solution comprises a conjugate of the subject dyes, as described above. The term "dye compound" is used herein to refer to all aspects of the claimed fluorinated dyes, including the parent fluorinated dyes, reactive fluorinated dyes, fluorinated dye-conjugates and BLOCKED dyes.

Dye solutions of the subject compounds are prepared according to methods generally known in the art. As with related known fluorophores, the dyes and dye-conjugates are generally soluble in water and aqueous solutions having a pH greater than or equal to about 6. Stock solutions of pure dyes, however, are typically dissolved in organic solvent before diluting into aqueous solution or buffer. Preferred organic solvents are aprotic polar solvents such as DMSO, DMF, N-methylpyrrolidone, acetone, acetonitrile, dioxane, tetrahydrofuran and other nonhydroxylic, completely water-miscible solvents. In general, the amount of dye or conjugate in the dye solution is the minimum amount required to yield detectable staining in the sample within a reasonable time, with minimal background fluorescence or undesireable staining. The exact concentration of dye or dye-conjugate to be used is dependent upon the experimental conditions and the desired results, and optimization of experimental conditions is typically required to determine the best concentration of stain to be used in a given application. The concentration of dye present in the dye solution typically ranges from nanomolar to micromolar. The required concentration for the dye solution is determined by systematic variation in dye or dye-conjugate concentration until satisfactory dye staining is accomplished. The starting ranges are readily determined from methods known in the art for use of similar compounds under comparable conditions for the desired optical response.

For those embodiments of the present invention that are substituted by alpha-acyloxyalkyl esters, or are substituted by sufficiently lipophilic moieties, the dye is optionally introduced into living cells by passive permeation through the cellular membranes. Less cell-permeant embodiments of the invention are optionally introduced into cells by pressure microinjection methods, scrape loading techniques (short mechanical disruption of the plasma membrane where the plasma membrane is peeled away from the cytoplasm, the dye is perfused through the sample and the plasma membrane is reassembled), patch clamp methods (where an opening is maintained in the plasma membrane for long periods) or phagocytosis. Any other treatment that will permeabilize the plasma membrane, such as electroporation, shock treatments or high extracellular ATP can be used to introduce the dye, dye-conjugate or BLOCKED dye into the cellular cytoplasm.

A detectable optical response means a change in, or occurrence of, a parameter in a test system that is capable of being perceived, either by direct observation or instrumentally. Such detectable responses include the change in, or appearance of, color, fluorescence, reflectance, chemiluminescence, light polarization, light scattering, or x-ray scattering. Typically the detectable response is a change in fluorescence, such as a change in the intensity, excitation or emission wavelength distribution of fluorescence, fluorescence lifetime, fluorescence polarization, or a combination thereof. The detectable optical response may occur throughout the sample or in a localized portion of the sample. The presence or absence of the optical response after the elapsed time is indicative of one or more characteristic of the sample. Comparison of the degree of staining with a standard or expected response can be used to determine whether and to what degree the sample possesses a given characteristic.

In one aspect of the invention, the dye solution comprises a fluorinated dye that non-covalently associates with organic or inorganic materials. Preferred embodiments of the fluorinated dyes that possess a lipophilic substituent can be used to stain lipid assemblies such as biological membranes or liposomes by non-covalent incorporation of the dye compound within the membrane, e.g. for use as probes for membrane structure or for incorporation in liposomes, lipoproteins, films, plastics, lipophilic microspheres or similar materials.

The fluorinated fluorescein dyes, and to a much lesser extent fluorinated rhodol dyes, are useful as coloring agents, tracers for detecting the flow of fluids such as in angiography, and tracing of fluid flow through gap junctions of neurons according to procedures known in the art for other xanthene derivatives. Fluorinated xanthene dyes are also useful in assays as haptens, according to known methods, because fluorination does not interfere with the recognition of the fluorophore by the anti-fluorescein antibody (Example 135).

In another aspect of the invention, the dye solution comprises a chemically reactive fluorinated dye that is used to chemically attach the dye to the corresponding functional group on any of a wide variety of materials, such as cells, tissues, proteins, antibodies, enzymes, drugs, hormones, lipids, nucleotides, nucleic acids, or natural or synthetic polymers. Fluorinated reactive dye compounds are selected to label reactive sites such as occur at the surface of cells, in cell membranes or in intracellular compartments such as organelles, or in the cell's cytoplasm, or to derivative low molecular weight compounds for their analysis by capillary zone electrophoresis (CZE), HPLC or other separation techniques. Certain reactive groups allow the retention of the fluorophore in cells or organelles by reacting with cellular materials. In particular, haloalkyl- or halomethylbenzamide-substituted fluorinated fluorophores are used to react selectively with intracellular components such as glutathione, or to retain the dye compounds within cells or within selected organelles where the dye compound is localized therein, according to methods previously described (U.S. Pat. No. 5,362,628 to Haugland et al, (1994); U.S. Pat. No. 5,576,424 to Mao et al. (1996) (in cells); and U.S. Pat. No. 5,459,268 to Haugland et al. (1995) and U.S. Pat. No. 5,686,261 to Zhang et al. (1997) (in mitochondria); all incorporated by reference). Polyfluoroaryl-substituted dye compounds are similarly retained in cells, in part by covalent attachment (see Examples 132 and 133). The reactive dyes are used to localize staining in a part of the sample, e.g., where the localization of the corresponding functional group is indicative of a characteristic of the sample; or to retain the dye in a specific portion of the sample for extended periods of time, e.g., to follow the stained portion of the sample through a period of time or sequence of events. Alternatively, the fluorinated reactive dyes are used according to this method to make dye-conjugates, as described above, that are separately useful for staining.

Typically, where the dye solution comprises a dye-conjugate, the dye conjugate is a labeled member of a specific binding pair, and is used as a fluorescent probe for the complementary member of that specific binding pair, each specific binding pair member having an area on the surface or in a cavity which specifically binds to and is complementary with a particular spatial and polar organization of the other. The fluorescent conjugate of a specific binding pair member is useful for detecting and optionally quantifying the presence of the complementary specific binding pair member in a sample, by methods that are well known in the art. Optionally, the complementary binding pair member is present in a animal cell, plant cell, bacteria, yeast or virus. Alternatively, the complementary member is immobilized on a solid or semi-solid surface, such as a polymer, polymeric membrane or polymeric particle (such as a polymeric bead). The dye-conjugate may also comprise a fluorinated dye in a BLOCKED form wherein the BLOCK is later removed by the action of an enzyme or light, or the conjugate may be one for which $R^{11}$ is H, in which case detection is made following oxidation of the probe to a fluorescent dye.

Representative specific binding pairs are shown in Table 3. Typically a specific binding pair member conjugated to the dye is a ligand or a receptor. As used in this document, the term ligand means any organic compound for which a receptor naturally exists or can be prepared. A receptor is any compound or composition capable of recognizing a spatial or polar organization of a molecule, e.g. epitopic or determinant site. Ligands for which naturally occurring receptors exist include natural and synthetic proteins, including avidin and streptavidin, antibodies, enzymes, and hormones; nucleotides and natural or synthetic oligonucleotides, including primers for RNA and single- and double-stranded DNA; lipids; polysaccharides and carbohydrates; and a variety of drugs, including therapeutic drugs and drugs of abuse and pesticides. The reactive dyes are used according to methods extensively known in the art, to prepare antibody conjugates for use in microscopy and immunofluorescent assays and nucleotide or oligonucleotide conjugates for nucleic acid hybridization assays and nucleic acid sequencing (e.g., U.S. Pat. Nos. 5,332,666 to Prober, et al. (1994); 5,171,534 to Smith, et al. (1992); 4,997,928 to Hobbs (1991); and WO Appl. 94/05688 to Menchen, et al.; all incorporated by reference) and a wide variety of other applications. The nucleotide conjugates of the present invention are readily incorporated by DNA polymerase (Example 126) and can be used for in situ hybridization or other techniques (Example 127). Numerous fluorescence polarization assays have been developed that use conjugates of fluorescein dyes to low molecular weight drugs and ligands which will be improved by the use of the fluorinated dye compounds, e.g., U.S. Pat. Nos. 4,420,568 to Wang (1983) and 4,510,251 to Kirkemo et al. (1985) (both incorporated by reference).

TABLE 3

Representative Specific Binding Pairs

| antigen | antibody |
| --- | --- |
| biotin | avidin (or streptavidin or anti-biotin) |
| IgG* | protein A or protein G |
| drug | drug receptor |
| toxin | toxin receptor |
| carbohydrate | lectin or carbohydrate receptor |
| peptide | peptide receptor |
| protein | protein receptor |
| enzyme substrate | enzyme |
| DNA (RNA) | apNA (aRNA)† |
| hormone | hormone receptor |
| ion | chelator |

*IgG is an immunoglobulin
†aDNA and aRNA are the antisense (complementary) strands used for hybridization Where a fluorinated dye is conjugated to a specific binding pair member that is a chelator of calcium, sodium, magnesium, potassium, or other biologically important metal ion, the dye-conjugate functions as an indicator of the ion, which indicators are optionally further conjugated to a biological or plastic polymer according to methods known in the art; e.g., using fluorinated analogs of the compounds described in U.S. Pat. Nos. 5,453,517 to Kuhn, et al. (1995); 5,405,975 to Kuhn, et al. (1995) (both incorporated by reference). Alternatively, the dye itself acts as a pH indicator ($H^{30}$ ion indicator) at pH values within 1.5 pH units of the individual dye's pKa. Those dye embodiments having fluorine at $R^2$ and $R^5$ are most useful as pH indicators over the range of pH 4–6. Typically the detectable optical response of the ion indicators is a change in fluorescence.

As indicated above, biological polymers can be labeled with a greater number of fluorinated dyes before quenching is observed. More typically, however, the substrate dye compound is a fluorinated dye that contains a –BLOCK moiety at positions $R^7$, $R^8$ or $R^9$ as defined above, such that cleavage of –BLOCK yields a detectable response indicative of the presence of enzyme activity, or $R^{11}$ is H, and oxidation of the dye yields a detectable response indicative of the presence of the oxidizing agent or enzyme. The enzyme substrates derived from fluorophores exhibiting enhanced photostability share that advantage. In addition, dye compounds having a pKa in an aqueous solution less than 6, more preferably less than about 5, are preferred for substrates to be used to assess enzyme activity in an acidic environment. For example, substrates where –BLOCK is cleaveable by a phosphatase enzyme are useful to detect acid phosphatase as well as alkaline phosphatase because, unlike substrates based on non-fluorinated analogs, a strong fluorescence response is evident with fluorinated substrates even when used in acidic environments. Alternatively, substrates wherein the dye compound has a pKa that is advantageous for acidic environments are useful in assessing the activity of enzymes found in acidic organelles, e.g. substrates for lysosomal glycosidases (see Example 130). Fluorinated diacetate compounds readily enter intact cells where the acetate moieties are cleaved by intracellular esterases in viable cells, restoring intrinsic fluorescence and serving as an indicator of viability. Similarly, fluorinated dyes that are substituted by acetoxymethyl ester (such as fluorinated analogs of calcein-AM, e.g. Compound 99, Example 99) readily enter intact cells and can serve as cell tracers or viability indicators, particularly where $R^{11}$ is H.

In another substrate embodiment, the dye compounds are fluorinated dyes for which $R^{11}$ is H, that are substrates for oxidative enzymes and other reactive oxidizing agents, particularly for peroxidase enzymes. In addition to the lowered pKa and enhanced photostability advantages of the parent fluorophores described above, the oxidative substrates possess additional unexpected advantages. Unlike their non-fluorinated analogs, fluorinated dihydrofluorescein and dihydrorhodol, are stable in aqueous solutions without the use of blocking groups on the hydroxyl or amine functions that typically reduce aqueous solubility. For example, Compound 84 (4,5,6,7-tetrafluorodihydrofluorescein, Example 85) is soluble in water to at least 2 mM, while existing diacetate fluorogenic peroxidase substrates are typically soluble only in the single-digit $\mu$M concentration range. Furthermore, 4,5,6,7-tetrafluorodihydrofluorescein is stable toward reaction of hydrogen peroxide during the period of analysis, in contrast to existing fluorogenic peroxidase substrates, which give fluorescence signal increase in the presence of hydrogen peroxide alone (i.e. in the absence of horseradish peroxidase).

The fluorinated enzyme substrates optionally contain additional substituents that provide additional advantages. Fluorinated fluorophores modified to contain a lipophilic tail according to the synthesis described in U.S. Pat. No. 5,208, 148 to Haugland et al. (1993) (incorporated by reference), are useful for permeabilizing substrates for intracellular enzymes. Fluorinated fluorophores that are polyfluorinated on the 9-carboxyphenyl substituent serve to retain the enzyme substituents within an intact cell.

In one embodiment of the invention, the polyfluorinated fluorescein substrate compounds are used to determine the efficiency of a cellular efflux pump of cells in a sample. Typically, the fluorinated dye compound used for this purpose contains at least four fluorine substituents, where the remaining substituents are H or halogen; preferably, the fluorinated compounds have 4 fluorines on the pendent phenyl ring, and 2 halogens (preferably fluorine or chlorine) on the xanthene ring system at the 2- and 7-positions ($R^2$ and $R^5$). Preferably the dye compounds are diacetates or diphosphates. The dye compound is used in the minimum concentration that gives a detectable fluorescence emission. Once the diacetate compounds are inside the cell, the blocking acetates are cleaved and the compound becomes highly fluorescent. The efficiency of the cellular efflux pump of cells in the sample is determined by comparing the fluorescence emission of cells in the sample with the fluorescence of cells having a known efflux efficiency. Where the efflux pump is impaired, inhibited, or absent, the fluorescent compound is well retained in the cell; where the efflux pump is present and functioning, the fluorescence of the cells decreases markedly. The photostability of the fluorinated compounds is advantageous for monitoring the time course of fluorescence.

Another application where the enhanced photostability and also lower pKa of the subject fluorinated dye compounds are particularly advantageous is use of the dye compounds for tracing. One or more fluorinated dyes conjugated to a biologically compatible polymer, including amino acid polymers (typically proteins, including fluorescent proteins), carbohydrate polymers (typically dextrans), and polymeric microspheres (typically polystyrene) are readily prepared for use as tracers according to methods known in the art. Other dye compounds useful as tracers include fluorinated analogs of calcein; caged fluorinated xanthenes; haloalkyl-, halomethylbenzamide-, and perfluorobenzyl-substituted dye compounds; fluorinated dye compounds conjugated to chelators of ions; and fluorinated dye compounds containing a lipophilic substituent, optionally incorporated into liposomes.

The dye compounds are most advantageously used to stain biological samples, i.e. samples that comprise biological components. In one aspect of the invention, the sample comprises heterogeneous mixtures of components, including intact cells, cell extracts, bacteria, viruses, organelles, and mixtures thereof. In another aspect of the invention, the sample comprises a single component or homogeneous group of components, e.g. biological polymers such as amino acid polymers, nucleic acid polymers or carbohydrate polymers, or lipid membrane complexes, whether the polymers are synthetic or natural.

The sample is typically stained by passive means, i.e., by incubation with the dye solution. Any other method of introducing the dye into the sample, such as microinjection of a dye solution into a cell or organelle, can be used to accelerate introduction of the dye into the sample. The dyes of the present invention are generally non-toxic to living cells and other biological components, within the concentrations of use, although those fluorinated dyes that are additionally substituted one or more times by Br or I are efficient photosensitizers. Cells have been incubated in dye solution for at least five hours without observable ill effects.

The sample can be observed immediately after staining. The sample is optionally combined with other solutions in the course of staining, including wash solutions, permeabilization and/or fixation solutions, and other solutions containing additional detection reagents. Washing following staining generally improves the detection of the optical response due to the decrease in non-specific background fluorescence after washing. Satisfactory visualization is possible without washing by using lower labeling concentrations. A number of fixatives and fixation conditions suitable for practicing this invention are known in the art, including formaldehyde, paraformaldehyde, formalin, glutaraldehyde, cold methanol and 3:1 methanol:acetic acid. Fixation is typically used to preserve cellular morphology and to reduce biohazards when working with pathogenic samples. Selected embodiments of the dyes described above are well retained in cells, and sample cells stained with these dyes retain considerable fluorescent staining after fixation. Fixation is optionally followed or accompanied by permeabilization, such as with acetone, ethanol, DMSO or various detergents, to allow bulky dye compounds, including dye-conjugates described above, to cross cell membranes, according to methods generally known in the art. The staining of the present invention is optionally combined with the use of an additional detection reagent that produces a detectable response due to the presence of a specific cell component, intracellular substance, or cellular condition, according to methods generally known in the art. Where the additional detection reagent has spectral properties that differ from those of the subject dye compounds, multi-color applications are possible.

At any time after or during staining, the sample is illuminated with a wavelength of light that results in a detectable optical response, and observed with a means for detecting the optical response. While the dye compounds are detectable colorimetrically, using ambient light, typically the dye compounds are detected by the fluorescence properties of the parent fluorophore. Upon illumination, such as by an ultraviolet or visible wavelength emission lamp, an arc lamp, a laser, or even sunlight or ordinary room light, the dye compounds, including dye compounds bound to the complementary specific binding pair member, display intense visible absorption as well as fluorescence emission. Selected equipment that is useful for illuminating the dye-conjugates of the invention includes, but is not limited to, hand-held ultraviolet lamps, mercury arc lamps, xenon lamps, argon lasers, laser diodes, and YAG lasers. These illumination sources are optionally integrated into laser scanners, fluorescence microplate readers, standard or mini fluorometers, or chromatographic detectors. This colorimetric absorbance or fluorescence emission is optionally detected by visual inspection, or by use of any of the following devices: CCD cameras, video cameras, photographic film, laser scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, a fluorescence microscope or a fluorometer, the instrument is optionally used to distinguish and discriminate between the fluorinated dye compound and a second fluorophore with detectably different optical properties, typically by distinguishing the fluorescence response of the fluorinated dye-conjugate from that of the second fluorophore. Where the sample is examined using a flow cytometer, examination of the sample optionally includes isolation of particles within the sample based on the fluorescence response of the dye compound by using a sorting device.

Typical Embodiments

Specific embodiments of fluorinated dyes, reactive fluorinated dyes and fluorinated dye conjugates include but are not limited to fluorinated analogs of the following specific compounds, where fluorine substitution may occur at the 1'-, 2-, 2'-, 3-, 4-, 4'-, 5-, 5'-, 6-, 7'-, or 8'-position, or any combination thereof, provided those positions are available for fluorination in the specifically listed fluorophore.

fluorescein
5-(and-6)-carboxyfluorescein
5-(and-6)-carboxyfluorescein diacetate
5-(and-6)-carboxy-4',5'-dimethylfluorescein
5-(and-6)-carboxy-4',5'-dimethylfluorescein diacetate
5-(and-6)-carboxy-2',7'-dimethylfluorescein
5-(and-6)-carboxy-2',7'-dimethylfluorescein diacetate
5-(and-6)-sulfofluorescein diacetate, sodium salt
fluorescein diacetate
5-carboxyfluorescein diacetate, acetoxymethyl ester
5-carboxyfluorescein
6-carboxyfluorescein
5-carboxyfluorescein diacetate
6-carboxyfluorescein diacetate
5-carboxy-2',4',5',7'-tetrabromosulfonefluorescein
5-iodoacetamidofluorescein
6-iodoacetamidofluorescein
5-(4,6-dichlorotriazinyl)aminofluorescein, hydrochloride
6-(4,6-dichlorotriazinyl)aminofluorescein
fluorescein-5-thiosemicarbazide
fluorescein-5-isothiocyanate
fluorescein-5-maleimide
fluorescein-5-isothiocyanate diacetate
5-(and-6)-carboxyfluorescein, succinimidyl ester
4'-(((iodoacetyl)amino)methyl)fluorescein
4',5'-di(((iodoacetyl)amino)methyl)fluorescein
5-(4,6-dichlorotriazinyl)aminofluorescein, diacetate
fluorescein-5-maleimide, diacetate
5-(bromomethyl)fluorescein
6-(bromomethyl)fluorescein
5-(aminoacetamido)fluorescein
4'-((aminoacetamido)methyl)fluorescein
6-(fluorescein-5-(and-6)-carboxamido)hexanoic acid, succinimidyl ester
5-carboxyfluorescein, succinimidyl ester
2',7'-dichlorodihydrofluorescein diacetate, succinimidyl ester
5-chloromethylfluorescein diacetate
2',7'-dichlorofluorescein-5-isothiocyanate
6-(fluorescein-5-carboxamido)hexanoic acid, succinimidyl ester
5-carboxy-2',4',5',7'-tetrabromosulfonefluorescein, succinimidyl ester, bis-(diisopropylethylammonium) salt
fluorescein-5-carbonyl azide, diacetate
5-aminofluorescein
5-(and-6)-chloromethylfluorescein diethyl ether
5-(and-6)-chloromethyl-2',7'-dichlorodihydrofluorescein diacetate
5-(3-carboxypropionyl)aminofluorescein
5-(N-dodecanoyl)aminofluorescein
5-(N-hexadecanoyl)aminofluorescein
5-(N-tetradecanoyl)aminofluorescein
5-(N-octadecanoyl)aminofluorescein
5-(N-hexadecanoyl)aminofluorescein diacetate
5-dodecanoylaminofluorescein diethyl ether
2',7'-dichlorodihydrofluorescein diacetate
5-(and-6)-carboxy-2',7'-dichlorodihydrofluorescein diacetate
dihydrofluorescein diacetate
6-carboxy-2',7'-dichlorodihydrofluorescein diacetate, di(acetoxymethyl ester)
fluorescein diethylether
fluorescein monoethylethyl ether, ethyl ester
5-(and-6)-ethoxycarbonylfluorescein ethyl ether ethyl ester
fluorescein monomethyl ether methyl ester
5-(and-6)-methoxycarbonylfluorescein methyl ether methyl ester
fluorescein octadecyl ester
fluorescein phalloidin
dexamethasone cadaverine fluorescein
colchicine fluorescein
avidin, fluorescein conjugate
concanavalin A, fluorescein conjugate
wheat germ agglutinin, fluorescein conjugate
ovalbumin, fluorescein conjugate
lactalbumin, fluorescein conjugate
albumin from bovine serum, fluorescein conjugate
protein A, fluorescein conjugate
streptavidin, fluorescein conjugate
peroxidase from horseradish, fluorescein conjugate
akaline phosphatase, fluorescein conjugate
ferritin, fluorescein conjugate
ferritin, cationized, fluorescein conjugate
deoxyribonuclease I, fluorescein conjugate
5-(and-6)-carboxyfluorescein diacetate, succinimidyl ester
5-(and-6)-carboxy-2',7'-dichlorofluorescein diacetate, succinimidyl ester
5-(and-6)-carboxy-4',5'-dichlorofluorescein diacetate, succinimidyl ester fluorescein α-bungarotoxin
fluorescein di-β-D-galactopyranoside
fluorescein mono-β-D-glucuronide
methotrexate, fluorescein, triammonium salt
formyl-Nle-Leu-Phe-Nle-Tyr-Lys, fluorescein derivative
fluorescein mono-β-D-glucopyranoside
fluorescein di-β-D-glucoside
fluorescein biotin
dexamethasone fluorescein
naloxone fluorescein
naltrexone fluorescein
dextran, fluorescein, 10,000 MW
dextran, fluorescein, 3000 MW, anionic
dextran, fluorescein, 70,000 MW
dextran, fluorescein, 40,000 MW
poly-L-lysine, fluorescein, 15,000–30,000 MW
dextran sulfate, fluorescein, 40,000 MW
dextran sulfate, fluorescein, 500,000 MW
dextran, fluorescein, 5–40 million MW
dextran, fluorescein, lysine-fixable
dextran, fluorescein with iodoacetamide
dextran, fluorescein lipophilic
Ficoll®, fluorescein, 400,000 MW
avidin, NeutraLite™, fluorescein conjugate
soluble β-glucan, fluorescein conjugate
protein G, fluorescein conjugate
fluorescein goat anti-mouse IgG (H+L) conjugate
fluorescein goat anti-rabbit IgG (H+L) conjugate
fluorescein goat anti-human IgG (H+L) conjugate
fluorescein goat anti-rat IgG (H+L) conjugate
fluorescein donkey anti-sheep IgG (H+L) conjugate
transferrin (human), fluorescein conjugate
5-(and-6)-carboxyfluorescein di-β-D galactopyranoside
fluorescein di-(4-guanidinobenzoate), dihydrochloride
5-butylaminofluorescein di-β-D galactopyranoside
5-octanoylaminofluorescein di-β-D galactopyranoside
5-dodecanoylaminofluorescein di-β-D galactopyranoside
5-hexadecanoylaminofluorescein di-β-D galactopyranoside
5-acetylaminofluorescein di-β-D galactopyranoside
2',7'-dichlorofluorescein di-β-D galactopyranoside
casein, fluorescein conjugate
fluorescein diphosphate, tetraammonium salt
histamine fluorescein, disodium salt
epidermal growth factor, fluorescein conjugate
ω-conotoxin GVIA, fluorescein conjugate
stachyose fluorescein, dipotassium salt
(fluorescein-5-thioureidyl)glycyl-L-histidine, dipotassium salt
(fluorescein-5-thioureidyl)glycylglycyl-L-histidine, dipotassium salt
N-(fluorescein-5-thiocarbamoyl)desferrioxamine, pentaammonium salt
fluorescein mono-(4-guanidinobenzoate), hydrochloride
6'-(O-(carboxymethyl))-2',7'-dichlorofluorescein-3'-(O-(N-acetyl-β-D-glucosaminide))
5-((5-aminopentyl)thioureidyl)fluorescein
5-((((2-aminoethyl)thio)acetyl)amino)fluorescein
4'-(aminomethyl)fluorescein, hydrochloride
4',5'-bis-(aminomethyl)fluorescein, dihydrochloride
5-(aminomethyl)fluorescein, hydrochloride
5-((2-aminoethyl)thioureidyl)fluorescein
5-((2-(and-3)-S-(acetylmercapto)succinoyl)amino)fluorescein
8-(fluoresceinyl)thioguanosine-3',5'-cyclicmonophosphate
fluorescein-5-(and-6)-sulfonic acid, trisodium salt
2',7'-bis-(2-carboxyethyl)-5-(and-6)-carboxyfluorescein, acetoxymethyl ester
2',7'-bis-(2-carboxyethyl)-5-(and-6)-carboxyfluorescein
N-(DMNB-caged fluorescein)-1,2-dihexadecanoyl-sn-glycero-3-phosphoethanolamine, triethylammonium salt
N-octadecyl-N'-(5-(fluoresceinyl))thiourea
dextran, DMNB-caged fluorescein
5-(N-dodecanoyl)aminofluorescein-bis-4,5-dimethoxy-2-nitrobenzl ether
fluorescein bis-(5-carboxymethoxy-2-nitrobenzyl)ether, dipotassium salt
5-(((2-(carbohydrazino)methyl)thio)acetyl)aminofluorescein
N-(5-fluoresceinthiocarbamoyl)-1,2-dihexadecanoyl-sn-glycero-3-phosphoethanolamine, triethylammonium salt Rhodol dyes may be fluorinated one or more times on the oxygen-substituted ring of the xanthene, the nitrogen-substituted ring of the xanthene or on the aromatic substituent at the 9-position of the xanthene ring, or at any combination of these positions. In their lactone forms the fluorinated rhodol dyes are best named by their Chemical Abstracts names, i.e. as fluorinated derivatives of 6'-amino-3'-hydroxyspiro(isobenzofuran)-1(3H),9'-(9H)xanthen-3-one Examples of preferred rhodol dyes include, but are not limited to, the fluorinated analogs of the following:
6-amino-9-(2'-carboxyphenyl)-3H-xanthene-3-one
6-amino-9-(4'-carboxy-2'-sulfophenyl)-3H-xanthene-3-one
6-amino-9-(4'-carboxy-2'-sulfophenyl)-3H-xanthene-3-one, succinimidyl ester
6-amino-9-(2',4'-dicarboxyphenyl)-3H-xanthene-3-one
6-amino-9-(2',4'-dicarboxyphenyl)-3H-xanthene-3-one, monosuccinimidyl ester
6-amino-9-(2',5'-dicarboxyphenyl)-3H-xanthene-3-one
6-amino-9-(2',5'-dicarboxyphenyl)-3H-xanthene-3-one, monosuccinimidyl ester
6'-amino-3'-methoxy-4,5,6,7-tetrafluorospiro (isobenzofuran)-1(3H),9'-(9H)xanthen-3-one
6-amino-9-(2'-sulfophenyl)-3H-xanthene-3-one
9-(2'-carboxy-(4'-((iodoacetyl)amino)phenyl)-6-dimethylamino-3H-xanthene-3-one
9-(2'-carboxy-4'-isothiocyanatophenyl)-6-dimethylamino-3H-xanthene-3-one
9-(2',4'-dicarboxyphenyl)-6-dimethylamino-3H-xanthene-3-one
9-(2',4'-dicarboxyphenyl)-6-dimethylamino-3H-xanthene-3-one, succinimidyl ester In particular, the following specific fluorinated dyes are preferred embodiments of the present invention:
6-amino-9-(2-carboxy-3,4,5,6-tetrafluorophenyl)-3H-xanthene-3-one
6-amino-9-(2,4-dicarboxyphenyl)-2-fluoro-3H-xanthene-3-one
6-amino-9-(2,4-dicarboxyphenyl)-7-fluoro-3H-xanthene-3-one
4',5'-bis((di(carboxymethyl)amino)methyl)-2',7'-difluorofluorescein (2',7'-difluorocalcein)
4',5'-bis((di(carboxymethyl)amino)methyl)-2',7'-difluorofluorescein, acetoxymethyl ester (2',7'-difluorocalcein AM)
6-carboxy-2',7'-difluorodihydrofluorescein, di(acetoxymethyl ester)
4-(carboxymethyl)thio-5,6,7-trifluorofluorescein
6-(carboxymethyl)thio-4,5,7-trifluorofluorescein
4-(carboxymethyl)thio-2',5,6,7,7'-pentafluorofluorescein
6-(carboxymethyl)thio-2',4,5,7,7'-pentafluorofluorescein
9-(2-carboxyphenyl)-2',7'-difluorodihydrofluorescein
9-(2-carboxyphenyl)-2',7'-difluorodihydrofluorescein diacetate 9-(2-carboxyphenyl)-2',4',5',7'-tetrafluorodihydrofluorescein
9-(4-carboxy-2-sulfophenyl)-2',7'-difluorofluorescein
9-(2,4-dicarboxyphenyl)-6-dimethylamino-3H-xanthene-3-one
4',5'-dichloro-2',7'-dimethoxy-4,5,6,7-tetrafluorofluorescein-5-carboxylic acid
2',7'-dichloro-4,5,6,7-tetrafluorofluorescein
1',8'-difluorofluorescein
2',7'-difluorofluorescein
2',7'-difluorofluorescein diacetate
4',5'-difluorofluorescein
2',7'-difluoro-6-hydroxy-3H-xanthene-3-one
2',7'-difluorofluorescein-5-carboxylic acid
2',7'-difluorofluorescein-5-carboxylic acid diacetate
2',7'-difluorofluorescein-5-carboxylic acid diacetate, acetoxymethyl ester
2',7'-difluorofluorescein-6-carboxylic acid
2',7'-difluorofluorescein-5-sulfonic acid
2',7'-difluorofluorescein-6-sulfonic acid
2',7'-dimethoxy-4,5,6,7-tetrafluorofluorescein
2',7'-dimethoxy-4,5,6,7-tetrafluorofluorescein-5-carboxylic acid
5-dodecanoylamino-2',7'-difluorofluorescein
2'-fluorofluorescein
4'-fluorofluorescein
2',4,5,6,7,7'-hexafluorofluorescein
2',4,5,6,7,7'-hexafluorofluorescein diacetate
1,2,4,5,7,8-hexafluoro-6-hydroxy-9-(pentafluorophenyl)-3H-xanthene-3-one
2',4',5',7'-tetrabromo-4,5,6,7-tetrafluorofluorescein
2',4',5',7'-tetrafluorofluorescein
2',4',5',7'-tetrafluorofluorescein-5-carboxylic acid
2',4',5',7'-tetrafluorofluorescein diacetate
4,5,6,7-tetrafluorofluorescein
4,5,6,7-tetrafluorofluorescein diacetate
4,5,6,7-tetrafluorofluorescein-2',7'-dipropionic acid
4,5,6,7-tetrafluorofluorescein-2',7'-dipropionic acid, acetoxymethyl ester
2',4',5',7'-tetraiodo-4,5,6,7-tetrafluorofluorescein Dye Synthesis The first step in preparing a fluorinated dye fluorescein or rhodol dye is the preparation of an appropriately substituted resorcinol or aminophenol, respectively. 4-Fluororesorcinol is prepared in a tedious fashion with modest yield from 1,3-dimethoxyaniline via the Balz-Schiemann reaction (Durrani et al., J. CHEM. SOC. PERKIN TRANS. I, 1658 (1980), followed by boron tribromide-mediated demethylation. 2-Fluororesorcinol and 2,4-difluororesorcinol can be prepared in low yield as a mixture upon electrophilic fluorination of resorcinol (Patrick et al. J. ORG. CHEM. 51, 3242 (1986)) or its diethers (Lerman et al. J. ORG. CHEM. 49, 806 (1984)), using reagents such as SELECTFLUOR (trademark of Air Products for 1-chloromethyl-4-fluoro-1,4-diazonia-bicyclo[2.2.2]octane, bistetrafluoroborate) followed by preparative HPLC separation and then dealkylation. More conveniently, fluorinated resorcinols and aminophenols are synthesized reliably and in high yield beginning with the appropriate (commercially available) polyfluoronitrobenzenes or their alkoxy-substituted derivatives, many of which are commercially available (Examples 1–4). Two equivalents of alkoxide or benzyloxide are added, displacing any fluorine atoms that occur ortho and para to the nitro group. The nitro group is reduced via catalytic hydrogenation or chemical reduction, followed by diazotization and in situ reductive dediazonization using hypophosphorous acid; alternatively, diazonium cations can be isolated pure as tetrafluoroborate or hexafluorophosphate salts, followed by reduction to the arene with sodium borohydride. Dealkylation with boron tribromide or another ether-cleaving reagent, or in the case of benzyl ethers, catalytic hydrogenolysis, then affords isomerically and constitutionally pure fluorinated resorcinols. Several other moieties are optionally present during these synthetic steps, provided that they resist the steps required for synthesis of the fluorinated resorcinol. These moieties include alkyl, carboxyalkyl, chloro, bromo, iodo, alkoxy and hydroxy, while hydroxy moietites may also be formed during cleavage of alkoxy groups present in the starting material.

Fluorinated aminophenols are prepared using similar methodology. For instance, alkyl-substituted amine nucleophiles may be substituted onto a polyfluoronitrobenzene, in sequence with alkoxide or benzyloxide, resulting in fluorinated aminophenols after the nitro group is removed by reduction followed by diazotization and hydrodediazoniation (Examples 18–22). These fluorinated aminophenols may then be used to prepare fluorinated rhodol fluorophores. A different means of synthesizing fluorinated aminophenols involves converting commercially available fluorinated nitrophenyl ketones and aldehydes into the corresponding phenolic esters using Baeyer-Villiger oxidation chemistry. N-Substitution is accomplished via reductive amination or by direct allylation to yield the desired N-substituted aminophenol. Deacylation of the phenolic hydroxyl then gives the desired fluorinated aminophenol (Examples 23–25).

Xanthylium dyes having fluorine substituents on the xanthene portion of the dye are typically prepared by condensation of the appropriate fluorinated resorcinol with various derivatives of phthalic acid or phthalic anhydride or sulfobenzoic acid or anhydride, including phthalic anhydride, trimellitic anhydride, nitrophthalic anhydride, o-sulfobenzoic anhydride, sulfoterephthalic acid, or with benzaldehydes (when followed by oxidation, as in Example 58 or Example 82) or with aliphatic dicarboxylic acids or anhydrides such as a succinic anhydride or a glutaric anhydride (Example 83). This condensation occurs in the presence or absence of various acid catalysts (such as zinc chloride or methanesulfonic acid), and after an aqueous workup yields the desired fluorinated xanthylium dye.

Fluorinated xanthylium dyes are also obtained by the condensation of two equivalents of a resorcinol, either unsubstituted or substituted, with a fluorinated benzenecarbonyl compound. Particularly useful fluorinated carboxyphenyl compounds include tetrafluorophthalic anhydride, tetrafluorophthalic acid or fluorophthalic acid derivatives, pentafluorobenzoic acid, and fluorinated benzaldehydes such as pentafluorobenzaldehyde (an oxidation step is required after using fluorinated benzaldehydes to give the fluorescent xanthylium dye). In the resulting dye the fluorinated aryl ring pendant to the xanthene ring system is the "aryl substituent" of the dye. For fluorinated xanthylium dyes that have fluorine atoms at the 4- and 6-positions of the bottom ring, heteroatom nucleophiles such as reduced glutathione, mercaptoacetic acid (Examples 59, 60, 61), mercaptoethylamine and azide are substituted at the 4- or 6-positions, by displacement of a fluoride ion, affording a synthetic route to functionality that can be elaborated into a variety of reactive groups for subsequent conjugation chemistry. For example, the carboxylate group of the mercaptoacetic acid adduct is converted into a reactive succinimidyl ester (Examples 64, 65, 67 and 68), or the amine of the mercaptoethyl amino is converted into a reactive isothiocyanate, maleimide or haloacetamide; alternatively the azide group is reduced to an amine, which is then acylated with iodoacetic anhydride to provide an iodoacetamide.

Fluorinated xanthylium dyes are also obtained beginning with polyfluorinated benzonitriles. Addition of an alkoxide or a benzyloxide to the benzonitrile displaces the fluorine atoms ortho- and para- to the nitrile group. Addition of an arylorganometallic reagent, such as pentafluorophenylmagnesium chloride, converts the nitrile group to an imine, which is subsequently hydrolyzed, affording a substituted benzophenone with alkoxy groups at the 2- and 4-positions. The alkoxy groups are dealkylated, for example with hydrobromic acid and acetic acid. Treatment with sodium hydroxide in methanol then gives a xanthenone, in which the 2-hydroxy group has displaced the 2'-fluorine atom; concomitantly, an alkoxy group displaces the 4'-fluorine atom. The 3-hydroxy group in the resulting xanthone is typically protected by a base-stable protecting group, such as a 2-methoxyethylmethyl ether (MEM ether), and then an arylorganometallic reagent such as pentafluorophenyl magnesium chloride or an alkyl lithium reagent is added to the xanthone carbonyl group. Subsequent treatment with hydrobromic and acetic acid dehydrates the resulting tertiary carbinol to the desired xanthylium dye, with concomitant conversion of the 6-methoxy group to a hydroxyl group.

For asymmetric xanthylium dyes such as rhodols and unsymmetrical xanthylium dyes such as rhodols and unsymmetrical fluoresceins, condensation can be performed using one equivalent each of the appropriate substituted or unsubstituted resorcinol with one equivalent of a different resorcinol (as in Khanna et al., U.S. Pat. No. 4,439,359 (1984)), aminophenol and with one equivalent of the appropriate phthalic acid derivative or benzaldehyde (phthalic anhydride, trimellitic anhydride, nitrophthalic anhydride, tetrafluorophthalic anhydride, sulfoterephthalic acid, succinic anhydride, or their corresponding phthalic acids or pentafluorobenzaldehyde) using acid catalysis. The desired asymmetrical xanthylium dye is separated from any unwanted symmetrical dye side-product using chromatographic techniques well-known in the art.

Alternatively, asymmetric xanthylium dyes are constructed in a stepwise fashion: A selected fluorinated resorcinol or aminophenol is condensed with one equivalent of the appropriate phthalic acid derivative or benzaldehyde. The resulting benzophenone derivative is typically isolated, purified and then condensed with one equivalent of a different fluorinated or non-fluorinated resorcinol or aminophenol yielding the asymetric dye. Alternatively, the symmetrical xanthylium dye is hydrolyzed by strong base to the benzophenone compound and treated with a different aminophenol or resorcinol to yield the unsymmetrical product.

Post-condensation modifications of fluorinated xanthylium dyes are typically strictly analogous to known methods of fluorescein modification. For example, the xanthenone portion of a fluorinated fluorescein can be halogenated at selected non-fluorinated positions by treatment with the appropriate halogenating agent, such as liquid bromine. Where either or both of the 4' or 5' positions of a fluorinated fluorescein are occupied by hydrogen atoms, the 4' and 5' positions can be substituted with aminomethyl groups using Mannich conditions (as in Kirkemo et al., U.S. Pat. No. 4,510,251, supra). As used herein, substituted amines optionally include iminodiacetic acid (Examples 98, 99) and aminoacids. When trimellitic anhydride is used in the dye synthesis, and thus a bottom-ring carboxylate is present in the fluorinated dye, this carboxylate group can be converted into a thiol-reactive chloromethyl or bromomethyl substituent by reduction to the corresponding alcohol followed by treatment with HCl or HBr (Example 72). When trimellitic anhydride or its derivatives is used in the dye synthesis, two isomeric carboxylates are typically formed. These isomers are separated (General Method J) or, as in most cases, used as the mixture of isomers. The reduced derivatives of fluorinated xanthylium dyes (i.e., those of formula 2) are prepared by chemical reduction of the xanthenone portion with zinc dust or borohydride in organic solvents. These dihydrofluorinated dyes can serve as substrates for enzymes that take up electrons, or in the detection of chemical oxidizing agents, reactive oxygen species or nitric oxides. Other enzyme substrates of the fluorinated xanthylium dyes involve, for example, acylation of the phenolic hydroxyls of fluorinated dyes with phosphate (to give phosphatase substrates, Examples 96 and 97), carboxylic acids (to give esterase substrates, Examples 26, 28, 29, 31 and 32), alkylation with alkyl groups (to give dealkylase substrates) and carbohydrates to yield glycosidase substrates (Examples 90–95). In addition, rhodols are optionally acylated by methods well known in the art to yield amido derivatives or treated with sulfonyl halides to yield sulfonamides.

The dihydroxanthene and xanthylium versions of the dyes of the invention and their conjugates are generally freely interconvertible by chemical oxidation or reduction. Reagents useful for this reduction include borohydrides, aluminum hydrides, hydrogen in the presence of a hydrogenation catalyst, and dithionites. Choice of the reducing agent may depend on the ease of reduction of other reducible groups in the molecule. A wide variety of oxidizing agents mediate the oxidation of the dihydroxanthenes, including molecular oxygen in the presence or absence of a catalyst, nitric oxide, peroxynitrite, dichromate, triphenylcarbenium and chloranil. The xanthenes are also oxidized by enzyme action, including the action of horseradish peroxidase in combination with peroxides (Example 131) or solely by nitric oxide. This oxidation may occur in a cell, or in a cell-free solution.

Specific embodiments of the dyes of the present invention that possess particular utility for the preparation of dye-conjugates are amino, hydroxy and carboxy derivatives of the fluorinated fluorophores, as these derivatives are readily converted to a wide variety of other reactive derivatives. These reactive derivatives in turn can be conjugated to amino acids, peptides, proteins, nucleotides, oligonucleotides, nucleic acids, carbohydrates, polysaccharides, lipids, drugs, toxins, ligands and other molecules of interest using standard chemistry that is typically accomplished at or near room temperature. For instance, amine derivatives are converted to isocyanates, isothiocyanates, ureas, thioureas, urethanes, semicarbazides, dichlorotriazinyl amines, amides, haloacetamides, maleimides, acrylamides, azides, hydrazines or alkylated amines; carboxylic acids are converted to esters or activated esters capable of forming amides or esters, amides, hydrazides, acid halides, acyl azides, acyl nitriles or reduced to aldehydes or alcohols; hydroxy groups are esterified, alkylated to ethers including glycosides, or converted to alkylating agents such as halogens or sulfonate esters. Other synthetic stratagies for the preparation of useful reactive derivatives include the formation of aldehydes, glyoxals, thiols, epoxides, aziridines, sulfonyl halides, imido esters, borates or phosphoramidites. Alkenes for use in polymerization can be incorporated by various means, including reacting with functionalized styrenes or allylamines or by reaction of an amine on the dye with an acrylic acid derivative. All of these reactions are accomplished using methods well known in the art. The reactions that are typically used to couple the reactive fluorophores of the invention with molecules of interest include, but are not limited to, those listed in Table 2.

Examples of synthetic strategies for selected fluorinated fluorophores, as well as their characterization, synthetic precursors, conjugates and method of use are given below. The examples below are given so as to illustrate the practice of this invention. They are not intended to limit or define the entire scope of this invention.

EXAMPLES

Proton Nuclear Magnetic Resonance ($^1$H NMR) signals are reported as δ (ppm) downfield from tetramethylsilane. Fluorine Nuclear Magnetic Resonance ($^{19}$F NMR) signals are reported as φ (ppm) upfield from CFCl$_3$. Phosphorus Nuclear Magnetic Resonance ($^{31}$P NMR) signals are reported as δ (ppm) upfield from an external H$_3$PO$_4$ standard.

Preparation of Fluorinated Resorcinols

General Method A

Sodium methoxide (1.0 M) is prepared by adding freshly cut sodium metal (rinsed with toluene) portionwise to anhydrous methanol (Aldrich) under nitrogen in flame-dried glassware with stirring; an ice-water bath is used to control the reaction temperature. To a neat fluorinated nitrobenzene (1.0 equivalents) under nitrogen at room temperature in flame-dried glassware is added sodium methoxide solution (2.2 equivalents) via syringe over the course of 5–10 minutes, with stirring. The resulting reaction mixture is stirred at room temperature, while monitoring the progress of the reaction by TLC. Additional sodium methoxide solution is added as necessary. Once the reaction reaches completion (1–24 hours), several drops of 1 M citric acid are added, and the reaction mixture is partitioned between ether and water. The aqueous layer is extracted once with ether. The combined organic portions are washed once with brine, dried over anhydrous sodium sulfate, and concentrated under reduced pressure to give the desired dimethoxyfluoronitrobenzene.

Example 1

Preparation of 3,5-Difluoro-2,4-dimethoxynitrobenzene (1)

Beginning with 9.8 g (50 mmol) of 2,3,4,5-tetrafluoronitrobenzene (Aldrich), Compound 1 is obtained as 10.92 g (99%) of a pale yellow solid: m.p. 32.0–32.5° C.; $^1$H NMR (CDCl$_3$) 7.52 (dd, 1H), 4.12 (s, 3H), 4.04 (s, 3H); $^{19}$F NMR (CDCl$_3$) 132.0 (m, 1F), 141.9 (d, 1F). Anal. calc. for C$_8$H$_7$NO$_4$F$_2$: C, 43.85; H, 3.22; N, 6.39. Found: C, 43.84; H, 3.15; N, 6.15.

Example 2

Preparation of 2,4-Dimethoxy-3-fluoronitrobenzene (2)

Beginning with 2,3,4-trifluoronitrobenzene (5.53 g, 31.2 mmol, Aldrich), Compound 2 is obtained as 6.30 g (99%) as a pale yellow crystalline solid. An analytical sample is obtained by crystallization from light petroleum ether/dichloromethane: m.p. 59–61° C.; $^1$H NMR (CDCl$_3$) 7.72 (dd, 1H), 6.71 (dd, 1H), 4.08 (s, 3H), 3.95 (s, 3H); $^{19}$F NMR (CDCl$_3$) 149.1 (d). Anal. calc. for C$_8$H$_8$NO$_4$F: C, 47.77; H, 4.01; N, 6.96. Found: C, 47.64; H, 4.05; N, 6.80.

Example 3

Preparation of 2,4-Dimethoxy-5-fluoronitrobenzene (3)

Beginning with 2,4,5-trifluoronitrobenzene (1.00 g, 5.65 mmol, Aldrich), the initial reaction affords a mixture (separated by flash chromatography) of the monomethoxy adduct as 0.54 g (51%) of a colorless powder (m.p. 80–82° C.; $^1$H NMR (CDCl$_3$) 7.89 (dt, 1H), 6.81 (dd, 1H), 3.98 (s, 3H); $^{19}$F NMR (CDCl$_3$) 116.8 (td, 1 F), 136.5 (m, 1 F). Anal. calc. for C$_7$H$_5$NO$_3$F$_2$: C, 44.46; H, 2.66; N, 7.41. Found: C, 44.33; H, 2.62; N, 7.21) and Compound 3 as 0.42 g (37%) of a colorless powder: m.p. 146–149° C.; $^1$H NMR (CDCl$_3$) 7.81 (dd, 1H), 6.59 (d, 1H), 3.99 (s, 3H), 3.97 (s, 3H); $^{19}$F NMR (CDCl$_3$) 142.9 (dd). Anal. calc. for C$_8$H$_8$NO$_4$F: C, 47.77; H, 4.01; N, 6.96. Found: C, 47.81; H, 3.96; N, 6.84. The isolated monomethoxy adduct is converted into Compound 3 in quantitative yield by treatment with 1.4 equivalents of sodium methoxide solution.

Example 4

Preparation of 2,4-Dimethoxy-3,5,6-trifluoronitrobenzene (4)

Beginning with 2,3,4,5,6-pentafluoronitrobenzene (5.00 g, 23.5 mmol, Aldrich) the monomethoxy adduct 4-methoxy-2,3,5,6-tetrafluoronitrobenzene is first obtained as 5.30 g (100%) of ivory crystals after crystallization from light petroleum ether/dichloromethane: m.p. 33–37° C.; $^1$H NMR (CDCl$_3$) 4.21 (s); $^{19}$F (CDCl$_3$) 147.3 (q, 2 F), 156.0 (q, 2 F). Anal. calc. for C$_7$H$_3$NO$_3$F$_4$: C, 37.39; H, 1.34; N, 5.89. Found: C, 37.35; H, 1.34; N, 6.22. Treatment of this monomethoxy adduct (2.50 g, 11.1 mmol) with 1.1 equivalents sodium methoxide solution at 60° C. for 6 hours gives, after work-up, Compound 4 as 2.57 g (98%) of a pale yellow liquid: $^1$H NMR (CDCl$_3$) 4.11 (s, 3H), 4.04 (s, 3H); $^{19}$F NMR (CDCl$_3$) 149.4 (d, 1 F), 149.7 (dd, 1 F), 156.9 (d, 1 F). Anal. calc. for C$_8$H$_6$NO$_4$F$_3$: C, 40.51; H, 2.55; N, 5.91. Found: C, 40.45; H, 2.68; N, 5.69.

General Method B

The nitro group of the fluoronitrobenzene is reduced by catalytic hydrogenation at 40 psi in ethanol/ethyl acetate over 10% Pd/carbon. Progress is monitored by TLC. When the reaction is complete, the catalyst is collected on a diatomaceous earth pad over a glass frit via filtration. The filtrate is concentrated in vacuo, giving the pure amine-substituted fluorinated benzene.

General Method C

The nitro group of the fluoronitrobenzene is reduced by homogeneous reduction in refluxing ethyl acetate/ethanol (2:1, 0.10 M) using stannous chloride dihydrate (5 equivalents). Reaction progress is monitored by TLC. The reaction solution is cooled, poured into water, and then neutralized to pH 7 by portionwise addition of 1 M sodium hydroxide with stirring. The resulting mixture is extracted twice with ethyl acetate. The extract is washed once with brine, dried over anhydrous sodium sulfate, and concentrated in vacuo. The resulting residue is then purified by flash chromatography.

Example 5

Preparation of 1-Amino-3,5-difluoro-2,4-dimethoxybenzene (5)

Using general method B, treatment of Compound 1 (10.9 g, 49.7 mmol) gives Compound 5 as 9.40 g (99.8%) of a clear, pale brown oil: $^1$H NMR (CDCl$_3$) 6.25 (dd, 1H), 3.89 (two s, 6H), 3.7 (br s, 2H); $^{19}$F NMR (CDCl$_3$) 135.5 (d, 1 F), 146.9 (s, 1 F). Anal. calc. for C$_8$H$_9$NO$_2$F$_2$: C, 50.80; H, 4.80; N, 7.40. Found: C, 50.61; H, 4.81; N, 7.26. The hydrochloride salt is obtained by treating a dioxane solution of 5 with 4 M HCl in dioxane, collecting the precipitate on a Büchner funnel, rinsing with dioxane, and drying in vacuo to give the hydrochloride salt of Compound 5 as a bone-white powder: m.p. 213–218° C. (dec.); $^1$H NMR (D$_2$O) 7.1 (br d, 1H), 4.05 (br s, 6H); $^{19}$F (D$_2$O) 131.1 (dd, 1 F), 141.6 (s, 1 F). Anal. calc. for C$_8$H$_{10}$NO$_2$F$_2$Cl: C, 42.59; H. 4.47; N, 6.21. Found: C, 42.75; H, 4.47; N, 6.14.

Example 6

Preparation of 1-Amino-2,4-dimethoxy-3-fluorobenzene (6)

Using general method C, treatment of Compound 2 (4.66 g, 23.2 mmol) gives Compound 6 as 3.67 g (92%) of a pale yellow oil: $^1$H NMR (CDCl$_3$) 6.52 (t, 1H), 6.40 (d, 1H), 3.92 (s, 3H), 3.80 (s, 3H); $^{19}$F NMR (CDCl$_3$) 152.9 (d). Anal. calc. for C$_8$H$_{10}$NO$_2$F: C, 56.14; H, 5.89; N, 8.18. Found: C, 56.14; H, 6.05; N, 8.03.

Example 7

Preparation of 1-Amino-2,4-dimethoxy-5-fluorobenzene (7)

Using general method B, treatment of Compound 3 (0.42 g, 2.1 mmol) gives Compound 7 as 0.38 g (100%) of a pale grey-brown oil that solidifies upon standing: m.p. 47–49° C.; $^1$H NMR (CDCl$_3$) 6.56 (s, 1H), 6.50 (d, 1H), 3.83 (s, 3M), 3.80 (s, 3H); $^{19}$F NMR (CDCl$_3$) 143.8 (m). Anal. calc. for C$_8$H$_{10}$NO$_2$F: C, 56.14; H, 5.89; N, 8.18. Found: C, 56.76; H, 6.04; N, 8.20.

Example 8

Preparation of 1-Amino-2,4-dimethoxy-3,5,6-trifluorobenzene (8)

Using general method C, treatment of Compound 4 (2.35 g, 9.91 mmol) gives Compound 8 as 1.06 g (52%) of a pale orange solid. This solid is dissolved in dioxane (8 mL) and treated at room temperature with 4 M HCl in dioxane (Aldrich, 4 mL). After five minutes, the precipitate is collected on a Büchner funnel and rinsed with dioxane (10 mL), followed by drying in vacuo over P$_2$O$_5$/NaOH, to give the hydrochloride salt of Compound 8 as 0.84 g of an off-white powder: m.p. 146–148° C.; $^1$H NMR (D$_2$O) 4.08 (s, 3H); 4.00 (s, 3H); $^{19}$F (D$_2$O) 149.6 (d, 1 F), 154.0 (dd, 1 F), 156.8 (d, 1 F). Anal. calc. for C$_8$H$_9$NO$_2$F$_3$Cl: C, 39.44; H, 3.77; N, 5.75. Found: C, 39.79; H, 3.70; N, 5.62.

General Method D

A solution or mixture of the desired aminofluorobenzene in water/conc. HCl (2:1, 0.3 M) is chilled in an ice bath, and treated with a cold solution of sodium nitrite (1.05 equivalents) in water. The resulting diazonium salt solution is stirred for 15 minutes, and then hypophosphorous acid (50% aqueous solution, Aldrich, 20 equivalents) is added over 5 minutes. The resulting mixture is stirred at room temperature for two hours, then diluted with water. The resulting mixture is neutralized with aqueous sodium carbonate or sodium hydroxide, and extracted twice with ether. The organic extract is washed once with water, once with brine, and dried over anhydrous sodium sulfate. The solution is concentrated in vacuo and the resulting residue is purified by flash chromatography.

Example 9

Preparation of 1,3-dimethoxy-2,4-difluorobenzene (9)

Using general method D, Compound 5 (0.566 g, 2.99 mmol) gives Compound 9 as 0.38 g (73%) of a clear, colorless liquid: $^1$H NMR (CDCl$_3$) 6.80 (td, 1H), 6.58 (m, 1H), 4.00 (s, 3H), 3.87 (s, 3H); $^{19}$F NMR(CDCl$_3$) 138.8 (d, 1 F), 150.1 (d, 1 F). Anal. calc. for C$_8$H$_8$O$_2$F$_2$: C, 55.19; H, 4.63. Found: C, 54.76; H, 4.63.

Alternatively, the diazonium cation is isolated as its hexafluorophosphate salt, followed by reduction with sodium borohydride. The method described in general method D is used to generate a diazonium salt in solution from Compound 5 (0.57 g, 3.0 mmol). A 60 wt % solution of hydrogen hexafluorophosphate (0.88 mL) is added over two minutes, giving a brown precipitate. After standing at ice-bath temperature for 10 minutes, the precipitate is collected on a Büchner funnel, rinsed with water, air dried, and then dried in vacuo over P$_2$O$_5$/NaOH to give 0.72 g (70%) of a pale brown powder: m.p. 69–72° C.; $^1$H NMR (CDCl$_3$) 8.00 (d, 1H), 4.42 (d, 3H), 4.38 (t, 3H); $^{19}$F NMR (CDCl$_3$) 128.5 (s, 1 F), 144.6 (s, 1 F). Anal. calc. for C$_8$H$_7$N$_2$O$_2$PF$_8$: C, 27.76; H, 2.04; N, 8.09. Found: C, 27.83; H, 1.94; N, 8.23. To a brown solution of this diazonium hexafluorophosphate (0.71 g, 2.1 mmol) in 10 mL methanol under air at room temperature is added sodium borohydride (0.11 g, 3.0 mmol) portionwise over three minutes, resulting in vigorous gas evolution. The resulting pale yellow-red mixture is partitioned between ethyl ether and aqueous citric acid (0.25 M). The organic layer is washed once with brine, dried over anhydrous sodium sulfate, and concentrated to a pale brown oil. Flash chromatography provides Compound 9 as 0.26 g (73%) of a clear colorless liquid.

Example 10

Preparation of 1,3-dimethoxy-2-fluorobenzene (10)

Using general method D, Compound 6 (1.10 g, 6.43 mmol) gives Compound 10 as 0.96 g (96%) of a clear pale yellow liquid: $^1$H NMR (CDCl$_3$) 6.95 (t, 1H), 6.59 (t, 2H), 3.89 (s, 6H); 19 F (CDCl$_3$) 159.2 (s). Anal. calc. for C$_8$H$_9$O$_2$F: C, 61.53; H, 5.81. Found: C, 61.36; H, 5.86.

Example 11

Preparation of 1,3-dimethoxy-4-fluorobenzene (11)

Using general method D, Compound 7 (0.35 g, 2.0 mmol) gives Compound 11 as 0.26 g (81%) of a clear colorless oil: $^1$H NMR (CDCl$_3$) 6.95 (dd, 1H), 6.52 (dd, 1H), 6.38 (dt, 1H), 3.85 (s, 3H), 3.74 (s, 3H); $^{19}$F NMR (CDCl$_3$) 146.0 (m). Anal. calc. for C$_8$H$_9$O$_2$F: C, 61.53; H, 5.81. Found: C, 61.26; H, 5.94.

Example 12

Preparation of 1,3-dimetboxy-2,4,5-trifluorobenzene (12)

Using general method D, Compound 8 (0.70 g, 2.9 mmol) gives Compound 12 as 0.44 g (80%) of a clear colorless oil: $^1$H NMR (CDCl$_3$) 6.51 (m, 1H), 4.07 (s, 3H), 3.83 (s, 3H); $^{19}$F (CDCl$_3$) 141.9 (dd, 1 F), 156.7 (t, 1 F), 163.4 (dd, 1 F). Anal. calc. for C$_8$H$_7$O$_2$F$_3$: C, 50.01; F 3.67. Found: C, 49.63; H, 3.69.

General Method E

A solution of the desired fluorinated dimethoxybenzene in dichloromethane (0.3 M, anhydrous) at room temperature under nitrogen is treated with boron tribromide solution (3.0 equivalents, 1.0 M in dichloromethane, Aldrich or Fluka) via syringe over five minutes. The reaction is monitored by TLC, and takes 24–48 hours to reach completion; an additional 0.5 equivalents of boron tribromide solution is sometimes necessary to drive the reaction to completion. The reaction mixture is carefully quenched with water, and the resulting mixture is stirred until all precipitate dissolves. The resulting solution is extracted twice with ether. The ether extract is washed twice with brine, dried over anhydrous sodium sulfate, and concentrated under reduced pressure and purified by sublimation to yield the desired fluorinated resorcinol.

Example 13

Preparation of 2,4-difluororesorcinol (13)

Using general method E, Compound 9 (0.64 g, 3.7 mmol) gives Compound 13 as 0.49 g (90%) of a colorless crystalline solid: m.p. 100–101° C.; $^1$H NMR (CDCl$_3$) 8.99 (s, 1H), 8.62 (s, 1H), 6.32 (td, 1H), 6.05 (m, 1H); $^{19}$F (CDCl$_3$) 145.4 (m, 1 F), 156.0 (m, 1 F). Anal. calc. for $C_6H_4O_2F_2$: C, 49.33; H, 2.76. Found: C, 48.96; H, 3.21; N, 0.028.

Example 14

Preparation of 2-fluororesorcinol (14)

Using general method E, Compound 10 (0.96 g, 6.1 mmol) gives Compound 14 as 0.75 g (95%) of a colorless crystalline solid: m.p. 114–116° C.; $^1$H NMR (CDCl$_3$) 8.52 (br s, 2H), 6.58 (m, 1H), 6.79 (t, 2H); $^{19}$F (CDCl$_3$) 162.3 (t). Anal. calc. for $C_6H_5O_2F \cdot 0.1H_2O$: C, 55.48; H, 4.03. Found: C, 55.05; H, 3.96.

Example 15

Preparation of 4-fluororesorcinol (15)

Using general method E, Compound 11 (27.4 g, 157.9 mmol) gives Compound 15 as 20.7 g (100%) of a colorless crystalline solid: m.p. 94–96° C.; $^1$H-NMR (d$_6$-DMSO) 8.39 (br, 1H), 8.00 (br, 1H), 6.89 (dd, 1H), 6.48 (dd, 1H), 6.27 (ddd, 1H). $^{19}$F-NMR (d$_6$-DMSO) 145.82 (m). Anal calc. for $C_6H_5FO_2$: C, 56.26; H, 3.93. Found: C, 56.23; H, 3.93.

Example 16

Preparation of 5-fluororesorcinol (16)

Using general method E, 3,5-dimethoxyfluorobenzene (5.0 g, 32.0 mmol, Aldrich) gives Compound 16 as 3.69 g (92%) of a colorless crystalline solid: m.p. 134–136° C.; $^1$H-NMR (d$_6$-DMSO) 9.60 (s, 2H), 6.05 (s, 1H), 5.97 (d, 2H). $^{19}$F-NMR (d$_6$-DMSO) 108.26 (t, J=11.1 Hz,). Anal. calc. for $C_6H_5FO_2$: C, 56.26; H, 3.93. Found: C, 56.33; H, 3.98.

Example 17

Preparation of 2,4,5-Trifluororesorcinol (17)

Using general method E, Compound 12 (0.42 g, 2.2 mmol) gives Compound 17 as 0.36 g (100%) of a white powder: m.p. 69–71° C.; $^1$H NMR (CDCl$_3$) 6.05 (m); $^{19}$F (CDCl$_3$) 144.4 (s, 1 F), 162.2 (s, 1 F); 169.7 (s, 1 F). Anal. calc. for $C_6H_3O_2F_3 \cdot H_2O$: C, 39.58; H, 2.77. Found: C, 39.58; H, 2.65.

Preparation of Fluorinated Aminophenols

General Method F

An excess of a secondary amine (3 equivalents) is added to a solution of fluorinated nitrobenzene in ethanol. If the amine is lower boiling than ethanol, this solution is heated in a sealed tube, otherwise the solution is heated at reflux (1–24 hours). The solution is evaporated to dryness and the resulting solid is purified by recrystallization from the appropriate solvent or by chromatography on silica gel to give the pure fluoronitroaniline. The desired fluorinated aminophenols are prepared using the same methodology employed in General Method A to prepare fluorinated resorcinols. For instance, dialkyl-substituted amine nucleophiles are substituted onto a perfluoronitrobenzene, in sequence with methoxide. The nitro group is then subjected to reduction, diazotization, followed by hydrodediazonization to yield a fluorinated aminophenol.

Example 18

Preparation of 4-dimethylamino-2,5-difluoronitrobenzene (18)

To a solution of 2,4,5-trifluoronitrobenzene (8.9 g, 50 mmol) in 100 mL ethanol is bubbled dimethylamine gas (6.8 g, 150 mmol). The solution is heated at 80° C. in a Parr pressure reactor for 6 hours. After evaporation of the solvent the product is chromatographed on silica gel/methylene chloride to give Compound 18.

Example 19

Preparation of 4-dimethylamino-5-fluoro-2-methoxynitrobenzene (19)

2.0 g (10 mmol) of 4-dimethylamino-2,5-difluoronitrobenzene (18) is treated with sodium methoxide according to general method F to give Compound 19 after chromatography on silica gel.

Example 20

Preparation of 4-dimethylamino-5-fluoro-2-methoxyaniline (20)

Using general method C, Compound 19 is converted to Compound 20.

Example 21

Preparation of N,N-dimethyl-2-fluoro-5-methoxyaniline (21)

Using general method D, the product from Example 20 is diazotized and reduced with sodium borohydride to give Compound 21.

Example 22

Preparation of 3-dimethylamino-4-fluorophenol (22)

The methyl ether of Example 21 is treated with boron tribromide using general method E to give Compound 22.

General Method G

Fluorinated aminophenols are generated from commercially available fluorinated phenyl ketones and aldehydes by nitrating the phenyl ketone or aldehyde and converting it into the corresponding nitrophenol using Baeyer-Villiger oxidation chemistry. Reduction followed by reductive amination then yields the N-substituted aminophenol.

Example 23

Preparation of 4-fluoro-3-nitrophenol (23)

To 15 mL of concentrated sulfuric acid at 0° C. is added 6.9 g (0.05 mmol) of 4-fluoroacetophenone. To the resulting solution is rapidly added a mixture of 4 mL nitric acid and 6 mL concentrated sulfuric acid. The reaction mixture is stirred at 0–5° C. for 3 hours. The reaction mixture is then poured into ice water, and the resulting mixture is extracted with chloroform. The combined organic fractions are washed with water, dried over anhydrous sodium sulfate, filtered and concentrated under reduced pressure. The resulting residue is purified using column chromatography on silica gel, eluting with 20% ethyl acetate/hexanes, yielding 6.0 g of 4-fluoro-3-nitroacetophenone (60% yield).

Concentrated sulfuric acid (200 mL) and acetic acid (120) mL are mixed at 0° C. To this solution is added 15 g (0.082 mol) of 4-fluoro-3-nitroacetophenone with stirring. To the cold reaction mixture is added 36 mL of 36% peracetic acid. The reaction mixture is then stirred at room temperature for 4 hours. Water (500 mL) is added to the mixture, and the crude product is extracted into diethyl ether. The combined ether fractions are washed with water, dried over anhydrous sodium sulfate, filtered and concentrated under reduced pressure. The residue is purified using column chromatography on silica gel, eluting with 3% methanol/chloroform, giving 3.2 g of Compound 23 (20% yield). mp: 86–87° C. $^1$H-NMR (CDCl$_3$) 7.56 (dd, 1H); 7.29 (t, 1H), 7.12 (m, 1H); 5.36 (s, 1H). $^{19}$F-NMR (d$_6$-DMSO) 147.60 (s). Anal. calc. for C$_6$H$_4$FNO$_3$: C, 45.87; H, 2.57; N, 8.92. Found: C, 45.80; H. 2.51; N, 8.69.

Example 24

Preparation of 3-amino-4-fluorophenol (24)

A mixture of 4-fluoro-3-nitrophenol (2.70 g, 17.2 mmol) and palladium on charcoal (10%, 0.31 g) in 60 mL ethyl acetate is hydrogenated under 50 psi of H$_2$ using a Parr hydrogenation reactor. After shaking for 1 hour, the reaction mixture is filtered using a diatomaceous earth pad to remove catalyst. The filtrate is concentrated in vacuo, and the residue is sublimed to yield 2.18 g (100%) of Compound 24 as a white solid. MP: 142–144° C. $^1$H-NMR (d$_6$-DMSO) 8.82 (s, 1H); 6.70 (dd, 1H); 6.17 (dd, 1H); 5.85 (m, 1H); 4.92 (s, 2H). $^{19}$F-NMR (d$_6$-DMSO) 142.78 (t, 13.0 Hz). Anal. calc. for C$_6$H$_6$FNO: C, 56.69; H, 4.76; N, 11.02. Found: C, 57.28; H, 4.86; N, 10.65.

Example 25

Alternate Preparation of 3-dimethoxyamino-4-fluorophenol (22)

Sodium cyanoborohydride (0.81 g, 12.7 mmol) is added to a solution of 3-amino-4-fluorophenol (0.66 g, 4.6 mmol), formaldehyde (37% solution, 2.0 g, 24.6 mmol) and acetic acid (0.5 mL) in 20 mL acetonitrile. The reaction is stirred for 2 hour and then poured into 100 mL water. The product is then extracted into diethyl ether (50 mL×3) and the combined organic fractions are washed with brine (40 mL), and dried over anhydrous sodium sulfate. The resulting solution is concentrated in vacuo, and the residue is chromatographed on silica gel using CHCl$_3$:ethyl acetate as eluant (99:1 to 90:10 gradient) to yield 0.72 g (91%) of Compound 22 as a brown solid. $^1$H-NMR (CDCl$_3$) 6.85 (dd, 1H); 6.40 (m, 1H); 6.27 (m, 1H); 2.84 (s, 6H). $^{19}$F-NMR (CDCl$_3$) 133.25 (t, J=9.5 Hz).
Preparation of Fluorinated Fluoresceins
  General Method H
  The desired fluorinated resorcinol (2 equivalents), the desired phthalic anhydride (1 equivalents) and anhydrous zinc chloride (2.5 equivalents) are fused at ca. 170–180° C. for 30 minutes with manual stirring. The cooled mixture is suspended in water, followed by filtration. The retentate, containing the fluorinated fluorescein, is further purified by either 1) dissolving in methanol/water, followed by filtration through a diatomaceous earth pad and concentration, or by 2) conversion into the diacetate by dissolving the retentate in acetic anhydride and pyridine, heating briefly, then subjecting the resulting mixture to aqueous workup and flash chromatographic purification or recrystallization of the organic-soluble product(s).
  General Method I
  Alternatively, the desired fluorinated resorcinol (2 eq) and the desired phthalic anhydride (1 eq) are heated in methanesulfonic acid, as 10% w/v solution, at 80–85° C. for 48 hours with stirring. The cooled solution is then poured into 7 volumes of an ice/water mixture. The resulting precipitate is collected, washed with cold water, dried in vacuo at 60° C., and further purified as described above.

Example 26

Preparation of 4,5,6,7-tetrafluorofluorescein diacetate (25)

General method H using 3,4,5,6-tetrafluorophthalic anhydride and resorcinol (24.0 g, 218 mmol, Aldrich) gives a brick red solid (45.1 g) after drying at 60° C. for 24 hours. The solid is then treated with acetic anhydride and pyridine to yield the crude product, which is recrystallized from ethyl acetate/hexane to yield Compound 25 as 43.1 g (81%, two crops) of a colorless crystalline solid. $^1$H-NMR (CDCl$_3$) 7.15 (s, 2H), 6.99 (d, 2H), 6.92 (d, 2H), 2.31 (s, 6H). $^{19}$F-NMR (CDCl$_3$) 137.26 (m, 1 F), 140.79 (m, 1 F), 141.21 (m, 1 F), 148.97 (m, 1 F). Anal. calc. for C$_{24}$H$_{12}$F$_4$O7: C, 59.03; H, 2,48. Found: C, 59.00; H, 2.69.

Example 27

Preparation of 2',4,5,6,7,7'-hexafluorofluorescein (26)

Using general method I, Compound 15 (7.0 g, 54.6 mmol) and 3,4,5,6-tetrafluorophthalic anhydride (6.05 g, 27.5 mmol) gives metallic red needle crystals that are collected, washed with cold water, and dried in vacuo at 60° C. for 24 hours to yield 10.0 g (83%) of Compound 26. $^1$H-NMR (d$_6$-DMSO) 7.13 (d, 2H), 6.87 (d, 2H). $^{19}$F-NMR (d$_6$-DMSO) 134.73 (m, 2 F), 135.29 (m, 1 F), 139.96 (br, 2 F), 148.01 (t, 1 F).

Example 28

Preparation of 2',4,5,6,7,7'-hexafluorofluorescein diacetate (27)

Following general method H, Compound 27 is obtained from Compound 26 in 90% yield. $^1$H-NMR (CDCl$_3$) 7.17 (d, 2H), 6.76 (d, 2H), 2.38 (s, 6H). $^{19}$F-NMR (CDCl$_3$) 130.87 (t, J=8.5 Hz, 2 F), 136.09 (m, 1 F), 1139.75 (m, 1 F), 141.05 (t, J=20.8 Hz, 1 F), 147.77 (t, J=20.3, 1 F).

Example 29

Preparation of 2',7'-dichloro-4,5,6,7-tetrafluorofluorescein diacetate (28)

Following general method H, Compound 28 is obtained in 85% overall yield from the reaction of 4-chlororesorcinol and 3,4,5,6-tetrafluorophthalic anhydride, followed by subsequent reaction with acetic anhydride and pyridine.

¹H-NMR (CDCl₃) 7.19 (s, 2H), 7.05 (s, 2H), 2.39 (s, 6H). ¹⁹F-NMR (CDCl₃) 135.94 (m, 1 F, 139.47 (m, 1 F), 140.89 (t, J=19.9 Hz, 1 F), 147.65 (t, J=19.2 Hz, 1 F).

Example 30

Preparation of 2',7'-difluorofluorescein (29)

Following general method H, Compound 29 is obtained from Compound 15 and phthalic anhydride in 85% yield. ¹H-NMR (d₆-DMSO) 7.99 (d, 1H), 7.79 (t, 1H), 7.72 (t, 1H), 7.29 (d, 1H), 6.89 (d, 2H), 6.48 (d, 2H).

Example 31

Preparation of 2',7'-difluoro-5-(and-6)-nitrofluorescein diacetate (30)

Following general method H, Compound 30 is obtained in 78% yield from the reaction of Compound 15 and 4-nitrophthalic acid, followed by subsequent reaction with acetic anhydride and pyridine. The isomers were partially resolved fractional crystallization (as described below for general method H). The 5-nitro isomer: ¹H-NMR (d₆-DMSO) 8.69 (s, 1H), 8.61 (d, 1H), 7.80 (d, 1H), 7.55 (d, 2H), 7.16 (d, 2H), 2.35 (s, 6H). ¹⁹F-NMR (d₆-DMSO) 128.11 (t, J=8.5). The 6-nitro isomer: ¹H-NMR (d₆-DMSO) 8.53 (d, 1H), 8.46 (s, 1H), 8.28 (d, 1H), 7.53 (d, 2H), 7.10 (d, 2H), 2.35 (s, 6H). ¹⁹F-NMR (d₆-DMSO) 128.29 (t, J=8.3).

Example 32

Preparation of 2',4',5',7'-tetrabromo-4,5,6,7-tetrafluorofluorescein diacetate (31)

Bromine (40.0 g, 250 mmol) is added dropwise to a solution of Compound 34 (14.3 g, 35.4 mmol) in 70 mL methanol. The reaction mixture is stirred for 3 hours and concentrated in vacuo. The resulting residue is stirred with acetic anhydride and pyridine for 1 hour, then diluted with ethyl acetate. The solution is washed with 1 M citric acid solution, then brine, then dried, and concentrated in vacuo. The resulting residue is purified using column chromatography to yield 24.2 g (85%) of Compound 31. ¹H-NMR (CDCl₃) 7.20 (s, 2H), 2.45 (s, 6H). ¹⁹F-NMR (CDCl₃) 135.17 (m, 1 F), 138.59 (br, 1 F), 139.99 (br, 1 F), 146.80 (m, 1 F).

General Method J

Isolation of isomers: A mixture of the desired fluorinated carboxyfluorescein (1 equivalent), pyridine (4 equivalents), and acetic anhydride (100 equivalents) is heated for 5 minutes at 80° C. The reaction is cooled to 20° C. and placed in freezer (−4° C.) for 24 hours. The resulting crystalline precipitate (the pyridinium salt of the 6-isomer diacetate) is collected, washed with acetic anhydride, ether, and dried in vacuo to yield an off-white powder. The filtrate is stirred with an equal volume of water for 30 minutes and extracted twice with ethyl acetate. The combined extract is washed with brine, dried, concentrated in vacuo, and recrystallized from CH₂Cl₂ to yield the 5-isomer diacetate as the free acid. The filtrate is concentrated in vacuo, redissolved in toluene, 1.5 equivalents of pyridine is added, and the solution is allowed to stand at 20° C. for 15 hours. The resulting precipitate is collected, washed with toluene, ether, and dried in vacuo to yield a second crop of the 6-isomer diacetate as the pyridinium salt. The filtrate (mother liquor) is diluted with an equal volume of ethyl acetate, washed twice with 1 M citric acid, brine, dried, concentrated in vacuo, and recrystallized from CH₂Cl₂ to yield a second crop of the 5-isomer diacetate as the free acid. The above alternative recrystallization cycle is repeated two additional times to isolate more product from the mother liquor.

Example 33

Preparation of 6-carboxy-2',7'-difluorofluorescein diacetate, pyridinium salt (32)

Using general method H followed by J, Compound 15 (10.0 g, 78.0 mmol) and trimellitic acid anhydride gives Compound 32, which is crystallized from the reaction mixture and toluene to yield 10.02 g (44%, 4 crops) of an off-white solid. ¹H-NMR (CDCl₃) 8.67 (m, 2H), 8.41 (d, 1H), 8.13 (d, 1H), 7.94 (s, 1H), 7.82 (t, 1H), 7.41 (m, 2H), 7.17 (d, 2H), 6.60 (d, 2H), 2.45 (s, 6H). ¹⁹F-NMR (CDCl₃) 131.73 (dd). Anal. Calc. for C₃₀H₁₉F₂NO₉: C, 62.61; H, 3.33; N, 243. Found: C, 62.01; H, 3.25; N, 2.37.

Example 34

Preparation of 5-carboxy-2',7'-difluorofluorescein diacetate (33)

Using general method H followed by J, Compound 15 (10.0 g, 78.0 mmol) and trimellitic acid anhydride gives Compound 33, which is recrystallized from CH₂Cl₂ to yield 9.30 g, (48%, 4 crops) of an off-white solid. ¹H-NMR (CDCl₃) 8.80 (s, 1H), 8.47 (d, 1H), 7.35 (d, 1H), 7.20 (d, 2H), 6.09 (d, 2H), 2.30 (s, 6H). ¹⁹F-NMR (CDCl₃) 131.44 (br). Anal. calc. for C₂₅H₁₄F₂O₉: C, 61.18; H, 2.44. Found: C, 59.57; H, 2.53.

General Method K

Hydrolysis of a fluorinated fluorescein diacetate: A 0.1 M solution of diacetate in THF/MeOH/water (4:4:2) is treated with NH₄OH (10 eq) at 20° C. The reaction is stirred for 2 hours and poured into 7 volume of ice water and acidified with 36% HCl to pH 2. The precipitate is collected, washed with cold water, and dried at 60° C. for 15 hours to yield the desired product.

Example 35

Preparation of 4,5,6,7-tetrafluorofluorescein (34)

Following general method K, treatment of Compound 25 (12.0 g, 24.6 mmol) gives Compound 34 as 8.95 g (90%) of an orange powder. ¹H-NMR (d₆-DMSO) 7.00 (d, 2H), 6.70 (d, 2H), 6.60 (dd, 2H). ¹⁹F-NMR (d₆-DMSO) 135.70 (m, 1 F), 139.70 (m, 2 F), 147.59 (t, 1 F). Anal. calc. for C₂₀H₈F₄O₅: C, 59.42; H, 1.99. Found: C, 59.39; H, 1.99.

Example 36

Preparation of 6-carboxy-2',7'-difluorofluorescein (35)

Following general method K, treatment of Compound 32 (1.2 g, 2.1 mmol) gives Compound 35 as 0.79 g (92%) of an orange powder. ¹H-NMR (d₆-DMSO) 8.25 (d, 1H), 8.10 (d, 1H), 7.70 (s, 1H), 6.89 (d, 2H), 6.58 (d, 2H). ¹⁹F-NMR (d₆-DMSO) 135.20 (dd).

Example 37

Preparation of 5-carboxy-2',7'-difluorofluorescein (36)

Following general method K, treatment of Compound 33 (1.0 g, 2.0 mmol) gives Compound 36 as 0.68 g (83%) of an orange powder. $^1$H-NMR (d$_6$-DMSO) 8.40 (s, 1H), 8.28 (d, 1H), 7.40 (d, 1H), 6.88 (d, 2H), 6.62 (d, 2H). $^{19}$F-NMR (d$_6$-DMSO) 135.24 (dd).

Example 38

Preparation of 2',7'-dichloro-4,5,6,7-tetrafluorofluorescein (37)

Following general method K, treatment of Compound 28 (0.60 g, 1.07 mmol) gives Compound 37 as 0.43 g (85%) of an orange powder. $^1$H-NMR (d$_6$-DMSO) 7.33 (s, 2H), 6.90 (s, 2H). $^{19}$F-NMR (d$_6$-DMSO) 134.83 (m, 1 F), 139.43 (br, 1 F), 140.22 (t, J=19.4 Hz, 1 F), 147.62 (t, J=20.3 Hz, 1 F).

Example 39

Preparation of 2',7'-difluoro-5-(and-6)-nitrofluorescein (38)

Following general method K, treatment of Compound 30 gives Compound 38 as an orange powder in 92% yield.

Example 40

Preparation of 2',4',5',7'-tetrabromo-4,5,6,7-tetrafluorofluorescein (39)

Following general method K, treatment of Compound 31 gives Compound 39 as an orange powder in 92% yield. $^1$H-NMR (d$_6$-DMSO) 7.58 (s). $^{19}$F-NMR (DMSO-d$_6$) 134.34 (br, 1 F), 138.76 (br, 1 F), 139.73 (br, 1 F), 147.11 (br, 1 F). HRMS (H$^+$ abs) Calc. for C$_{20}$H$_5$Br$_4$F$_4$O$_5$: 720.6764; Found: 720.6769.

Example 41

Preparation of 5-(and-6)-carboxy-2',4',5',7'-tetrafluorofluorescein (40)

Following general method H, treatment of Compound 13 (0.65 g, 4.3 mmol) gives Compound 40 as 0.20 g (24%) of a dark brown powder. One purification via the methanol/water dissolution-filtration cycle gives a brown powder: R$_f$=0.22 (CHCl$_3$:methanol:acetic acid, 20:4:1); UV max (pH 8.5 phosphate buffer) 510 nm ($\epsilon$=78,100 cm$^{-1}$M$^{-1}$); emission maximum 533 nm. The diacetate is prepared as a non-fluorescent reddish-orange powder: R$_f$=0.50 (CHCl$_3$:methanol:acetic acid, 20:4:1); $^1$H NMR (d$_6$-DMSO) 8.4–7.6 (m, 3H), 7.05 (two dd, 2H), 2.4 (two s, 6H); $^{19}$F (d$_6$-DMSO) 125.6 (d); 125.7 (d); 140.0 (s); 140.1 (s); Anal. calc. for C$_{21}$H$_8$O$_7$F$_4$.H$_2$O: C, 54.09; H 2.16; N, 0.0. Found: C, 54.58; H, 2.31; N, 0.13.

Example 42

Preparation of 5-(and-6)-carboxy-4',5'-difluorofluorescein (41)

Following general method H, treatment of Compound 14 (0.35 g, 2.7 mmol) and trimellitic acid anhydride gives Compound 41 as 0.42 g (82%) of a brown powder. One purification cycle via the methanol/water dissolution-filtration method gives a reddish-brown powder: R$_f$=0.28 (CHCl$_3$:methanol:acetic acid, 20:4:1); UV max (pH 8.5 phosphate buffer) 511 nm ($\epsilon$=67,000 cm$^{-1}$M$^{-1}$); emission maximum 534 nm. $^1$H NMR (CD$_3$OD) 8.6 (s); 8.4 (dd); 8.3 (dd); 8.05 (t); 7.8 (s); 7.3 (d); 8.6–7.3 (m, 3H); 6.7 (t, 2H); 6.4 (m, 2H). Anal. calc. for C$_{21}$H$_{10}$O$_7$F$_2$.1.5H$_2$O: C, 57.41; H, 2.98; N, 0.0. Found: C, 57.70; H. 2.88; N, 0.13.

The diacetate is prepared as a non-fluorescent red-orange powder: R$_f$=0.54 (CHCl$_3$:methanol:acetic acid, 20:4:1); $^1$H NMR (CDCl$_3$) 8.7 (s); 8.4 (dd), 8.1 (d), 7.9 (s), 7.3 (d); 6.9 (m), 6.6 (m), 2.4 (s); $^{19}$F (CDCl$_3$) 145.9 (dd, 1 F), 146.2 (m, 1 F). Anal. calc. for C$_{25}$H$_{19}$O$_9$F$_2$.2H$_2$O: C, 56.40; H, 3.41; N, 0.0. Found: C, 56.90; H, 3.19; N, 0.20.

Example 43

Preparation of 2',4,4',5,5',6,7,7'-octafluorofluorescein (42)

General method H is modified to substitute 3,4,5,6-tetrafluorophthalic anhydride for trimellitic anhydride. Using Compound 13 as starting material (0.10 g, 0.68 mmol), Compound 42 is obtained as 0.04 g (25%) of a black powder. One purification cycle via the methanol/water dissolution-filtration scheme gives an orange-red powder: R$_f$=0.14 (CHCl$_3$:methanol:acetic acid, 20:4:1); UV max (methanol) 535 nm; emission maximum 553 nm.

Preparation of 1',8'-Substituted Fluorinated Fluoresceins:

Example 44

Preparation of 2,4-dimethoxy-3,5,6-trifluorobenzonitrile (43)

A solution of sodium methoxide (18 g, 83 mmol, 25% in methanol) is added dropwise to a solution of pentafluorobenzonitrile (7.72 g, 40 mmol) in 60 mL methanol over 15 min. The reaction is heated to reflux for 3 hours, cooled to room temperature and then poured into 150 mL ice water. The product is then extracted with diethyl ether (100 mL×2), and the combined organic layers are washed with brine (50 mL), dried over magnesium sulfate and concentrated in vacuo. The residue is then chromatographed on silica gel, eluting with hexane:ethyl acetate (97:3 to 88:12 gradient) to yield 6.18 g (71%) of Compound 43 as a colorless oil. $^1$H-NMR (CDCl$_3$) 4.16 (s, 3H); 4.10 (s, 3H). $^{19}$F-NMR (CDCl$_3$) 134.39 (dd, J=10.1 and 20.3 Hz, 1 F); 150.80 (d, J=7.1 Hz, 1 F); 158.00 (d, J=21.4 Hz, 1 F). Anal. calc. for C$_9$H$_6$F$_3$NO$_2$: C, 49.78; H, 2.78; N, 6.45. Found: C, 49.71; H, 2.78; N, 6.56. A second product, 3,5-difluoro-2,4,6-trimethoxybenzonitrile, is also isolated from the reaction mixture as a colorless solid (1.09 g; 12%). $^1$H-NMR (CDCl$_3$) 4.12 (s, 3H); 4.07 (s, 6H). $^{19}$F-NMR (CDCl$_3$) 152.11 (s).

Example 45

Preparation of the imine of 2,4-dimethoxy-2',3,3',4',5,5',6,6'-octafluorobenzophenone (44)

Pentafluorophenylmagnesium chloride is prepared according to literature procedure (Brewer et al. J. CHEM. SOC. (C), 664 (1968)) and added to a solution of Compound 43 (2.17 g, 10 mmol) in 15 mL of diethyl ether at 20° C. The reaction mixture is heated for 15 hours under reflux. After cooling, the reaction mixture is poured into 3% citric acid and extracted with diethyl ether. The combined organic layers are washed with brine, dried over magnesium sulfate and concentrated in vacuo. The residue is purified by silica gel column chromatography eluting with CHCl$_3$:hexane (70:30 to 100:0 gradient) to yield 1.54 g (40%) of the imine, Compound 44. $^1$H-NMR (d$_6$-DMSO) 4.05 (s, 3H); 3.67 (s, 3H). $^{19}$F-NMR (d$_6$-DMSO) 138.24 (dd, J=5.6, 23.4 Hz, 0.8 F); 139.34 (dd, J=6.2, 23.7 Hz, 1.2 F); 140.16 (dd, J=9.8, 23.4 Hz, 0.6 F); 141.10 (dd, J=9.6, 22.9 Hz, 0.4 F); 145.90 (dd, J=9.6, 54.2 Hz, 1 F); 148.15 (m, 1 F); 154.18 (dd, J=22.8, 93.5 Hz, 1 F); 157.28 (m, 2 F). Anal. calc. for $C_{15}H_7F_8NO_2$: C, 46.77; H, 1.83; N, 3.64. Found: C, 46.65; H, 1.84; N, 3.54.

Example 46

Preparation of 2,4-dimethoxy-2',3,3',4',5,5',6,6'-octafluorobenzophenone (45)

Hydrochloric acid (1 mL, 36%) is added to a solution of Compound 44 (0.77 g, 2 mmol) in 7 mL isopropyl alcohol and 10 mL water. The reaction is heated for 3 hours at reflux. The reaction mixture is then poured into 50 mL ice water and extracted with ether (50 mL×2). The combined organic fractions are washed with brine (40 mL), dried over magnesium sulfate and concentrated in vacuo. The residue is then sublimed to yield 0.70 g (90%) of Compound 45 as colorless crystals. mp: 49–50° C. $^1$H-NMR (CDCl$_3$) 4.17 (s, 3H); 3.83 (s, 3H). $^{19}$F-NMR (CDCl$_3$) 142.02 (m, 2 F); 143.87 (dd, J=9.9, 23.4 Hz, 1 F); 148.39 (t, J=20.3 Hz, 1 F); 150.54 (d, J=9.6 Hz, 1 F); 158.02 (d, J=22.0 Hz, 1 F); 160.47 (m, 2 F). Anal. calc. for $C_{15}H_6F_8O_3$: C, 46.65; H, 1.57. Found: C, 46.43; H, 1.58.

Example 47

2,4-dihydroxy-2', 3,3',4',5,5',6,6'-octafluorobenzopbenone (46)

A solution of Compound 45 (450 mg, 1.17 mmol) in 5 mL acetic acid and 5 mL 48% hydrobromic acid is heated for 48 hours at reflux. The reaction mixture is worked up as above, and the crude product is purified by column chromatography to yield 362 mg (87%) of Compound 46 as a colorless solid. $^{19}$F-NMR (d$_6$-DMSO) 139.80 (m, 1 F); 141.69 (dd, J=10.0, 20.1 Hz, 1 F); 143.05 (dt, J=5.8, 23.1 Hz, 1 F); 155.48 (dd, J=10.2, 22.8 Hz, 1 F); 155.67 (s, 1 F); 156.27 (dd, J=5.8, 20.5 Hz, 1 F); 158.57 (t, J=22.2 Hz, 1 F); 162.5 (b, 1 F).

Example 48

3-Methoxy-6-hydroxy-1,2,4,5,6,7,8,-hexafluoroxanthone (47)

A solution of sodium hydroxide (125 mg, 3.14 mmol) in 5 mL methanol is added dropwise to a solution of Compound 46 (450 mg, 1.25 mmol) in 10 mL methanol. The reaction mixture is then heated at reflux for 15 hours. The reaction mixture is then poured into 50 mL water and hydrochloric acid is added to a solution pH of 2, and the resulting solution is extracted with ethyl acetate (50 mL×2). The combined organic layers are washed with brine (30 mL), dried over magnesium sulfate and concentrated in vacuo to yield 387 mg (88%) of crude Compound 47. An analytically pure sample is obtained by recrystallization from isopropyl alcohol. mp: 270–272° C. dec. $^1$H-NMR (d$_6$-DMSO) 4.23 (s). $^{19}$F-NMR (d$_6$-DMSO) 141.39 (dd, J=13.0, 20.3 Hz, 1 F); 141.85 (dd, J=11.4, 21.6 Hz, 1 F); 151.65 (d, J=10.4 Hz, 1 F); 154.34 (d, J=20.3 Hz, 1 F); 155.46 (t, J=7.9 Hz, 1 F); 156.68 (dd, 6.4, 20.3 Hz, 1 F). Anal. calc. for $C_{14}H_4F_6O_4$: C, 48.02; H, 1.15. Found: C, 47.09; H, 1.07.

Example 49

Preparation of 3-methoxy-6-(2-methoxyethoxymethoxy)-1,2,4,5,7,8-hexafluoroxanthone (48)

Methoxyethoxymethyl chloride (150 mg, 1.2 mmol) is added to a solution of Compound 47 in 10 mL dry $CH_2Cl_2$ at 20° C. The reaction mixture is stirred for 1 hour and poured into 50 mL water. The product is extracted with diethyl ether (30 mL×2) and ethyl acetate (30 mL). The combined organic extracts are washed with 5% citric acid solution (50 mL), and brine (30 mL), dried over anhydrous magnesium sulfate and concentrated in vacuo to yield 425 mg yellow oil. The crude oil is then recrystallized from isopropyl alcohol to yield 240 mg (51%) of Compound 48 as a colorless solid. $^1$H-NMR (d$_6$-DMSO) 5.48 (s, 2H); 4.36 (s, 3H); 3.99 (t, J=Hz, 2H); 3.58 (t, J=Hz, 2H); 3.36 (s, 3H). $^{19}$F-NMR (d$_6$-DMSO) 142.90 (d, J=12.7, 1 F); 142.97 (d, J=12.4 Hz, 1 F); 153.12 (d, J=13.5 Hz, 1 F); 155.54 (d, J=19.7 Hz, 1 F); 155.82 (d, J=11.3 Hz, 1 F); 157.13 (d, J=19.5 Hz, 1 F).

Example 50

Preparation of 1,2,4,5,7,8-hexafluoro-3-hydroxy-6-methoxy-9-pentafluorophenylxanthen-9-ol (49)

Pentafluorophenylmagnesium chloride (3 mmol, prepared as in Example 45) in 10 mL diethyl ether is added to a solution of Compound 48 in 10 mL dry THF at 20° C. The reaction is then heated at reflux for 5 hours, during which time an additional 2 mmol pentafluorophenylmagnesium chloride is added. The reaction mixture is extracted and dried as in Example 49 to yield 450 mg of the crude product. The product is then purified by column chromatography on silica gel, using CHCl$_3$:methanol (100:0 to 95:5 gradient) as eluant to yield 176 mg (72%) of Compound 49. $^1$H-NMR (d$_6$-DMSO) 4.08 (s). $^{19}$F-NMR (d$_6$-DMSO) 136.21 (d, J=22.6 Hz, 2 F); 139.33 (dd, J=8.0, 22.8 Hz, 1 F); 140.64 (dd, J=6.9, 22.1 Hz, 1 F); 150.26 (t, J=22.5 Hz, 1 F); 152.2 (d, J=9.3 Hz, 1 F); 154.32 (d, J=22.9 Hz, 1 F); 156.06 (s, 1 F); 157.13 (d, J=24.8 Hz, 1 F); 158.47 (t, J=23.4 Hz, 2 F).

Example 51

Preparation of 1,2,4,5,7,8-hexafluoro-6-hydroxy-9-pentafluorophenylxanthen-3-one (50)

A hydrobromic acid solution (49%, 2 mL) is added to a solution of Compound 49 (155 mg, 0.31 mmol) in 2 mL acetic acid at 20° C. The reaction mixture is heated to 110° C. for 1.5 hours and then poured into 30 mL ice water. The product is extracted with diethyl ether (20 mL×3), and the combined organic layers are washed with brine (20 mL), dried over magnesium sulfate, and concentrated in vacuo. The residue is then chromatographed on silica gel using CHCl$_3$:methanol as eluant (99:5 to 85:5 gradient) to yield Compound 50 as 125 mg (81%) of an orange solid. $^{19}$F-NMR (d$_6$-DMSO) 136.79 (d, J=20.9 Hz, 2 F); 141.75 (d, J=19.8 Hz, 2 F); 146.70 (t, J=22.4 Hz, 1 F); 152.60 (t, J=15.2 Hz, 2 F); 157.12 (dt, J=6.3, 20.6 Hz, 2 F); 159.09 (d, J=8.7 Hz, 2 F).

Preparation of Fluorinated Rhodols:

General Method L

Equimolar mixtures of the two appropriate electron rich aromatic components (i.e. a resorcinol, and a 3-aminophenol) are condensed with one equivalent of a phthalic acid or phthalic anhydride, either a) as a melt at 150–200° C. in the presence of one equivalent of anhydrous zinc chloride, with subsequent work-up consisting of mixing with water, followed by filtration, or b) as a solution in warm (80° C.) methanesulfonic acid, with subsequent work-up consisting of pouring the reaction solution into an excess of water, followed by filtration. In both methods the desired unsymmetrical fluorescein and rhodol dye products are separated from the undesired symmetrical dye products by either flash chromatography or preparative thin-layer chromatography. For analytical thin-layer chromatography, solvents used are $CHCl_3$:methanol:acetic acid in proportions: A 20:4:1; B 50:5:1; C 15:3:1. TLC solvent D is 0.5% acetic acid/THF.

Example 52

Preparation of 2'-fluoro-N,N-dimethylrhodol (51)

Using general method L-a), 4-fluororesorcinol (15, 0.20 g, 1.6 mmol), m-dimethylaminophenol (0.214 g, 1.56 mmol), phthalic anhydride (0.23 g, 1.6 mmol) and anhydrous zinc chloride (0.21 g, 1.6 mmol) gives the crude product as 0.38 g of a red powder. A portion is purified to give Compound 51 as a red powder: $R_f$=0.45 (TLC solvent A). $^1H$ NMR ($d_6$-DMSO) 8.0 (m, 1H); 7.75 (m, 1H); 7.5 (m, 1H); 7.25 (m, 1H); 6.85 (t, 1H); 6.6 (m, 2H); 6.45 (d, 1H); 6.38 (d, 1H); 3.0 (s, 6H). $^{19}F$ NMR ($d_6$-DMSO) 144.4 (s). Excitation max 519 nm; Emission max 553 nm (methanol). pKa 4.2.

Example 53

Preparation of 7'-fluororhodol (52)

Using general method L-a), resorcinol (154 mg, 1.4 mmol), 3-amino-4-fluorophenol (24, 0.20 g, 1.4 mmol) and phthalic anhydride (207 mg, 1.4 mmol) gives the crude product as 0.43 g of a brick-red powder. A portion is purified to give Compound 52 as an amber powder: $R_f$=0.45 (TLC solvent A). $^1H$ NMR ($CD_3OD$) 8.0 (d, 1H); 7.77 (t, 1H); 7.71 (t, 1H); 7.21 (d, 1H); 6.70 (d, 1H); 6.65 (s, 1H); 6.59 (m, 2H); 6.25 (d, 1H). $^{19}F$ NMR ($CD_3OD$) 137.5 (br s). Excitation max 494 nm; Emission max 519 nm (methanol). pKa 5.2.

Example 54

Preparation of N,N-dimethyl-7'-fluororhodol (53)

Using general method L-a), resorcinol (213 mg, 1.9 mmol), 3-dimethylamino-4-fluorophenol (22, 0.30 g, 1.9 mmol) and phthalic anhydride (281 mg, 1.9 mmol) gives the crude product as 0.51 g of a red-brown powder. A portion is purified to give Compound 53 as red powder: $R_f$=0.65 (TLC solvent A). $^1H$ NMR ($CD_3OD$) 8.05 (d, 1H); 7.7 (m, 2H); 7.2 (d, 1H); 6.80 (d, 1H); 6.4 (m, 2H); 6.3 (m, 2H); 2.8 (s, 6H). $^{19}F$ NMR ($CD_3OD$) 132.8 (m). Excitation max 520 nm, emission max 546 nm (pH 9). pKa 5.3.

Example 55

Preparation of 2'-fluororhodol (54)

Using general method L-a), 4-fluororesorcinol (15, 0.30 g, 2.3 mmol), 3-aminophenol (256 mg, 2.34 mmol), and phthalic anhydride (347 mg, 2.34 mmol) gives crude product as 0.56 g of an orange-brown powder. A portion is purified to give Compound 54 as an amber powder. $R_f$=0.25 (TLC solvent A). $^1H$ NMR ($CD_3OD$) 7.7 (m, 3H); 7.3 (m, 1H); 6.95 (m, 1H); 6.7 (m, 4H). $^{19}F$ NMR ($CD_3OD$) 129.6 (m). Excitation max 495; Emission max 518 nm (methanol). pKa 3.8.

Example 56

Preparation of 5-(and-6)-carboxy-2'-fluororhodol (55)

Using method L-a), 4-fluororesorcinol (15, 0.30 g, 2.3 mmol), 3-aminophenol (256 mg, 2.34 mmol), and trimellitic anhydride (450 mg, 2.34 mmol) gives crude Compound 55 as 0.57 g of a brick-red powder: $R_f$=0.16 (TLC solvent C).

Preparation of Fluorinated Xanthenes

Example 57

Preparation of 2,7-difluoro-6-hydroxy-9-trifluoromethylxanthene-3-one (56)

4-Fluororesorcinol (Compound 15, 0.10 g, 0.78 mmol) is condensed with trifluoroacetic acid (45 mg, 0.39 mmol) in warm (80° C.) methanesulfonic acid. The reaction is judged complete by TLC analysis after 6 hours when the resorcinol ($R_f$=0.30; chloroform/methanol/acetic acid 50:5:1) disappears and is replaced by an orange-red product at $R_f$=0.45. The desired product is precipitated from the reaction solution by the addition of an excess of water. The product is collected on a Büchner funnel, and dried in vacuo to give the Compound 56 as a reddish powder.

Example 58

Preparation of 2,7-difluoro-6-hydroxy-1-(1-naphthyl)xanthene-3-one (57)

Two equivalents of 4-fluororesorcinol (Compound 15) are condensed with one equivalent of naphthalene-1-carboxaldehyde in warm methanesulfonic acid. When the reaction is judged complete by TLC analysis, the intermediate product is precipitated from the reaction solution by the addition of an excess of water. The crude solid is collected on a Buichner funnel, and dried in vacuo. The intermediate is then dissolved in chloroform and treated with an excess of chloramine-T. When the oxidation reaction is complete, as judged by TLC, the volatiles are removed in vacuo and the crude product is purified using flash chromatography to give Compound 57.

Preparation of Derivatized Fluorinated Fluorophores

General method M for the preparation of thioether derivatives

A solution of the desired "bottom-ring" fluorinated fluorescein (1 eq) and mercaptoacetic acid (1.2 eq) in DMF, as 5% w/v solution, is heated at 80° C. for 40 minutes. The reaction is poured into 7 volume of ice water and extracted twice with ethyl acetate. The combined organic extract is washed with brine, dried, concentrated in vacuo, and purified using silica gel flash column chromatograph eluted with $CHCl_3$:methanol:acetic acid (85:15:0.3, 30 mL) then THF:trifluoroacetic acid (100:0.5, 200 mL).

Fractions containing pure product are combined, and concentrated in vacuo. The residue is dissolved in a minimum of THF, and filtered into 40 volumes of petroleum ether (bp. 30–60° C.). The resulting precipitate is collected, washed with petroleum ether, and dried to yield the desired product.

Example 59

Preparation of 6-carboxymethylthio-4,5,7-trifluorofluorescein (58)

Following general method M, Compound 58 is prepared from Compound 34 in 80% yield. $^1$H-NMR ($d_6$-DMSO) 9.63 (br, 2H), 7.60 (s, 1H), 6.65 (m, 4H), 6.52 (dd, 2H), 3.58 (s, 2H). $^{19}$F-NMR ($d_6$-DMSO) 109.76 (d, 1F), 120.13 (d, 1F), 138.33 (t, 1F).

Example 60

Preparation of 6-carboxymethylthio-2',4,5,7,7'-pentafluorofluorescein (59)

Following general method M, Compound 59 is prepared from Compound 26 in 77% yield. $^1$H-NMR ($d_6$-DMSO)

7.02 (d, 2H), 6.88 (d, 2H), 4.18 (s, 2H). $^{19}$F-NMR (d$_6$-DMSO) 110.65 (br, 1F), 120.62 (d, J=22.4 Hz, 1F), 134.84 (br, 2F), 138.15 (br, 1F).

Example 61

Preparation of 4-(or-6)-carboxymethylthio-2',4',5',7'-tetrabromo-5,6,7-(or 4,5,7)-trifluorofluorescein Diacetate (60)

Following general method M, Compound 60 is prepared from Compound 31 in 81% yield as a mixture of two isomers in 1:2 ratio. There are two distinct sets of NMR signals: $^1$H-NMR (d$_6$-DMSO) 7.91 (s, 2H), 3.90 (s, 2H), 2.45 (s, 6H). $^{19}$F-NMR (d$_6$-DMSO) 112.95 (d, J=19.3 Hz, 1F), 120.98 (d, J=23.0 Hz, 1F), 137.17 (t, J=21.6 Hz, 1F). The other isomer: $^1$H-NMR (d$_6$-DMSO) 7.85 (s, 2H), 4.19 (s, 2H), 2.45 (s, 6H). $^{19}$F-NMR (d$_6$-DMSO) 110.53 (d, J=19.9 Hz, 1F), 119.34 (d, J=23.2 Hz, 1F), 136.73 (t, J=21.6 Hz, 1F).

General method N for the preparation of succinimidyl ester derivatives

Succinimidyl trifluoroacetate (STFA) (1.3 eq), which is prepared from N-hydroxysuccinimide and trifluoroacetic anhydride, is added to a solution of the appropriate fluorinated fluorescein (1 equivalent) in pyridine. The reaction is stirred for 16 hours at 20° C., during which time more STFA (1 equivalent×2) is added to force the reaction to completion. The reaction mixture is then diluted with 10 volume of ether, washed twice with 1M citric acid solution and once with brine, dried, and concentrated in vacuo. The residue is purified using column chromatography eluting with CHCl$_3$:methanol:acetic acid (95:5:0.1 to 80:20:0.1 stepping gradient) to yield the desired product.

Example 62

Preparation of 6-carboxy-2',7'-difluorofluorescein, Succinimidyl Ester (61)

Following general method N, Compound 61 is prepared from Compound 35 in 70% yield. $^1$H-NMR (d$_6$-DMSO) 8.39 (d, 1H), 8.24 (d, 1H), 7.96 (s, 1H), 6.89 (d, 2H), 6.71 (d, 2H), 2.88 (s, 4H). $^{19}$F-NMR (d$_6$-DMSO) 135.12 (dd).

Example 63

Preparation of 5-carboxy-2',7'-difluorofluorescein, succinimidyl ester (62)

Following general method N, Compound 62 is prepared from Compound 36 in 72% yield. $^1$H-NMR (d$_6$-DMSO) 8.51 (s, 1H), 8.45 (d, 1H), 7.57 (d, 1H), 6.90 (d, 4H), 6.77 (d, 2H), 2.94 (s, 4H). $^{19}$F-NMR (d$_6$-DMSO) 135.19 (dd).

Example 64 preparation of 6-carboxyrethylthio-4,5,7-trifluorofluorescein, succinimidyl ester (63)

Following general method N, Compound 63 is prepared from Compound 58 in 65% yield.

Example 65

Preparation of 6-carboxymethylthio-2',4,5,7,7'-pentafluorofluorescein, Succinimidyl Ester (64)

Following general method N, Compound 64 is prepared from Compound 59 in 67% yield. $^1$H-NMR (d$_6$-DMSO) 10.82 (br, 2H), 6.94 (d, 2H), 6.88 (d, 2H), 4.33 (s, 2H), 2.76 (s, 4H). $^{19}$F-NMR (d$_6$-DMSO) 110.45 (d, J=19.9 Hz, 1F), 120.17 (d, J=23.2 Hz, 1F), 135.27 (br, 2F), 138.44 (t, J=21.3 Hz, 1F).

Example 66

Preparation of 5-(and-6)-carboxy-2',4',5',7'-tetrafluorofluorescein, Succinimidyl Ester (65)

Compound 65 is prepared by treating a THF solution (11 mL) of Compound 40 (0.19 g, 0.47 mmol) with a solution of N-hydroxysuccinimide (52 mg, 0.45 mmol) and EDAC (86 mg, 0.45 mmol) in DMSO (1.5 mL). After 24 hours the reaction solution is partitioned between water and ether. The ether portion is concentrated, and the residue purified by flash chromatography to give Compound 65 as 0.05 g (22%) of a red powder: R$_f$=0.30 (CHCl$_3$:methanol:acetic acid, 20:4: 1); UV max (pH 8.5 phosphate buffer) 510 nm ($\epsilon$62,000 cm$^{-1}$M$^{-1}$). Starting material (36, 0.06 g (32%)) is also recovered.

Example 67

Preparation of 4-(or-6)-carboxymethylthio-2',4',5',7'-tetrabromo-5,6,7-(or 4,5,7)-trifluorofluorescein Diacetate, Succinimidyl Ester (66)

N-Hydroxysuccinimide (0.30 g, 2.60 mmol) is added to a solution of Compound 60 (2.00 g, 2.28 mmol) and N,N'-dicyclohexylcarbodiimide (DCC) (0.48 g, 2.32 mmol) in dry THF (40 mL) at 0° C. The reaction is stirred at 0° C. for 10 minutes and at 20° C. for 2 hours, filtered, concentrated in vacuo, and the resulting residue is purified using column chromatography eluting with THF:hexane (50:50 to 80:20 stepping gradient) to yield 1.50 g (67%) of Compound 66. $^1$H-NMR (d$_6$-DMSO) 7.76 (s, 2H), 4.38 (s, 2H), 2.78 (s, 4H), 2.47 (s, 6H). $^{19}$F-NMR (d$_6$-DMSO) 110.61 (br, 1F), 118.99 (d, J=20.7 Hz, 1F), 137.01 (t, J=21.0 Hz, 1F).

Example 68

Preparation of 4-(or-6)-carboxymethylthio-2',4',5',7'-tetrabromo-5,6,7-(or 4,5,7)-trifluorofluorescein, Succinimidyl Ester (67)

A solution of Compound 66 (430 mg, 0.44 mmol) in pyridine (10 mL) is stirred at 20° C. for 24 hours. The reaction is diluted with ethyl acetate (100 mL), washed with 1M citric acid solution (50 mL ×2), brine, and dried. The resulting solution is stirred with charcoal for 10 minutes, filtered, and concentrated in vacuo to yield 140 mg (36%) of Compound 67. The mix of isomers produces two distinct sets of NMR signals: $^1$H-NMR (d$_6$-DMSO) 7.50 (br, 2H), 4.17 (s, 2H), 2.80 (s, 4H). $^{19}$F-NMR (d$_6$-DMSO) 110.73 (br, 1F), 119.73 (br, 1F), 137.15 (br, 1F). The other isomer: $^1$H-NMR (d$_6$-DMSO) 7.38 (br, 2H), 3.85 (s, 2H), 2.90 (s, 4H). $^1$F-NMR (d$_6$-DMSO) 113.11 (br, 1F), 119.02 (br, 1F), 137.57 (br, 1F).

Example 69

Preparation of-6-amino-4-5,7-trifluorofluorescein (68)

A solution of 6-azido-4,5,6-trifluorofluorescein (synthesis given in Example 79) in ethanol is treated with a 5-fold molar excess of stannous chloride dihydrate (as described by Gee et al., SYNTHETIC COMMUNICATIONS, 23(3), 357 (1993)). The resulting solution is stirred until all the azide compound is consumed, as judged by TLC (typically 1–2 hours). The resulting reaction mixture is partitioned between THF/ethyl acetate and water; the pH of the aqueous layer is raised to 4–5 by addition of dilute sodium bicarbonate. The organic layer is concentrated and the reside is purified using flash chromatography, yielding Compound 68 as an orange solid.

Example 70

Preparation of 6-isothiocyanato-4,5,7-trifluorofluorescein (69)

A solution of 6-amino-4,5,7-trifluorofluorescein in anhydrous acetone is treated with a 10-fold molar excess of thiophosgene at room temperature. The reaction solution is incubated at room temperature until all starting material is consumed, as judged by TLC analysis. The product precipitates from the reaction mixture, and is collected by filtration. The filtrand is dried in vacuo at 110° C. for two hours, giving pure Compound 69 as an orange solid.

Example 71

Preparation of 6-nitro-4-5,7-trifluorofluorescein (70)

A solution of 6-amino-4,5,7-trifluorofluorescein in $CHCl_3$ is treated with an excess of m-chloroperbenzoic acid to yield the crude product (Emmons et al. J. AM. CHEM. SOC., 79, 5528 (1957); Gilbert et al., J. ORG. CHEM., 44, 659 (1979)).

Alternatively, 6-amino-4,5,7-trifluorofluorescein is converted into its diazonium salt by treatment with nitrous acid. The pH of the reaction solution is raised to neutral or slightly alkaline. Subsequent treatment with sodium nitrite gives crude Compound 70 (Frolov et al. J. ORG. CHEM. USSR, 5, 1767 (1969)).

In both reactions the product is purified using flash chromatography. Alternatively, the crude product is converted to the diacetate by treatment with acetic anhydride and pyridine, followed by flash chromatography. The purified diacetate is converted into pure Compound 70 by treatment with ammonium hydroxide.

Example 72

Preparation of 5-chloromethyl-2',7'-difluorofluorescein (71)

The mixed anhydride of 5-(and-6)-carboxy-2',7'-difluorofluorescein diacetate is prepared from the carboxylic acid and ethyl chloroformate (1 eq.) in cold THF in the presence of triethylamine (1.2 eq.). The mixed anhydride is reduced in situ by the addition of an excess of sodium borohydride (3 eq.). After acidification and treatment with hot acetic anhydride in pyridine, the resulting triacetate is purified by flash chromatography (acetone/hexanes), followed by treatment with hydrochloric acid in hot acetic acid to give Compound 71, after flash chromatography (5% methanol/chloroform).

Example 73

Preparation of 5-(and-6)-carboxy-2',7'-difluorofluorescein-X, Succinimidyl Ester (72)

To a solution of 5-(and 6)-carboxy-2',7'-difluorofluorescein, succinimidyl ester in THF is added a solution of 6-aminohexanoic acid in DMSO. After the reaction is judged complete by TLC analysis, the reaction product is precipitated from water and collected by filtration. After drying, a solution of EDAC.HCl (1.1 eq.) in DMSO is added to a solution of the first reaction product (1.0 eq.) and N-hydroxysuccinimide (1.0 eq.) in an equal volume of THF. After the reaction is judged complete by TLC analysis, the product is worked up and purified as described above for 5-(and 6)-carboxy-2',7'-difluorofluorescein, succinimidyl ester to give Compound 72.

Example 74

Preparation of 5-(and-6)-carboxy-2',7'-difluorofluorescein, phalloidin conjugate (73)

To a solution of 3 mg (0.003 mmol) of aminophalloidin p-toluenesulfonate and 3 mg (0.006 mmol) of 5-(and-6)-carboxy-2',7'-difluorofluorescein, succinimidyl ester in 300 μL of DMF is added 5 μL of N,N'-diisopropylethylamine and the mixture is stirred at room temperature for one hour. To the reaction mixture is added 7 mL of diethyl ether and the resulting precipitate is collected by centrifugation. The crude product is then purified by chromatography over lipophilic SEPHADEX LH-20 resin using water as eluant. The desired fractions are combined and lyophilized to give 3 mg (81%) of Compound 73 as an orange solid. $R_f$=0.55 (silica gel, $CHCl_3$:methanol:$H_2O$:acetic acid; 15:10:1:0.1)

Example 75

Preparation of 5-(and-6)carboxy-2',7'-difluorofluorescein, Bisindolylmaleimide Conjugate (74)

To a solution of 50 mg (0.13 mmol) of 2-(1-(3-aminopropyl)-indol-3-yl)-3-(1-methylindol-3-yl)maleimide in 40 μL of dry dichloromethane is added 70 mg (0.13 mmol) of the succinimidyl ester of 5-(and-6)-carboxy-2',7'-difluorofluorescein diacetate and the mixture is stirred at room temperature for 18 hours. To the reaction mixture is added 100 μL of acetic acid, and the reaction mixture is washed twice with water. The organic layers are combined, dried over sodium sulfate and concentrated to give the crude intermediate diacetate of Compound 74. This intermediate is purified by column chromatography on silica gel with 1% methanol in chloroform as eluant to give 65 mg of an orange solid. This solid is then dissolved in 1 mL of 0.2M potassium hydroxide in methanol and stirred at room temperature for 15 minutes. The resulting mixture is treated with 3 mL of 0.1M HCl solution followed by the addition of 5 mL of water. The resulting precipitate is collected by filtration and dried under vacuum to give 50 mg (51%) of Compound 74 as an orange-red solid.

Example 76

Preparation of 5-(and-6)-amino-2',7'-difluorofluorescein (75)

A solution of anhydrous tin chloride (1.77 g, 9.3 mmol) and Compound 38 (0.74 g, 1.8 mmol) in 20 mL of absolute ethanol/ethyl acetate (1:2) is heated at 70° C. for 1 hour. The reaction mixture is diluted with ethyl acetate (100 mL), washed three times with water and one time with brine, dried, and concentrated in vacuo. The residue is then purified using silica gel flash column chromatography eluting with $CHCl_3$:methanol (95:5 to 85:15 stepping gradient) to yield Compound 75 as 0.62 g (89%) of an orange powder. $^1$H-NMR ($d_6$-DMSO) 6.98 (d, 2H), 6.68 (s, 2H), 6.60 (d, 2H). $^{19}$F-NMR ($d_6$-DMSO) 128.49 (br, 1F), 138.49 (m, 2F).

Example 77

Preparation of 2',7'-difluorofluorescein-5-(and-6)-isothiocyanate (76)

To a pale yellow-brown solution of thiophosgene (1.70 g, 14.8 mmol) in acetone (5.0 mL) at room temperature is added with stirring a solution of 5-(and 6)-amino-2',7'-difluorofluorescein (75, 2.50 g, 6.52 mmol) in acetone (35 mL) over 15 minutes. The resulting solution is allowed to stand for 90 minutes, then concentrated in vacuo. The resulting dark yellow foam is dried in vacuo over refluxing toluene for two hours, then at ambient temperature for 20 hours, giving Compound 76 as 2.44 g of a yellow-orange powder (88%) yield. $R_f$=0.60 (chloroform/methanol/acetic acid 20:4:1); $^1$H NMR (CD$_3$OD) 7.9 (s, 1H); 7.63 (d, 1H); 7.29 (d, 1H); 6.8 (2 s, 2H); 6.45 (2 s, 2H). $^{19}$F NMR (d$_6$-DMSO) 135.2 (s). UV max (pH 9 phosphate buffer) 493 nm ($\epsilon$=78,200 cm$^{-1}$M$^{-1}$). Emission maximum 520 nm.

Example 78

Preparation of 2',7'-difluoro-5-(and 6)-iodoacetamidofluorescein (77)

To a solution of 5-(and 6)-amino-2',7'-difluorofluorescein (75, 2.00 g, 5.22 mmol) in DMF (10 mL, Aldrich anhydrous) under air is added a solution of iodoacetic anhydride (2.38 g, 6.7 mmol, crystallized from hexanes). The resulting dark yellow solution is stirred at room temperature for 40 minutes, then poured into water (100 mL), to which 1.7 mL concentrated ammonium hydroxide has already been added. The pH is raised from 4.5 to 9.0 by dropwise addition of concentrated ammonium hydroxide. After three minutes the pH is lowered to 1.5 by dropwise addition of hydroiodic acid (57%). The resulting mixture is centrifuged. The pellet is rinsed with water (150 mL), followed by centrifugation. The pellet is then dried in vacuo over phosphorous pentoxide/sodium hydroxide in darkness for 12 hours. The still moist solid is slurried with water (100 mL), followed by filtration. The filtrand is dried via lyophilization, giving the Compound 77 as 1.81 g of a yellow-orange powder (63%). The product is purified further by flash chromatography, using 0.5% acetic acid/THF as the mobile phase. The product thus obtained is purified further still by preparative TLC, using silica gel plates (100 $\mu$) and chlorofonm/methanoVacetic acid (20:4:1) as the mobile phase; the product band at $R_f$=0.35 is rinsed with THF, followed by filtration and concentration to give Compound 77 as an orange powder: $R_f$=0.46 (chloroform/methanol/acetic acid 20:4:1); $^1$H NMR (d$_6$-DMSO) 8.3 (s, 1H); 7.8 (d, 1H); 7.25 (d, 1H); 6.87 (d, 2M); 6.54 (2 s, 2H); 3.89 (s, 2H). $^{19}$F NMR (d$_6$-DMSO) 138.8. UV max (pH 9 phosphate buffer) 494 nm ($\epsilon$=67,600 cm$^{-1}$M$^{-1}$); emission maximum 516 nm. Anal. calc. for $C_{22}H_{12}NO_6F_2I$; C, 47.94; H, 2.19; N, 2.54. Found: C, 50.32; H, 3.29; N, 2.10.

Example 79

Preparation of 6-azido-4,5,7-trifluorofluorescein (78)

A solution of sodium azide (0.70 g, 10.7 mmol) in 40 mL water is added to a solution of Compound 34 (2.0 g, 4.9 mmol) in 40 mL acetone at 20° C. the reaction is then heated at 60° C. for 3 hours. The acetone is distilled off and the remaining mixture is poured into 20 mL ice water. The precipitate is collected, washed with water, and dried by azeotroping with absolute ethanol (2×) to yield 2.22 g orange solid. The crude product is converted to the diacetate according to General Method J, purified by column chromatography, recrystallized from absolute ethanol to yield pure 6-azido-4,5,7-trifluorofluorescein diacetate as 1.67 g (79%) of a colorless solid. $^1$H-NMR (CDCl$_3$) 7.13 (d, 2H), 7.00 (d, 2H), 6.91 (d, 2H), 2.33 (s, 6H). $^{19}$F-NMR (CDCl$_3$) 131.77 (dd, 1F), 139.48 (dd, 2F), 140.08 (dd, 1F).

Following general method K, treatment of the intermediate diacetate gives Compound 78 as an orange powder in 92% yield. $^1$H-NMR (d$_6$-DMSO) 6.98 (dd, 2H), 6.68 (d, 2H), 6.49 (dd, 2). $^{19}$F-NMR (d$_6$-DMSO) 128.95 (t, 1F), 138.40 (d, 2F).

Example 80

Preparation of 2',7'-difluoro-5-dodecanoylaminofluorescein (79)

5-Amino-2',7'-difluorofluorescein (3.1 mmole) is dissolved in dry dimethylformamide (10 mL) containing triethylamine (1.63 mL, 11.7 mmole) and a solution of dodecanoyl chloride (2.60 g, 11.7 mmole) in dry dimethylformamide (5 mL) is added dropwise to the rapidly stirred solution to yield a light red solution plus a precipitate. After stirring for 2.5 hours, the reaction mixture is placed in an oil bath (90° C.) for 45 minutes, cooled to room temperature and stored at −12° C. overnight. The product is isolated by pouring the cold reaction mixture into 1.5M sodium hydroxide solution (200 mL). After stirring mechanically for 1 hour at room temperature, the basic solution is extracted with hexane (3×200 mL) and acidified with concentrated hydrochloric acid to pH 1, yielding an orange precipitate. The precipitate is dried for 5 hours in vacuo over $P_2O_5$, triturated with diethyl ether (400 mL), and filtered to yield a fine red powder. This powder is crystallized from methanol (2×150 mL) to remove non-dye material. The filtrate is evaporated to dryness and redissolved in 9:1 chloroform:methanol (220 mL) and this solution is extracted with water (10 mL). The organic layer is dried over anhydrous magnesium sulfate, filtered, evaporated under reduced pressure and dried in vacuo to yield Compound 79 an orange solid.

Example 81

Preparation of 2',7'-difluorofluorescein-5-(and-6)-thiosemicarbazide (80)

To an anhydrous tetrahydrofuran solution of 2',7'-difluorofluorescein-5-(and-6)-isothiocyanate (76) is added one molar equivalent of hydrazine under nitrogen at room temperature with stirring. After the reaction is judged complete by TLC analysis, the volatiles are removed using rotary evaporation. The crude product is dissolved in methanol, and the resulting solution is added to an excess of ether/hexanes. The resulting precipitate is collected on a Büchner funnel and dried in vacuo to give pure Compound 80.

Example 82

Preparation of 9-cyano-2,7-difluoro-6-hydroxy-3H-xanthene-3-one (81)

Two equivalents of 4-fluororesorcinol (15) are condensed with one equivalent of formaldehyde (as formalin) in warm methanesulfonic acid. When the reaction is judged complete by TLC analysis, the product is precipitated from the reaction solution by the addition of an excess of water. The resulting precipitate is collected on a Büchner funnel, and dried in vacuo. The intermediate product is then dissolved in chloroform and treated with an excess of chloramine-T. When the oxidation reaction is complete, as judged by TLC, the volatiles are removed in vacuo and the residue purified using flash chromatography. The resulting pure compound is then treated with an excess of sodium cyanide in methanol to give Compound 81 after removal of volatiles and purification using flash chromatography.

Example 83

Preparation of 9-(4-carboxybutyl)-2,7-difluoro-6-hydroxy-3H-xanthene-3-one (82)

Two equivalents of 4-fluororesorcinol (15) are condensed with one equivalent of glutaric anhydride in warm methanesulfonic acid. When the reaction is judged complete by TLC analysis, the product is precipitated from the reaction solution by the addition of an excess of water. The resulting precipitate is collected on a Büchner funnel, and dried in vacuo to give Compound 82.

Preparation of Fluorinated Sulfonefluoresceins and Their Analogs

Example 84

Preparation of 9-(4-carboxy-2-sulfophenyl)-2,4,5,7-tetrafluoro-6-hydroxy-3H-xanthene-3-one (83)

2,4-Difluororesorcinol (13, 0.200 g, 1.37 mmol) and 2-sulfoterephthalic acid (0.184 g, 0.68 mmol) are heated together in methanesulfonic acid (2 mL) at 100° C. overnight with stirring. After cooling, the reaction mixture is poured into cold water (30 mL). Sodium chloride is added portionwise with stirring until a precipitate forms, which is collected on a Buichner finnel and dried in vacuo to give Compound 83 as 40 mg of a red-orange powder: $R_f$=0.65 ($CH_3CN:H_2O$:acetic acid 8:1:1).

Preparation of Fluorinated Dihydrofluoresceins

Example 85

Preparation of 4,5,6,7-tetrafluorodihydrofluorescein (84)

To a solution of 4,5,6,7-tetrafluorofluorescein (34, 2.00 g, 4.95 mmol) in acetic acid (60 mL) under air at room temperature is added zinc dust (2.10 g, 30.6 mmol). The resulting mixture is stirred in darkness overnight, then filtered. The colorless filtrate is concentrated via rotary evaporation, leaving an amber foam from which diethyl ether is evaporated, leaving a water-soluble yellow-orange foam (2.3 g). A portion is purified via chromatography on SEPHADEX LH-20 resin, using methanol/water as the mobile phase, giving Compound 84 as a pale yellow powder after lyophilization: $R_f$=0.13 (chloroform/methanol/acetic acid 15:3:1); $^1$H NMR ($D_2O$) 6.8 (br s, 2H); 6.4 (m, 4H); (5.15 (s, 1H). $^{19}$F NMR ($D_2O$) 139.9 (1F); 143.5 (1F); 155.3 (2F).

Example 86

Preparation of 6-carboxy-2',7'-difluorodihydrofluorescein (85) and 6-carboxy-2',7'-difluorodihydrofluorescein diacetate (86)

To a solution of 6-carboxy-2',7'-difluorofluorescein (35, 0.64 g, 1.6 mmol) in methanol/acetic acid (1:2, 15 mL) under nitrogen at room temperature is added zinc dust (0.65 g, 9.5 mmol). The resulting mixture is stirred in darkness for 12 hours, then filtered through diatomaceous earth. The pale yellow filtrate is concentrated to a volume of 8 mL, then added dropwise to cold water (75 mL) with stirring. The resulting precipitate is collected on a Büchner funnel, and rinsed with water (15 mL), briefly air dried, then dried in vacuo over $P_2O_5$/NaOH in darkness, giving Compound 85 as 0.64 g (100%) of a pale tan powder: $R_f$=0.20 (chloroform:methanol:acetic acid, 20:4:1).

This compound (0.64 g, 1.55 mmol) is then suspended in acetic anhydride (8 mL) under air at room temperature, then treated with pyridine (2 mL). The resulting pale yellow solution is concentrated in vacuo, and the residue partitioned between water and ether. The organic portion is washed with brine (1×) dried over sodium sulfate and concentration to 0.8 g of a pale yellow syrup. This syrup is dissolved in diethyl ether/ethyl acetate (2;1, 60 mL) and the resulting solution washed with 0.5M HCl, dried and concentrated in vacuo to 0.78 g of a colorless foam. This foam is triturated with ether (30 mL) to give the diacetate of Compound 85 as 0.65 g (84%) of a colorless powder (Compound 86). $R_f$=0.66 (chloroform/methanol/acetic acid 20:4:1); $^1$H NMR ($d_6$-DMSO) 7.63 (dd, 2H); 7.37 (s, 1H); 7.15 (m, 4H); 6.55 (s, 1H); 1.81 (s, 6H). $^{19}$F NMR ($d_6$-DMSO) 130.3.

Example 87

Preparation of 6-carboxymethylthio-2',4-5,7,7'-pentafluorodihydrofluorescein (87)

A solution of 6-carboxymethylthio-2',4,5,7,7'-pentafluorofluorescein (59, 40 mg, 0.08 mmol) in acetic acid/methanol (1:1, 3 mL) is treated with zinc dust (80 mg, 1.2 mmol) under air at room temperature. After 72 hours the reaction mixture is filtered, and the colorless filtrate is purified on SEPHADEX LH-20 resin using acetone/water as the mobile phase, giving Compound 87 as 41 mg of a pale yellow powder after lyophilization. $^1$H NMR($D_2O$) 6.71 (d, 2H); 6.59 (d, 2H); 5.18 (br s, 1H); 3.5 (br s, 2H). $^{19}$F NMR ($D_2O$) 126.3 (2F); 141.0 (3F); 143.9 (1F).

Example 88

Preparation of 2',4,5,6,7,7'-hexafluorodihydrofluorescein (88)

As described for Compound 87, treatment of 2',4,5,6,7,7'-hexafluorofluorescein (26, 0.20 g, 0.45 mmol) with zinc dust (250 mg) gives, after purification on SEPHADEX LH-20 resin, Compound 88 as 80 mg (40%) of a pale orange powder. $R_f$=0.12 (chloroform/methanol/acetic acid 15:3:1).

Example 89

Preparation of 2',7'-dichloro-4,5,6,7-tetrafluorodihydrofluorescein (89)

As described for Compound 87, treatment of 2',7'-dichloro-4,5,6,7-tetrafluorofluorescein (28, 42 mg, 0.09 mmol) with zinc dust (100 mg) gives, after purification on SEPHADEX LH-20 resin, Compound 89 as 34 mg (81%) of a pale yellow powder. $R_f$=0.17 (chloroform/methanol/acetic acid, 15:3:1).

Preparation of Fluorinated β-Galactosidase Substrates
General Method O

A mixture of the desired fluorinated fluorescein (1 equivalent), tetra-O-acetylbromogalactose (1.5 equivalents), and silver (I) oxide (1.5 equivalents) in anhydrous TrF (0.02M in dye, Aldrich) is stirred at room temperature under nitrogen. The reaction is monitored by TLC, and takes 72–96 hours to complete; more silver oxide is added as necessary. The reaction mixture is filtered, and the filtrate concentrated. The resulting residue is purified via flash chromatography to give pure mono-alkylated product.

Example 90

Preparation of 2',7'-difluorofluorescein, tetra-O-acetylgalactoside (90)

Using general method O, 2',7'-difluorofluorescein (29, 70 mg, 0.19 mmol, $R_f$=0.13 (CHCl$_3$/methanol/acetic acid 50:5:1)) gives Compound 90 as 0.12 g (92%) of a yellow foam: $R_f$=0.31 (CHCl$_3$/methanol/acetic acid 50:5:1).

Example 91

Preparation of 4,5,6,7-tetrafluorofluorescein, Tetra-O-acetylgalactoside (91)

Using general method O, 4,5,6,7-tetrafluorofluorescein (34, 2.00 g, 5.95 mmol, $R_f$=0.29 (CHCl$_3$/methanol/acetic acid 50:5:1)) gives Compound 91 as 2.02 g (55%) of a red foam: $R_f$=0.58 (CHCl$_3$/methanol/acetic acid 50:5:1); $^1$H NMR (CDCl$_3$) 7.0–6.7 (m, 6H), 5.5 (m, 1H), 5.1 (m, 1H), 4.1 (m, 5H), 2.1 (m, 12H).

General Method P

A mixture of the desired fluorinated fluorescein mono (tetra-O-acetyl)galactoside (1 equivalent), tetraacetobromogalactose (1.5 equivalents) and cadmium carbonate (1.5 equivalents) in dry toluene is heated at reflux for four days. The cooled reaction mixture is filtered and the filtrate concentrated. The residue is then purified by flash chromatography to give the desired non-fluorescent protected galactosidase substrates.

Example 92

Preparation of 2',7'-difluorofluorescein, bis-tetra-O-acetylgalactoside (92)

Using general method P, treatment of Compound 90 (0.12 g, 0.17 mmol) gives Compound 92 as 0.11 g (62%) of a pale yellow viscous oil: $R_f$=0.79 (CHCl$_3$/methanol/acetic acid 50:5:1). Starting material (Compound 90, 0.04 g, 33%) is also recovered.

Example 93

Preparation of 4,5-6,7-tetrafluorofluorescein, bis-tetra-O-acetlgalactoside (93)

Using general method P, treatment of Compound 91 (2.00 g, 2.72 mmol) gives Compound 93 as 0.44 g (16%) of a pale yellow foam: $R_f$=0.79 (CHCl$_3$/methanol/acetic acid 50:5:1); $^1$H NMR (CDCl$_3$) 6.9 (m, 4H), 5.5 (m, 3H), 5.1 (m, 3H), 4.2 (m, 10H), 2.1 (m, 24 H).

Example 94

Preparation of 2',7'-difluorofluorescein, bis-O-galactoside (94)

To a solution of Compound 92 (90 mg, 0.087 mmol) in anhydrous methanol (3.0 mL, Aldrich) under nitrogen at room temperature is added sodium methoxide solution (0.22M in methanol, 0.24 mL, 0.053 mmol). The resulting solution is stirred for 24 hours, then quenched with a few drops of aqueous citric acid. The volatiles are removed in vacuo, and the residue is purified by preparative TLC (silica gel, 10% methanol/chloroform), in which the impurities and remaining starting material are eluted away from desired product, which remains on the baseline. The product band is collected and rinsed with ethyl acetate/methanol (1:1). Filtration, concentration, and lyophilization of the residue from water gives 17 mg (28%) of a pale yellow powder, homogeneous by TLC ($R_f$(ethyl acetate/water/methanol/acetic acid 7:1:1:1)0.39). Some of this product (14 mg) is further purified by chromatography on SEPHADEX LH-20 resin, using water as the mobile phase; the product fractions are pooled and lyophilized to give Compound 94 as 11 mg of a very pale yellow fluffy powder.

Example 95

Preparation of 4,5,6,7-tetrafluorofluorescein, bis-O-galactoside (95)

To a pale yellow solution of Compound 93 (0.23 g, 0.22 mmol) in dioxane (6 mL) at room temperature is added a solution of lithium hydroxide (4.2 mg, 0.10 mmol) in 1 mL water. The resulting solution is stirred for seven days, during which more LiOH (7.5 mg, 1.8 mmol) is added. A few drops of aqueous citric acid are added, followed by concentration in vacuo. The resulting residue is purified by chromatography on SEPHADEX LH-20 resin, using water/methanol 1:0 to 1:1. The product fractions are pooled and concentrated via rotary evaporation. The residue is dissolved in water and lyophilized to give Compound 95 as 40 mg (25%) of a fluffy pale yellow powder: $R_f$=0.37 (ethyl acetate/water/methanol/acetic acid 7:1:1:1); $^1$H NMR (D$_2$O) 7.1 (m, 4H), 6.9 (d, 2H), 5.12 (d, 2H), 4.08 (s, 2H), 3.95–3.75 (m, 10H); $^{19}$F NMR (D$_2$O) 136.8, 139.4, 140.8, 148.0.

Preparation of Alkaline Phosphatase Substrates

General Method Q

The general scheme for preparation of fluorinated fluorescein phosphatase substrates typically requires initial phosphorylation of the fluorophore with phosphorus oxychloride. Typically, the fluorescein dye is dissolved in pyridine under nitrogen at 0° C. under nitrogen. To the fluorescein solution is added a pyridine solution of POCl$_3$. After the reaction is judged complete by TLC, the reaction is quenched by pouring the solution into crushed ice and neutralizing the mixture with ammonium hydroxide (to pH 7.0). The pyridine is then extracted with chloroform, and the aqueous phase is lyophilized. The crude material is purified further on a SEPHADEX LH20 resin column, eluting with water. Pure product fractions are pooled, frozen and lyophilized to give pure fluorinated fluorescein diphosphates as their tetraammonium salts, as pale yellow solids.

Example 96

Preparation of 2',7'-difluorofluorescein Diphosphate, Tetraammonium Salt (96)

Using general method Q, 2',7'-difluorofluorescein (29) is converted into the diphosphate Compound 96.

Example 97

Preparation of 2',4,5,6,7,7'-hexafluorofluorescein Diphosphate, Tetraammonium Salt (97)

Using general method Q, 2',4,5,6,7,7'-hexafluorofluorescein (26) is converted into the diphosphate Compound 97.

Preparation of Fluorinated Analogs of Calcein-AM
General Method R

Typically, the free fluorinated dye is dissolved in ethanol and 6M potassium hydroxide to make a 0.2M solution. The resulting solution is treated with 3 equivalents of iminodiacetic acid, followed by aqueous formaldehyde (4 equivalents). The resulting solution is heated at 65° C. overnight, then doubled in volume with water/ethanol. The pH is lowered to 2.0 by careful addition of aqueous HCl, and the resulting precipitate collected by filtration. This crude intermediate is partially purified by trituration with acetone, followed by filtration. This intermediate is suspended in DMF and treated with 10 equivalents of diisopropylethylamine (DIEA), followed by addition of acetic anhydride (4 equivalents). After stirring for 30 minutes, more DIEA (7 equivalents) is added, followed by water dropwise until homogeneity is achieved. Bromomethyl acetate (15 equivalents) is added, and the resulting solution stirred overnight. The reaction mixture is partitioned between ethyl acetate and water. The organic layer is washed with brine, concentrated and then purified by preparative TLC, using hexanes:ethyl acetate as eluant, giving the pure product as a colorless oil.

Example 98

Preparation of 4,5,6,7-tetrafluoro-calcein AM (98)

Beginning with 4,5,6,7-tetrafluorofluorescein (25, 0.50 g, 1.2 mmol), General Method R gives the intermediate 4,5,6,7-tetrafluoro-calcein as 0.50 g of an orange powder: $R_f$=0.20 (5:4:1 CHCl$_3$:Methanol:H$_2$O). This intermediate is further treated to give pure Compound 98: $R_F$=0.33 (3:2 ethyl acetate/hexanes). $^1$H NMR (CDCl$_3$) 7.0 (d, 2H); 6.9 (m, 2H); 5,7 (s, 8H); 4.3 (m, 4H); 3.7 (s, 8H); 2.4 (s, 6H); 2.1 (s, 12H). $^{19}$F NMR (CDCl$_3$) 136.9 (m, 1F); 140.5 (m, 1F); 141.4 (t, 1F); 148.8 (t, 1F).

Example 99

Preparation of 2',7'-difluoro-alcein AM (99)

Beginning with 2',7'-difluorofluorescein (29, 0.50 g, 1.4 mmol), General Method R gives the intermediate 2',7'-difluoro-calcein as 0.50 g of an orange powder. This intermediate is further treated to give pure Compound 99: $R_f$=0.41 (3:2 ethyl acetate/hexanes). $^1$H NMR (CDCl$_3$) 8.1 (d, 1H); 7.7 (m, 2H); 7.2 (m, 3H); 6.6 (t, 2H); 5.7 (s, 4H); 4.25 (s, 2H); 3.7 (s, 4H); 2.4 (s, 6H); 2.1 (s, 12H). $^{19}$F NMR (CDCl$_3$) 130.8 (d, 1F); 131.7 (m, 1F).

Example 100

Preparation of 2'-7'-bis-carboxyethyl-4,5,6,7-tetrafluorofluorescein, Acetoxymethyl Ester (100)

Two molar equivalents of 3-(2,4-dihydroxyphenyl) propionic acid are condensed with one equivalent of tetrafluorophthalic acid in warm methanesulfonic acid. The crude 4,5,6,7-tetrafluorinated intermediate dye is obtained by precipitation from water. This intermediate is then treated in DMF with DIEA and then acetic anhydride, followed by bromomethyl acetate, as for the fluorinated calcein-AM analogs described above. The resulting product is purified by chromatography using ethyl acetate/hexanes to yield pure Compound 100.

Example 101

Preparation of bis-(5-t-butoxycarbonylmethoxy)-2-nitrobenzyl-caged 2',4,5,6,7,7'-bexafluorofluorescein (101)

A mixture of 2',4,5,6,7,7'-hexafluorofluorescein (26, 0.50 g, 1.14 mmol), 5-(t-butoxycarbonylmethoxy)-2-nitrobenzyl iodide (1.04 g, 2.64 mmol) and silver (I) oxide (0.70 g, 3.0 mmol) in benzene/ethylacetate (40 mL/30 mL) is heated at reflux in darkness for four days. After cooling, the reaction mixture is filtered. The filtrate is concentrated under vacuum and the residue is purified using flash chromatography to yield the non-fluorescent Compound 101 as 0.51 g (46%) of a very pale yellow powder. $R_f$=0.67 (ethanol/CHCl$_3$, 5:95). The product is initially quenching, but becomes fluorescent upon irradiation. $^1$H NMR (CDCl$_3$) 8.32 (d, 1H); 8.10 (d, 1H); 7.42 (d, 1H)7.20 (d, 1H); 6.96 (dd, 1H); 6.8 (m, 3H); 6.48 (dd, 2H); 5.72 (s, 2H); 5.45 (q, 2H); 4.65,4.60 (2 s, 4H);. $^{19}$F NMR (CDCl$_3$) 120.1 (s, 1F); 132.8 (m, 1F); 134.3 (m, 1F); 134.6 (s, 1F); 145.6 (m, 1F); 148.3 (m, 1F). Anal. calc. for C$_{46}$H$_{36}$N$_2$O$_5$F$_6$.H$_2$O: C, 55.87; H, 3.87; N, 2.83. Found: C, 56.12; H. 4.14; N, 2.79.

Preparation of Ion Indicators Incorporating Fluorinated Fluoresceins

Example 102

Preparation of 5-carboxy-2',7'-difluorofluorescein Diacetate, Isobutyloxycarbonvl Anhydride (102)

5-Carboxy-2',7'-difluorofluorescein diacetate (33, 0.84 g; 1.69 mmol) is suspended in 20 mL methylene chloride at 0° C. and triethylamine (0.19 g; 1.86 mmol) is added dropwise to give a colorless solution. Isobutyl chloroformate (0.23 g; 1.65 mmol) is added in one portion. The reaction is stirred at room temperature for 2 hours, and is then evaporated to a solid, which is suspended in ethyl acetate (50 mL) and filtered. The filtrate is evaporated to give Compound 102 as a colorless foam (0.91 g; 91% yield).

Example 103

Preparation of a Fluorescent Indicator for Submicromolar Ca$^{2+}$ Concentrations Incorporating a 5-carboxy-2',7'-difluorofluorescein (103)

To a solution of Compound 102 (218 mg; 0.365 mmol) in 10 mL methylene chloride is added 200 mg (0.365 mmol) of 5-amino-1,2-bis-(2-aminophenoxyethane)-N,N,N',N'-tetraacetic acid, tetramethyl ester (5-amino BAPTA, tetramethyl ester; Compound I in U.S. Pat. No. 5,453,517 to Kuhn et al. (1995)). The reaction is stirred for 12 hours at room temperature until no Compound 102 remains by TLC in 1:1 ethyl acetate:hexanes. The reaction mixture is then applied directly to a silica gel column eluting with a mixture of ethyl acetate:hexanes (57:43). Pure fractions are evaporated under vacuum to give the tetramethyl ester of Compound 103 as a yellow oil (193 mg; 51% yield).

The intermediate tetramethyl ester (190 mg; 0.185 mmol) is dissolved in 5 mL dioxane. Methanol (2 mL) is added followed by potassium hydroxide (207 mg) as a solution in 3 mL water. The reaction is stirred at room temperature for 60 hours, then is diluted to 20 mL with water, acidified to pH 4 with 10% HCl and centrifuged. The resulting orange pellet is redissolved by adjusting the pH to 8 with dilute KOH and is applied to a column of lipophilic SEPHADEX LH-20 resin eluting with pure water. Pure fractions are frozen and lyophilized to give pure Compound 103 as an orange powder (130 mg, 63% yield). $^1$H NMR(D$_2$O) 8.45 (s, 1H); 8.20 (d, 1H); 7.60 (d, 1H); 7.35 (s, 1H); 7.25–7.15 (m, 2H); 7.10–7.00 (m, 4H); 7.69 (m, 2H); 6.85 (d, 2H); 4.50 (s, 4H); 3.95 (s, 4H); 3.85 (s, 4H). $\epsilon$=61,708 cm$^{-1}$M$^{-1}$ at 493.8 nm in 10 mM EGTA, 100 mM KCl, 10 mM MOPS buffer at pH 7.20.

Example 104

Determination of the Ca$^{2+}$ Binding Affinity of a 5-carboxy-2',7'-difluorofluorescein Conjugate of BAPTA The fluorescence response and dissociation constant of the fluorescent BAPTA conjugates are determined using the Calcium Calibration Buffer Kit II (Molecular Probes, Inc.; Eugene Oreg.), which is based on a method described by Tsien et al. METH. ENZYM. 172, 230 (1989). For example, 1 mg of Compound 103 is dissolved in deionized water and 5 µL is diluted into 3 mL of each of two buffers, which are cross diluted to arrive at a series of $Ca^{2+}$ concentrations between zero and 35 µM. Emission spectra of the dye solutions are scanned between dilutions to generate a family of curves. Each of these curves has maximal fluorescence emission at approximately 530 nm with an increase in fluorescence emission intensity with increasing $Ca^{2+}$ concentration. This intensity change is plotted against the concentration of free $Ca^{2+}$ to give a value for the dissociation constant of the indicator. The intensity increase is approximately 17-fold as $Ca^{2+}$ levels increase from zero to 35 µM. The calculated dissociation constant at 20° C. is 169 nM.

Example 10

Preparation of a Cell Permeable Fluorescent $Ca^{2+}$ Indicator Incorporating a 5-carboxy-2',7'-difluorofluorescein (104)

To a solution of 275 mg (0.35 mmol) of 5-amino-BAPTA, tetraacetoxymethyl ester (Compound XIII, U.S. Pat. No. 5,453,517) in 15 mL methylene chloride is added 0.210 g (0.353 mmol) of Compound 102. The reaction is stirred at room temperature for two hours and then is applied directly to a column of silica gel and eluted with ethyl acetate:hexanes, 3:2. Pure fractions are combined and evaporated to give Compound 104 as a yellow foam (232 mg; 52% yield). $^1$H NMR ($CDCl_3$) 8.55 (s, 1H); 8.40 (s, 1H); 8.45 (d, 1H); 7.30–7.40 (m, 3H); 7.14 (s, 1H); 7.12 (s, 1H); 6.80–7.00 (m, 5H); 6.60 (s, 1H); 6.55 (s, 1H); 5.71 (s, 4H); 5.69 (s, 4H); 4.40 (br s, 2H); 4.35 (br s, 2H); 4.20 (s, 8H); 2.35 (s, 6H); 2.05 (s, 6H); 2.00 (s, 6H).

Example 106

Preparation of a Dextran Conjugate of a Fluorescent $Ca^{2+}$ Indicator Incorporating a 5-carboxy-2',7'-difluorofluorescein (105)

To a solution of 1.26 g (2.24 mmol) 5,5'-diamino-BAPTA tetramethyl ester (Compound XVI in U.S. Pat. No. 5,453,517) in 50 mL methylene chloride is added a solution of Compound 102 in 50 mL methylene chloride. The reaction is stirred at room temperature until the coupling is judged complete by TLC analysis (5 hrs). The reaction is concentrated and applied to a silica gel column eluted with ethyl acetate:methylene chloride, 2:3. Pure fractions are combined and evaporated to give the 5-amino-BAPTA tetramethyl ester conjugate of 5-carboxy-2',7'-difluorofluorescein as a yellow foam (0.73 g; 41% yield).

Thiophosgene (0.24 g; 2.1 mmol) is added in one portion to a solution of the tetramethyl ester derivative (0.73 g; 0.7 mmol) in 15 mL acetone. After stirring 45 minutes at room temperature, TLC analysis (ethyl acetate:hexanes 1:1) showed complete conversion of the amine-substituted precursor to the higher $R_f$ isothiocyanate derivative. The reaction mixture is evaporated and the resulting tan gum is purified on a silica gel column eluting with ethyl acetate:hexanes, 1:1. Pure fractions are combined and evaporated to give the 5-isothiocyanato-BAPTA tetramethyl ester conjugate of 5-carboxy-2',7'-difluorofluorescein as a pale yellow foam (412 mg; 54% yield).

A solution of the isothiocyanato derivative (0.275 g; 0.25 mmol) in 1 mL DMSO is added to a solution of 1.0 g (0.1 mmol) aminodextran, 10,000 MW.(Molecular Probes, Inc, Eugene, Oreg.) in 15 mL DMSO is added. The resulting orange solution is stirred at room temperature for 18 hours, then is added dropwise to a stirred solution of 450 mL acetone, and the resulting orange precipitate is collected by filtration. The moist solid is dissolved in 30 mL pure water and the pH is adjusted to 12.8 by the addition of 40% KOH. After stirring for 90 hours, 1.5 mL acetic anhydride is added and the pH is maintained at >8 by the addition of 40% KOH. After 30 minutes the pH stabilizes at 8.5 and the solution is transferred to dialysis tubing (3,500 MW cutoff) and is dialysed against 2 L of 2% potassium sulfate for 14 hours, then against pure water for two days. The dialysate is then frozen and lyophilized to give 1.08 g of a 10,000 MW dextran conjugate of BAPTA-5-carboxy-2',7'-difluorofluorescein (Compound 105) as an orange solid.

Example 107

Preparation of a Fluorescent Indicator for Heavy Metal Ions Incorporating a 5-carboxy-2',7'-difluorofluorescein (106)

To a solution of 5-amino-1,10-phenanthroline (230 mg, 1.1 mmol) in 3 mL DMF is added a solution of 600 mg (1.0 mmol) Compound 102 in 1.5 mL DMF. The yellow reaction mixture is stirred at room temperature for 10 hours and is then added to 75 mL stirring ethyl acetate at 0° C. The resulting colorless precipitate is filtered and washed with 30 mL cold ethyl acetate to give 560 mg of the tetramethyl ester of Compound 106 as a colorless solid.

The tetramethyl ester intermediate is then dissolved in 15 mL 1,4-dioxane and concentrated ammonium hydroxide (0.8 mL) is added in one portion. The reaction mixture is centrifuged and the orange pellet is dissolved in 5 mL pure water, then applied to a column of lipophilic SEPHADEX LH-20 resin and eluted with pure water. Pure column fractions are combined, frozen and lyophilized to give phenanthroline conjugate, dipotassium salt (Compound 106) as an orange powder. $\epsilon=54,479$ $cm^{-1}M^{-1}$ in 10 mM EGTA, 100 mM KCl, 10 mM MOPS buffer at pH 7.20. At a concentration of 1 micromolar, Compound 106 exhibits a 5-fold decrease in emission intensity at 523 nm in the presence of 5 micromolar Cu(I) in 5 mM MOPS buffer at pH 7.2.

Example 108

Preparation of a Nucleotide Conjugate of 2',7'-difluorofluorescein-5-(and-6)-carboxylic Acid To a solution of 2 mg of 5-(3-aminoallyl)-2'-deoxyuridine-5'-triphosphate, ammonium salt (Sigma Chemical) in 100 µL of water is added a solution of 3 mg of Compound 72 (Example 73) in 100 µL of DMF, followed by addition of 5 µL of triethylamine. After the mixture is stirred at room temperature for 3 hours, the solution is evaporated to dryness under vacuum and the residue is purified by chromatography over lipophilic SEPHADEX resin using water for elution. The first green fluorescent fractions are combined and lyophilized to give the fluorescent nucleotide conjugate as an orange solid (Compound 107)

Alternatively a fluorescent conjugate (Compound 108) of deoxyuridine-5'-triphosphate is prepared using 5-(3-amino-1-propynyl)-2'-deoxyuridine-5 '-triphosphate in place of 5-(3-aminoallyl)-2'-deoxyuridine-5'-triphosphate (as described in Hobbs, Jr. et al, supra).

Example 109

Preparation of an Oligonucleotide Conjugate of 2', 4',5',7'-tetrafluorofluorescein-5-(and-6)-carboxylic Acid A sample of 500 µg of a 5'-amine modified, 24-base M13 primer sequence is dissolved in 220 µL 0.1M $NaHCO_3$, pH 8.5. To this is added 1 mg of Compound 65 (Example 66) in 35 μL of DMF. After 16 hours at room temperature, 15 μL of 5M NaCl and 3 volumes of cold 100% ethanol are added. The mixture is cooled to −20° C., centrifuged, the ethanol supernate is decanted, the pellet is briefly rinsed, and the pellet is dissolved in 100 μL H$_2$O. The labeled oligonucleotide is purified by HPLC on a 300 Å C8 reverse phase column using a ramp gradient of 0.1M triethylammonium acetate (pH~7) and acetonitrile (15→60% over 30 min). The desired peak is collected and evaporated to give the fluorescent oligonucleotide.

Example 110

Preparation of a Drug Conjugate of 2', 7'-difluorofluorescein-5-(and-6)-isothiocyanate A fluorescent dopamine D$_2$ antagonist is prepared as follows:

To 10 mg of N-(p-aminophenethyl)spiperone (Amlaiky et al., FEBS LETT, 176, 436 (1984)), and 10 μL N,N-diisopropylethylamine in 1 mL of DMF is added 15 mg of 2',7'-difluorofluorescein-5-(and-6)-isothiocyanate (Compound 76, Example 77). After 3 hours, the reaction mixture is poured into 5 mL of diethylether. The resulting precipitate is collected by centrifigation. This crude product is purified by chromatography on silica gel using 10% methanol in chloroform to give the pure product as an orange solid.

Example 111

Protein Conjugates of Fluorinated Dyes

A series of dye conjugates of goat anti-mouse IgG or streptavidin are prepared separately using the reactive dyes 6-carboxymethylthio-2',4,5,7,7'-pentafluorofluorescein, succinimidyl ester (Compound 64), 6-carboxy-2',7'-difluorofluorescein, succinimidyl ester (Compound 61); 9-(4carboxy-2-sulfophenyl)- 2,7-difluoro-6-hydroxy-3H-xanthene-3-one, succinimidyl ester; and fluorescein isothiocyanate (FITC) as follows:

A fresh solution of the desired protein is prepared at 10 mg/mL in 0.1M sodium bicarbonate. The labeling reagents are dissolved in DMF to give a concentration of 10 mg/mL. Predetermined amounts of the labeling reagents are slowly added to the protein solutions with stirring. A molar ratio of 10 equivalents of dye to equivalent of protein is typical, though the optimal amount varies with the particular labeling reagent and the protein being labeled. The reaction mixture is incubated at room temperature for one hour, or on ice for several hours. The dye-protein conjugate is separated from free unreacted reagent by size exclusion chromatography on a CELLUFINE GH-25 column equilibrated with PBS. The initial, protein-containing colored band is collected from the column and the degree of labeling is determined by measuring the absorbance at the absorbance maximum of each fluorophore, using the extinction coefficient of 68,000 cm$^{-1}$M$^{-1}$ for fluorescein at pH 8, and of 70,000 cm$^{-1}$M$^{-1}$ for the other three fluorinated fluorophores at their absorption maxima. The protein concentration is determined by reading at 280 nm and by correcting the value by the percentage of the dye absorption at the same wavelength.

Example 112

Total Fluorescence of Selected Dye-protein Conjugates as a Function of Degree of Substitution A series of goat anti-mouse IgG conjugates is prepared using the reactive dyes 6-carboxymethylthio-2',4,5,7,7'-pentafluorofluorescein, succinimidyl ester (Compound 64), 2',7'-difluoro-6-carboxyfluorescein, succinimidyl ester (Compound 61); 9-(4-carboxy-2-sulfophenyl)-2,7-difluoro-6-hydroxy-3H-xanthene-3-one, succinimidyl ester; and fluorescein isothiocyanate (FITC) so as to yield derivatives with similar degrees of substitution. Fluorescence of the conjugates of the fluorinated fluoresceins is higher than that of FITC. Furthermore, fluorescence of antibody conjugates of 6-carboxymethylthio-2',4,5,7,7'-pentafluorofluorescein and 9-(4-carboxy-2-sulfophenyl)-2,7-difluoro-6-hydroxy-3H-xanthene-3-ol-6-one do not quench appreciably, even at high degrees of substitution (as shown in FIG. 1). Similar results are found with conjugates of 6-carboxymethylthio-2',4,5,7,7'-pentafluorofluorescein, succinimidyl ester and other proteins.

Example 113

Labeling β-galactosidase with a Fluorinated Dluorescein Diacetate

*Escherichia coli* β-galactosidase (3 mg) in 150 μL phosphate-buffered saline pH 7.5 is treated with 13.6 μL of a 1 mg/mL stock solution of 4,5,6,7-tetrafluorofluorescein diacetate (Compound 25) in DMSO. After 1 hour the pH is raised to 10 with Na$_2$CO$_3$ for 2 hours to remove the acetates. Unreacted dye is removed on a spin column. The degree of substitution is estimated at 8.6 using ε=85,600 cm$^{-1}$M$^{-1}$ at 515 nm. Direct labeling of β-galactosidase with 4,5,6,7-tetrafluorofluorescein at the same molar ratio of dye to protein results in minimal protein labeling.

Example 114

Labeling and Use of Wheat Germ Agglutinin with 2',7'-difluorofluorescein

Wheat germ agglutinin (25 mg, EY Laboratories) is dissolved in 5 mL sodium carbonate buffer pH 9.0 containing 5 mM N-acetylglucosamine to protect the active site. To this is added 3.5 mg of 2',7'-difluorofluorescein-5-(and-6)-isothiocyanate (Compound 76). After 1 hr at room temperature the solution is purified as in Example 111. The yellow solution corresponding to the product band is lyophilized and a degree of substitution of 2–3 dyes per molecule is determined from the absorption at 490 nm. When used according to Sizemore etal. (U.S. Pat. No. 5,137,810) the conjugate can distinguish between Gram positive and Gram negative bacteria.

Example 115

Preparation of a Phalloidin Conjugate of 6-carboxymethylthio-2',4,5,7,7'-pentafluorofluorescein This phalloidin conjugate (Compound 109) is prepared exactly analogously to the phalloidin conjugate of Example 74 (Compound 73), excepting that the succinimidyl ester of 6-carboxymethylthio-2',4,5,7,7'-pentafluorofluorescein (Compound 64, Example 65) is used in place of 5-(and-6)-carboxy-2',7'-difluorofluorescein, succinimidyl ester.

Example 116

Labeling of Actin Filaments with Compound 109 and Photobleaching

CRE BAG 2 fibroblasts are fixed with formaldehyde, permeabilized with acetone and then stained with the fluorescent phallotoxins fluorescein phalloidin and Compound 109 (Example 115 above). The stained cells exhibit green fluorescent F-actin filaments. Each sample is continuously illuminated and viewed on a fluorescence microscope using an Omega® Optical fluorescein longpass optical filter set (O-5717), a Star 1™ CCD camera (Photometrics) and Image-1® software (Universal Imaging Corp.). Relative photobleaching, as shown in FIG. 4, clearly demonstrates the superior photostability of the fluorinated dye-conjugate.

Once the F-actin filaments are stained, additional cellular components are optionally stained using other dye-conjugates having spectral properties that are readily distinguishable from those of the fluorinated dye-conjugate. For example, cell nuclei are stained fluorescent blue using DAPI, while cell antigens are stained red using a fluorescent antibody conjugates of a rhodamine or carbocyanine dye, such as TEXAS RED dye (Molecular Probes, Inc., Eugene, Oreg.) or CY-5 dye (Jackson Immunoresearch), respectively. Both the staining and subsequent visualization of the discrete cell components may be performed simultaneously or sequentially.

Example 117

Preparation and use of a Fluorescent α-bungarotoxin

α-Bungarotoxin (1 mg) in 25 μL 0.1M $NaHCO_3$ is treated with 1.5 equivalents of 6-carboxymethylthio-4,5,7-trifluorofluorescein, succinimidyl ester (Compound 63, Example 64) at room temperature for 2 hours. The product is purified by size exclusion and ion exchange chromatography on a CM-SEPHADEX resin column. The product-containing fractions are lyophilized to yield a yellow solid. Staining of acetylcholine receptors and detection of their resulting fluorescence is comparable to that of fluorescein-conjugated α-bungarotoxin, except that the fluorescence of the fluorinated dye-conjugate is more resistant to photobleaching.

Example 118

Preparation of a Dextran Conjugate of 5-(and-6)-amino-2',7'-difluorofluorescein 5-(And-6)-amino-2',7'-difluorofluorescein is treated with cyanuric chloride (2,4,6-trichloro-1,3,5-triazine) to yield the dichlorotriazine adduct (Compound 110), which is then used to label the free hydroxyl groups of a polysaccharide. A 70,000 MW dextran (50 mg) is dissolved in 2.5 mL of 0.2M sodium carbonate buffer (pH 9.5). Compound 110 (20 mg in 1 mL DMSO) is added. The solution is heated to 50° C. for 6 hours while maintaining the pH at 9.5–10.0 with aliquots of 1M NaOH. The dye-dextran conjugate is purified on SEPHADEX G-15 resin by eluting with 30 mM ammonium acetate. The first colored band to elute from the column is collected and lyophilized.

Example 119

Preparation of Aminodextran Conjugates of Fluorinated Fluoresceins 70,000 MW aminodextran (50 mg) that is derivatized with an, average of 13 amino groups, is dissolved at 10 mg/mL in 0.1M $NaHCO_3$. A succinimidyl ester derivative of the desired fluorinated dye is added in an amount sufficient to give dye/dextran ratio of 12. After 6 hours at room temperature, the conjugate is purified on SEPHADEX G-50 resin eluting with water and the product is lyophilized. Typically ~6 moles of dye is conjugated to 70,000 g dextran.

Example 120

Preparation of Fluorescent-dye Labeled Microspheres

Four methods are used to prepare fluorescent microspheres. In Method A, 1.0 μm uniform amine-derivatized polystyrene microspheres are suspended at 2% solids in 100 mM bicarbonate buffer pH 8.3 and treated with 2 mg/mL of an amine-reactive fluorinated dye such as a succinimidyl ester derivative (for example, Compounds 61–67 and 72). After 1 hour the microspheres are separated by centrifugation and washed with buffer. In Method B, carboxylate-modified microspheres are suspended in a solution of a protein that has been conjugated to a fluorinated dye. Excess protein is removed by centrifugation and washing. Microparticles of a size that cannot be centrifuged are separated from protein by dialysis through a semi-permeable membrane with a high MW cutoff or by gel filtration chromatography. In Method C the protein is covalently coupled through its amine residues to the carboxylate groups of the polymer using ethyl 3-(dimethylaminopropyl)carbodiimide (EDAC). In Method D, biotinylated microspheres (Molecular Probes, Inc) are treated with a streptavidin, avidin or anti-biotin conjugate of a fluorinated dye and the conjugates are isolated as in Method B. The larger particles can be analyzed for uniformity of staining and brightness using flow cytometry and are useful as standards for microscopy and flow cytometry as well as detection reagents.

Example 121

Preparation of Fluorescent Liposomes

Fluorescent liposomes containing polar derivatives, including 5-carboxy-2',7'-difluorofluorescein (Compound 36) and 2',7'-difluorocalcein (prepared by hydrolysis of Compound 99, Example 99) on their interior are prepared and used essentially as described in J. BIOL. CHEM. 257, 13892 (1982) and PROC. NATL. ACAD. SCI. USA 75, 4194 (1978). Alternatively, liposomes containing lipophilic fluorinated fluoresceins within their membranes such as Compound 79 are prepared by codissolving the fluorescent lipid and the unlabeled phospholipid(s) that make up the liposome before forming the liposome dispersion essentially as described by Szoka, Jr. et al. (ANN. REV. BIOPHYS. BIOENG. 9, 467 (1980)).

Example 122

Preparations of a Fluorescent Low Density Lipoproteins

Covalent conjugates of human low density lipoproteins (LDL), which are known to be taken up by macrophage, endothelial and other cells that possess "scavenger" receptors specific for the modified LDL, are prepared essentially as described in Example 111 with purification by gel filtration. Binding of the fluorescent conjugates can be detected by either fluorescence microscopy or flow cytometry. Alternatively, LDL labeled in its lipid domain can be prepared by simple incubation of the LDL with the lipophilic fluorescent dye dispersed in buffer, followed by gel filtration.

Example 123

Preparation of Fluorescent Conjugates of Bacteria

Heat-killed *Escherichia coli* are suspended at 10 mg/mL in pH 89 buffer then incubated with 0.5–1.0 mg/mL of an amine-reactive fluorinated dye. After 3060 minutes the labeled bacteria are centrifuged and washed several times with buffer to remove any unconjugated dye. Labeled bacteria that are opsonized are taken up by macrophage, as determined by flow cytometry.

Example 124

Utility of Protein Conjugates as Immunoreapents and Resistance to Photobleaching Antibody conjugates of the succinimidyl esters of 6-carboxymethylthio-2',4,5,7,7'-pentafluorofluorescein (Compound 59), 9-(4-carboxy-2-sulfophenyl)-2,7-difluoro-6-hydroxy-3H-xanthene-3-ol-6-one, 6-carboxy-2',7'-difluorofluorescein and fluorescein are prepared with degrees of substitution of approximately 4–6. INOVA slides are rehydrated in 1% bovine serum albumin (BSA) in phosphate buffered saline (PBS) for 30 minutes. The slide is drained thoroughly. Human autoantibody is applied and the slide is incubated 30 minutes and rinsed thoroughly in PBS. Mouse anti-human antibody is applied and the slide is incubated 30 minutes and rinsed, thoroughly in PBS. Each green fluorescent goat anti-mouse antibody conjugate is applied as a solution that is 10 $\mu$g/mL, diluted in 1% BSA/PBS. The slides are incubated for 30 minutes. The labeled slides are then rinsed thoroughly in PBS, then rinsed in 50 mM Tris pH 8.0, mounted in 50 mM Tris pH 8.0, and viewed through a longpass fluorescein filter. All samples give predominantly nuclear staining. One image of the slide is acquired every 5 seconds for 100 seconds with coninuous illumination of the specimen, using a fluorescein long-pass filter. Three fields of cells are bleached using this method, and the photobleaching values are normalized and averaged. The average of three runs for each conjugate is then normalized and plotted. The results are shown in FIG. 2. It is observed that antibody conjugates of the fluorinated dyes are significantly more photostable than the fluorescein conjugate.

Example 125

Preparing a DNA Hybridization Probe using Fluorescent Nucleotide Conjugates For each labeling reaction, a microfuge tube containing about 1 $\mu$g of a ~700 bp Hind III-Bgl II fragment of the *E. coli* lacZ structural gene is heated for ~10 minutes at 95° C. to fully separate the strands. The DNA is immediately cooled on ice, to prevent the strands from reannealing. To the DNA mixture on ice is added 2 $\mu$L of a 2 mg/mL mixture of random sequence hexanucleotides, in 0.5M Tris-HCl, pH 7.2, 0.1M MgCl$_2$, 1 mM dithiothreitol; 2 $\mu$L of a DNTP labeling mixture (1 mM DATP, 1 mM dGTP, 1 mM dCTP, 0.65 mM dTTP and 0.35 mM either Compound 107 or Compound 108 (Example 108). Sterile distilled, deionized water is added to bring the total volume of each sample to 19 $\mu$L. A 1 $\mu$L volume of Klenow DNA polymerase (2 units/$\mu$L) is added carefully to the samples and they are mixed by pipetting up and down repeatedly. The samples are incubated for one hour at 37° C. The reactions are stopped by adding 2 $\mu$L of 0.2M EDTA, pH 8.0. The labeled DNA is precipitated by addition of 2.5 $\mu$L of 4M LiCl and 75 $\mu$L prechilled (−20° C.) 100% ethanol and mixing well. Precipitation is allowed to continue for 2 hours at −20° C. and the nucleic acids are then recovered by centrifugation at 12,000 rpm in a microfuge. The pellets are washed briefly with cold 70% ethanol, then with cold 100% ethanol. The pellets are dried briefly and dissolved in 10 mM Tris-HCl, pH 8.0, 1 mM EDTA. A portion consisting of 1/10 to 1/2 of each sample is analyzed by gel electrophoresis on a 1% agarose minigel under standard conditions. The labeled DNA products are suitable for in situ hybridization experiments for the detection of RNA or DNA, such as is associated with the *E. coli* lacZ gene in cells or tissues.

Example 126

Incorporation of Fluorescent Nucleotide Conjugates into DNA Amplification Products A DNA amplification reaction is prepared as follows. 1 $\mu$L each of 20 $\mu$M solutions of two oligonucleotide primers that hybridize to the human $\beta$-actin gene (Human $\beta$-Actin Control Amplimer Set, CLONTECH Laboratories, Inc, Palo Alto, Calif.) are added to a labeling reaction containing 5 $\mu$L DNA template (100 pmol of a plasmid containing the entire gene), 5 $\mu$L 10× reaction buffer (100 mM Tris, pH 8.3, 500 mM KCl), 2.5 $\mu$L 1 mM Compound 107 (fluorescent dUTP), 1 $\mu$L 10 mM dATP, 1 $\mu$L 10 mM dCTP, 1 $\mu$L 10 mM dGTP, 1.5 $\mu$L 5 mM dTTP, 3 $\mu$L 25 mM MgCl$_2$, and 28 $\mu$L distilled, deionized water. The sample is transferred to a commercially available thermocycler and processed according to the following program: one cycle, 94° C., 2.5 minutes; 30 cycles, 94° C., 1 minute, 50° C. 1 minute, 72° C., 1 minute; one cycle, 72° C., 5 minutes; then 4° C. overnight. An aliquot consisting of 10% of the sample (5 $\mu$L) is mixed with an equal volume of 10% glycerol and loaded onto a 0.9% agarose minigel. Samples are electrophoresed until the bromophenol blue in size markers in an adjacent gel migrates at least half of the length of the gel. Green fluorescent bands of the expected size are visible when the gel is illuminated with 300 nm ultraviolet light, as is a diffuse band containing unincorporated dUTP conjugate.

Example 127

In situ Hybridization of an RNA Probe Prepared using Fluorescent Nucleotide Conjugates Mouse fibroblasts are fixed and prepared for MRNA in situ hybridization using standard procedures. A fluorophore-labeled RNA probe is prepared by in vitro transcription of a plasmid containing the mouse actin structural gene cloned downstream of a phage T3 RNA polymerase promoter. Labeling reactions consist of combining 2 $\mu$L DNA template (1 $\mu$g DNA), 1 $\mu$L each of 10 mM ATP, CTP and GTP, 0.75 $\mu$L 10 mM UTP, 2.5 $\mu$L 1 mM 2',7'-difluorofluorescein-5-(and-6)-carboxylic acid conjugate of UTP (Prepared as in Example 8, only using 5-(3-aminoallyl)-uridine-5'-triphosphate, ammonium salt (Sigma Chemical) in place of 5-(3-aminoallyl)2'-deoxyuridine-5'-triphosphate, ammonium salt), 2 $\mu$L 10× transcription buffer (400 mM Tris, pH 8.0, 100 mM MgCl$_2$, 20 mM spermidine, 100 mM NaCl), 1 $\mu$L T3 RNA polymerase (40 units/$\mu$L), 1 $\mu$L 2 mg/ml bovine serum albumin, and 8.75 $\mu$L water. Reactions are incubated at 37° C. for two hours.

The DNA template is removed by treatment of the reaction with 20 units DNase I for 15 minutes, at 37° C. The RNA transcript is then purified by extraction with an equal volume of phenol:chloroform, 1:1, then by chromatography through a G50 gel filtration column. Labeled RNA is denatured by heating for 5 minutes at 50° C., then hybridized to cellular preparations using standard procedures. When preparations are washed and viewed through a fluorescein filter set on a fluorescence microscope, cells expressing actin mRNA show bright green fluorescence.

Example 128

The Use of 2',7'-difluorofluorescein Diphosphate (DFFDP) for the Detection of Acid Phosphatase Activity

The rate of fluorescent product generation is measured by exciting a solution of 10 µM DFFDP or fluorescein diphosphate (FDP) at 490 nm while monitoring the emission at 515 nm in a fluorometer in the presence of 0.1 units of prostatic acid phosphatase at pH 5. Under these conditions, acid phosphatase produces about a 6.5 times greater change in signal using DFFP than FDP.

Example 129

The Use of 2',7'-difluorofluorescein Digalactoside (DFFDG) for the Detection of Acid β-galactosidase Activity

The fluorescence resulting from the action of acid β-galactosidase from bovine testes on fluorescein digalactoside (FDG) and DFFDG is compared. The fluorescence increase at 512 nm when excited at 490 nm is measured versus time for 50 µM substrate with 4.6 nM enzyme in assay buffer (200 mM sodium phosphate +75 mM citric acid, pH 4.5). The initial rate of fluorescence production from DFFDG is 3.0 times that obtained using FDG.

Example 130

The Use of 4,5,7-trifluoro-6-methoxyfluorescein Digalactoside (TFMFDG) and 4,5,6,7-tetrafluorofluorescein Digalactoside (TFFDG) for the Detection of Endogenous (Lysosomal) β-galactosidase Activity in Intact Cells

NIH 3T3 cells that are not transfected with exogenous β-galactosidase were cultured in Dulbecco's Modified Minimal Essential Medium supplemented with 10% fetal bovine serum and 2 mM L-glutamine. Stock solutions of TMFDG and TFFDG in phosphate buffered saline (PBS) are added to the cell culture medium to obtain a fmal dye concentration of 1 µM. The cells are incubated at 37° C. for 30 minutes, put on ice and assayed immediately by flow cytometry using a FACS-Vantage instrument equipped with an argon-ion laser (488 nm excitation). Fluorescence emission is collected using a 515 nm long-pass filter and a single photomultiplier tube. Fluorescence signals normalized for the known fluorogenic substrate FDG show that TFMFDG and TFFDG give signals 48.1 and 4.1 times that of FDG, respectively (Table 4).

TABLE 4

| Substrate | Fluorescence Emission |
|---|---|
| FDG | 1.0 |
| TFFDG | 4.1 |
| TFMFDG | 48.1 |

Example 131

The Use of 4,5,6,7-tetrafluorodihydrofluorescein (TFDHF) for the Detection of Horseradish Peroxidase (HRP) Activity in Vitro

A 2 mM solution (0.5 mL) of TFDHF is prepared in water. OPD buffer (0.5M Phosphate-citrate buffer) without hydrogen peroxide (pH 5.5, 0.5 mL) is added, resulting in a 1 mM concentration of substrate. Minor background fluorescence, indicating the presence of some contaminating oxidized dye, serves to provide a fluorescence signal at time 0. To another 0.5 mL of a 2 mM solution of TFDHF is added OPD buffer with hydrogen peroxide (0.5 mL), causing no detectable fluorescence increase. Addition of HRP (1 µL, $10^{-4}$ Units) causes an immediate production of bright yellow fluorescence. After incubation at room temperature in darkness for 25 minutes, the reaction solution is diluted 1:20 into potassium phosphate buffer at pH 8, and fluorescence emission spectra are recorded.

Example 132

Cell Labeling with a Fluorinated Fluorescein Diacetate

Cells from a human lymphoid B-cell culture in RPMI 1640 medium are treated with 1 µM Compound 25 (4,5,6,7-TFFDA), Compound 26 (2',4,5,6,7,7'-HFFDA), or fluorescein diacetate (FDA) at 37° C. for 30 minutes- Following centrifugation and washing in PBS, the pellets are resuspended in RPMI 1640 medium for 15 min, recentrifuged and washed in PBS, fixed with 3.7% formaldehyde in PBS and analyzed by flow cytometry using 488 nm excitation. Cells stained with Compounds 25 and 26 show significantly higher fluorescence than those stained with FDA after two hours (FIG. 5). Fluorescence in the cells can be detected for at least 24 hours and the dye does not transfer to other cells when the labeled cells are mixed with unlabeled cells. Cells stained with 2',4',5',7'-tetrafluorofluorescein diacetate are also weakly fluorescent. Alternatively, the stained and washed cells are viewed or analyzed without fixation.

Example 133

Detection of Products of Fluorinated Dyes in Cells

Cells that have been stained with 4,5,6,7-TFFDA (Compound 25) as in Example 132 are gently lysed using PBS with 0.1% NP40. After removal of debris by centrifugation at 400×g for 5 minutes, the supernatant is spin filtered by centrifugation for 30 minutes at 15,000×g. The resulting filtrate is than analyzed using HPLC. The fluorescent products in the retained fraction are shown to contain both 4,5,6,7-tetrafluorofluorescein and its glutathione adduct (retention times 14.7 minutes and 11.6 minutes, respectively, as confirmed by BPLC of reference compounds prepared separately using 4,5,6,7-TFFDA). Using SDS gel electrophoresis, the cell lysate is shown to contain several proteins, only some of which are fluorescent.

Example 134

Use of Cell Labeled with 4,5,6,7-TFFDA to Assess Efflux Mechanisms

Identical batches of lymphoid-B cell lines cells are separately incubated with 1 µM solutions of 4,5,6,7-tetrafluorofluorescein diacetate (Compound 25), 2',7'-dichloro-4,5,6,7-tetrafluorofluorescein diacetate (Compound 28), 2',4,5,6,7,7'-hexafluorofluorescein diacetate (Compound 27) and 2',4',5',7'-tetrafluorofluorescein diacetate. To one set of each cells is added 100 µM verapamil and to another 1 mM probenecid, both of which are known to block ATP-dependent dye efflux mechanisms, as found in multidrug resistant of cells. Without washing, the cells are analyzed for brightness by flow cytometry using 488-nm excitation. Results (Table 5) show that all four dyes are useful for detecting the effect of the drugs on efflux and that TFFDA has the highest intrinsic fluorescence under these conditions.

TABLE 5

Inhibition of dye efflux mechanisms by verapamil and probenecid

| | Mean Fluorescence intensity of labeled cells | | | |
|---|---|---|---|---|
| DYE | No dye | No drug | 100 μM verapamil | 1 mM Probenecid |
| 4,5,6,7-TFFDA | 1.3 | 732 | 1892 | 2521 |
| 2',7'-DCTFFDA | 1.3 | 15.6 | 110 | 80.6 |
| 2',4,5,6,7,7'-HFFDA | 1.3 | 26.9 | 212 | 172 |
| 2',4',5',7'-TFFDA | 1.3 | 2.9 | 14.0 | 12.8 |

Example 135

Quenching of the Fluorescence of 2',7'-difluorofluorescein by Rabbit Polyclonal Anti-fluorescein IgG (H+L) Fraction Solutions of 5×10⁻⁹M fluorescein and 5×10⁻⁹M 2',7'-difluorofluorescein (Compound 29) are prepared in 100 mM potassium phosphate buffer, pH 8.0. The fluorescence of each solution is read with excitation at 490 nm. Sequential additions of 0.5 mg/mL rabbit polyclonal anti-fluorescein IgG (H+L) fraction (Molecular Probes, Inc.) are added and the fluorescence measurements are repeated. The intensities recorded are in Table 6:

TABLE 6

| Antibody | Fluorescence Intensity | |
|---|---|---|
| volume (μL) | fluorescein | 2',7'-difluorofluorescein |
| 0 | 100% | 100% |
| 2 | 84.6% | 83.6% |
| 4 | 68.8% | 67.3% |
| 6 | 54.3% | 51.9% |
| 8 | 38.5% | 36.5% |
| 10 | 22.9% | 23.8% |
| 12 | 11.7% | 13.4% |
| 15 | 4.4% | 6.3% |

The results show virtually identical binding and quenching of the two dyes.

Example 136

Procedure for pH Titration of Fluorinated Fluorophores

The dye of interest is first dissolved in a series of buffers that have each been calibrated using a pH meter. Acetate buffers are typically used in the range of pH 4–6, and phosphate buffers in the pH range 6–8. Absorption measurements are made using solutions that are approximately 10 μM in concentration, and fluorescence measurements are made using solutions that are approximately 1 μM in concentration. The absorption or emission data is then plotted versus pH to determine pKa values. For example, FIG. 3 shows the fluorescence emission data for 2',7'-difluorofluorescein (pK$_a$ ~4.7) and fluorescein (pK$_a$ ~6.4) plotted versus the pH of the solution. The data shows that fluorination of the fluorophore has lowered the pKa of fluorescein significantly. The pKa of the fluorinated fluorescein is even lower than that of 2',7'-dichlorofluorescein (pK$_a$ ~5.1).

It is to be understood that, while the foregoing invention has been described in detail by way of illustration and example, numerous modifications, substitutions, and alterations are possible without departing from the spirit and scope of the invention as described in the following claims.

What is claimed is:

1. A compound having the formula

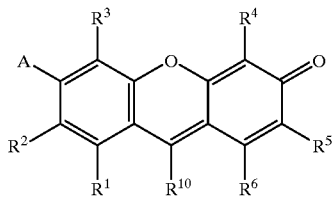

or the formula

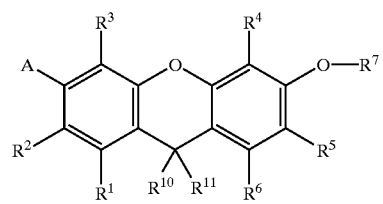

wherein $R^1$ and $R^6$ are independently H, F, Cl, Br, I, $C_1$–$C_{18}$ alkyl or $C_1$–$C_{18}$ alkoxy;

$R^2$, $R^3$, $R^4$ and $R^5$ are independently H, F, Cl, Br, I, CN; or $C_1$–$C_{18}$ alkyl, $C_1$–$C_{18}$ alkoxy or $C_1$–$C_{18}$ alkylthio, where each alkyl, alkoxy or alkylthio is optionally further substituted by F, Cl, Br, I, sulfonic acid, salt of sulfonic acid, carboxylic acid, a salt of carboxylic acid, a carboxylic acid ester of a $C_1$–$C_6$ alkyl, a carboxylic acid ester of —CH$_2$—O—(C=O)—R$^{18}$ where R$^{18}$ is a $C_1$–$C_4$ alkyl; or amino, alkylamino, dialkylamino, or alkoxy, the alkyl portions of which independently have 1–6 carbons; or one or both of $R^3$ and $R^4$ are —CH$_2$N(CH$_2$COOR$^{17}$)$_2$, where R$^{17}$ is H, a biologically compatible counterion, a linear or branched alkyl having 1–6 carbons, or —CH$_2$—O—(C=O)—R$^{18}$;

A is OR$^7$ or NR$^8$R$^9$, where each R$^7$ is independently H, $C_1$–$C_{18}$ alkyl, a $C_1$–$C_{18}$ acyl wherein each alkyl group independently has 1–6 carbons and is optionally substituted by amino, hydroxy, carboxylic acid, a salt of carboxylic acid, a carboxylic acid ester of a $C_1$–$C_6$ alkyl, a carboxylic acid ester of —CH$_2$—O—(C=O)—R$^{18}$; or a trialkylsilyl wherein each alkyl group independently has 1–6 carbons;

R$^8$ and R$^9$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, a salt of $C_1$–$C_6$ sulfoalkyl, or $C_1$–$C_{18}$ acyl wherein the alkyl portions are optionally substituted by amino, hydroxy, carboxylic acid, a salt of carboxylic acid, a carboxylic acid ester of a $C_1$–$C_6$ alkyl, a carboxylic acid ester of —CH$_2$—O—(C=O)—R$^{18}$; or R$^8$ in combination with R$^2$, or R$^9$ in combination with R$^3$, or both, form a saturated 5- or 6-membered ring that is optionally substituted by one or more methyls; or R$^8$ in combination with R$^9$ forms a saturated 5- or 6-membered heterocycle that is a piperidine, a morpholine, a pyrrolidine or a piperazine, each of which is optionally substituted by methyl, carboxylic acid, a salt of carboxylic acid, a carboxylic acid ester of a $C_1$–$C_6$ alkyl, or a carboxylic acid ester of —$CH_2$—O—(C=O)—$R^{18}$;

$R^{10}$ is F, carboxylic acid, a salt of carboxylic acid, a carboxylic acid ester of a $C_1$–$C_6$ alkyl, or a carboxylic acid ester of —$CH_2$—O—(C=O)—$R^{18}$; or $R^{10}$ is $C_1$–$C_{18}$ alkyl, alkenyl or alkynyl that is optionally substituted one or more times by F, Cl, Br, carboxylic acid, a salt of carboxylic acid, a carboxylic acid ester of a $C_1$–$C_6$ alkyl, a carboxylic acid ester of —$CH_2$—O—(C=O)—$R^{18}$, sulfonic acid, salt of sulfonic acid, amino, alkylamino, or dialkylamino, the alkyl groups of which have 1–6 carbons; or $R^{10}$ has the formula

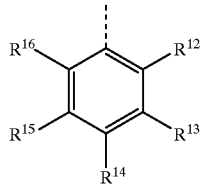

where $R^{12}$, $R^{13}$, $R^{14}$, $R^{15}$ and $R^{16}$ are independently H, F, Cl, Br, I; or sulfonic acid, salt of sulfonic acid, carboxylic acid, a salt of carboxylic acid, a carboxylic acid ester of a $C_1$–$C_6$ alkyl, a carboxylic acid ester of —$CH_2$—O—(C=O)—$R^{18}$, CN, nitro, hydroxy, azido, amino, hydrazino; or $C_1$–$C_{18}$ alkyl, $C_1$–$C_{18}$ alkoxy, $C_1$–$C_{18}$ alkylthio, $C_1$–$C_{18}$ alkylamino, $C_1$–$C_{18}$ alkylester, $C_1$–$C_{18}$ alkylamido or $C_1$–$C_{18}$ arylamido, the alkyl or aryl portions of which are optionally substituted one or more times by F, Cl, Br, I, hydroxy, carboxylic acid, a salt of carboxylic acid, a carboxylic acid ester of a $C_1$–$C_6$ alkyl, a carboxylic acid ester of —$CH_2$—O—(C=O)—$R^{18}$, sulfonic acid, salt of sulfonic acid, amino, alkylamino, dialkylamino or alkoxy, the alkyl portions of each having 1–6 carbons; or one pair of adjacent substituents $R^{13}$ and $R^{14}$, $R^{14}$ and $R^{15}$ or $R^{15}$ and $R^{16}$, when taken in combination, form a fused 6-membered aromatic ring that is optionally further substituted by carboxylic acid, a salt of carboxylic acid, a carboxylic acid ester of a $C_1$–$C_6$ alkyl, a carboxylic acid ester of —$CH_2$—O—(C=O)—$R^{18}$; and $R^{11}$ is H, hydroxy, CN or a $C_1$–$C_6$ alkoxy; or $R^{10}$ in combination with $R^{11}$ forms a 5-membered spirolactone ring or a 5-membered spirosultone ring; or $R^{11}$ in combination with $R^{12}$ forms a 5- or 6-membered spirolactone ring or a 5- or 6-membered spirosultone ring that is optionally and independently substituted by H, F or $CH_3$; or $R^{10}$ when taken in combination with $R^{11}$ is a carbonyl oxygen;

provided that at least one of $R^1$, $R^2$, $R^3$, $R^4$, $R^5$, $R^6$, and $R^{10}$ is F, or at least three of $R^{12}$, $R^{13}$, $R^{14}$, $R^{15}$ and $R^{16}$ are F.

2. A compound, as claimed in claim 1, wherein at least one of $R^2$, $R^3$, $R^4$ or $R^5$ is F.

3. A compound, as claimed in claim 2, wherein $R^2$ and $R^5$ are F.

4. A compound, as claimed in claim 2, wherein at least one of $R^{12}$, $R^{13}$, $R^{14}$, $R^{15}$, or $R^{16}$ is F.

5. A compound, as claimed in claim 2, wherein none of $R^{12}$, $R^{13}$, $R^{14}$, $R^{15}$, or $R^{16}$ is F.

6. A compound, as claimed in claim 1, wherein at least one of $R^{12}$, $R^{13}$, $R^{14}$, $R^{15}$, or $R^{16}$ is F.

7. A compound, as claimed in claim 6, wherein each of $R^{13}$, $R^{14}$, $R^{15}$, and $R^{16}$ is F.

8. A compound, as claimed in claim 6, wherein none of $R^1$, $R^2$, $R^3$, $R^4$, $R^5$ or $R^6$ is F.

9. A compound, as claimed in claim 1, wherein A is $OR^7$.

10. A compound, as claimed in claim 9, wherein each $R^7$ is H.

11. A compound, as claimed in claim 10, wherein at least one of $R^1$, $R^2$, $R^3$, $R^4$, $R^5$ or $R^6$ is F; and $R^{11}$ is H.

12. A compound, as claimed in claim 10, wherein at least one of $R^{12}$, $R^{13}$, $R^{14}$, $R^{15}$ or $R^{16}$ is F; and $R^{11}$ is H.

13. A compound, as claimed in claim 1, wherein $R^{12}$ is carboxylic acid or a salt of carboxylic acid.

14. A compound, as claimed in claim 1, wherein A is $NR^8R^9$.

15. A compound, as claimed in claim 1, wherein $R^1$ and $R^6$ are independently H or F.

16. A compound, as claimed in claim 1, wherein $R^{12}$ is sulfonic acid or a salt of sulfonic acid.

17. A compound, as claimed in claim 1, wherein each of substituents $R^1$, $R^2$, $R^3$, $R^4$, $R^5$, $R^6$, $R^{13}$, $R^{14}$, $R^{15}$ and $R^{16}$ are either F or H and at least one of $R^1$, $R^2$, $R^3$, $R^4$, $R^5$, $R^6$, $R^{13}$, $R^{14}$, $R^{15}$ and $R^{16}$ is F.

18. A compound, as claimed in claim 1, wherein $R^1$ and $R^6$ are H and $R^2$, $R^3$, $R^4$, $R^5$ are independently H, F, Cl, Br or I.

19. A compound, as claimed in claim 1, wherein $R^{10}$, when taken in combination with $R^{11}$, is a carbonyl oxygen.

20. A compound, as claimed in claim 1, wherein A is $OR^7$, and one or both of $R^3$ and $R^4$ are —$CH_2N(CH_2COOR^{17})$.

21. A compound, as claimed in claim 1, having the formula

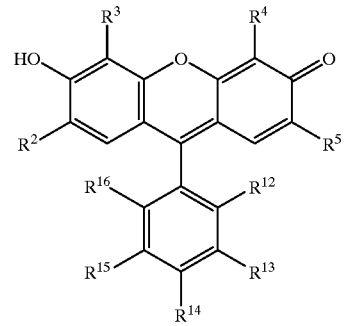

wherein $R^2$, $R^3$, $R^4$ and $R^5$ are independently H or F;

$R^{12}$ is carboxylic acid, a salt of carboxylic acid, a carboxylic acid ester of a $C_1$–$C_6$ alkyl, a carboxylic acid ester of —$CH_2$—O—(C=O)—$R^{18}$, sulfonic acid or a salt of sulfonic acid,;

$R^{13}$, $R^{14}$, $R^{15}$ and $R^{16}$ are independently H, F, carboxylic acid, a salt of carboxylic acid, a carboxylic acid ester of a $C_1$–$C_6$ alkyl, a carboxylic acid ester of —$CH_2$—O—(C=O)—$R^{18}$, sulfonic acid, salt of sulfonic acid, or $C_1$–$C_6$ alkylthio that is optionally substituted by carboxylic acid, a salt of carboxylic acid, a carboxylic acid ester of a $C_1$–$C_6$ alkyl, or a carboxylic acid ester of —$CH_2$—O—(C=O)—$R^{18}$.

22. A compound, as claimed in claim 1, that is 6-amino-9-(2-carboxy-3,4,5,6-tetrafluorophenyl)-3H-xanthene-3-one, 6-amino-9-(2,4-dicarboxyphenyl)-2-fluoro-3H-xanthene-3-one, 6-amino-9-(2,4-dicarboxyphenyl)-7-fluoro-3H-xanthene-3-one, 4',5'-bis((di(carboxymethyl)amino)methyl)-2',7'-difluorofluorescein (2',7'-difluorocalcein), 4',5'-bis((di(carboxymethyl)amino)methyl)-2',7'-difluorofluorescein, acetoxymethyl ester (2',7'-difluorocalcein AM),
6-carboxy-2',7'-difluorodihydrofluorescein, di(acetoxymethyl ester),
4-(carboxymethyl)thio-5,6,7-trifluorofluorescein,
6-(carboxymethyl)thio-4,5,7-trifluorofluorescein,
4-(carboxymethyl)thio-2',5,6,7,7'-pentafluorofluorescein,
6-(carboxymethyl)thio-2',4,5,7,7'-pentafluorofluorescein,
9-(2-carboxyphenyl)-2',7'-difluorodihydrofluorescein,
9-(2-carboxyphenyl)-2',7'-difluorodihydrofluorescein diacetate,
9-(2-carboxyphenyl)-2',4',5',7'-tetrafluorodihydrofluorescein,
9-(4-carboxy-2-sulfophenyl)-2',7'-difluorofluorescein,
4',5'-dichloro-2',7'-dimethoxy-4,5,6,7-tetrafluorofluorescein-5-carboxylic acid,
2',7'-dichloro-4,5,6,7-tetrafluorofluorescein,
1',8'-difluorofluorescein,
2',7'-difluorofluorescein,
2',7'-difluorofluorescein diacetate,
4',5'-difluorofluorescein,
2',7'-difluoro-6-hydroxy-3H-xanthene-3-one,
2',7'-difluorofluorescein-5-carboxylic acid,
2',7'-difluorofluorescein-5-carboxylic acid diacetate,
2',7'-difluorofluorescein-5-carboxylic acid diacetate, acetoxymethyl ester,
2',7'-difluorofluorescein-6-carboxylic acid,
2',7'-difluorofluorescein-5-sulfonic acid,
2',7'-difluorofluorescein-6-sulfonic acid,
2',7'-dimethoxy-4,5,6,7-tetrafluorofluorescein,
2',7'-dimethoxy-4,5,6,7-tetrafluorofluorescein-5-carboxylic acid,
5-dodecanoylamino-2',7'-difluorofluorescein,
2'-fluorofluorescein,
4'-fluorofluorescein,
2',4,5,6,7,7'-hexafluorofluorescein,
2',4,5,6,7,7'-hexafluorofluorescein diacetate,
1,2,4,5,7,8-hexafluoro-6-hydroxy-9-(pentafluorophenyl)-3H-xanthene-3-one,
9-(2-sulfophenyl)-2,7-difluoro-dihydro-9H-xanthene-3,6-diol,
6-hydroxy-9-(2-sulfo-3,4,5,6-tetrafluorophenyl)-3H-xanthene-3-one,
2',4',5',7'-tetrabromo-4,5,6,7-tetrafluorofluorescein,
2',4',5',7'-tetrafluorofluorescein,
2',4',5',7'-tetrafluorofluorescein-5-carboxylic acid,
2',4',5',7'-tetrafluorofluorescein diacetate,
4,5,6,7-tetrafluorofluorescein,
4,5,6,7-tetrafluorofluorescein diacetate,
4,5,6,7-tetrafluorofluorescein-2',7'-dipropionic acid,
4,5,6,7-tetrafluorofluorescein-2',7'-dipropionic acid, acetoxymethyl ester, or
2',4',5',7'-tetraiodo-4,5,6,7-tetrafluorofluorescein.

23. A compound having the formula

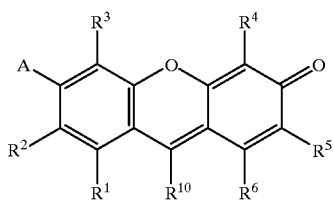

or the formula

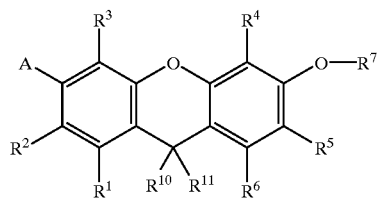

wherein $R^1$ and $R^6$ are independently H, F, Cl, Br, I, $C_1$–$C_{18}$ alkyl or $C_1$–$C_{18}$ alkoxy;

$R^2$, $R^3$, $R^4$ and $R^5$ are independently H, F, Cl, Br, I, CN; or $C_1$–$C_{18}$ alkyl, $C_1$–$C_{18}$ alkoxy or $C_1$–$C_{18}$ alkylthio, where each alkyl, alkoxy or alkylthio is optionally further substituted by F, Cl, Br, I, sulfonic acid, salt of sulfonic acid, carboxylic acid, a salt of carboxylic acid, a carboxylic acid ester of a $C_1$–$C_6$ alkyl, a carboxylic acid ester of —$CH_2$—O—(C=O)—$R^{18}$ where $R^{18}$ is a $C_1$–$C_4$ alkyl; or amino, alkylamino, dialkylamino, or alkoxy, the alkyl portions of which independently have 1–6 carbons; or one or more of $R^2$, $R^3$, $R^4$, and $R^5$ is —L—$R_x$;

A is $OR^7$ or $NR^8R^9$,
where each $R^7$ is independently H, $C_1$–$C_{18}$ alkyl, a $C_1$–$C_{18}$ acyl wherein each alkyl group independently has 1–6 carbons and is optionally substituted by amino, hydroxy, carboxylic acid, a salt of carboxylic acid, a carboxylic acid ester of a $C_1$–$C_6$ alkyl, a carboxylic acid ester of —$CH_2$—O—(C=O)—$R^{18}$; or a trialkylsilyl wherein each alkyl group independently has 1–6 carbons; or $R^7$ is an —L—$R_x$;

$R^8$ and $R^9$ are independently H, $C_1$–$C_6$ alkyl, $C_1$–$C_6$ carboxyalkyl, $C_1$–$C_6$ sulfoalkyl, a salt of $C_{1-C6}$ carboxyalkyl, a salt of $C_1$–$C_6$ sulfoalkyl, or $C_1$–$C_{18}$ acyl wherein the alkyl portions are optionally substituted by amino, hydroxy, carboxylic acid, a salt of carboxylic acid, a carboxylic acid ester of a $C_1$–$C_6$ alkyl, a carboxylic acid ester of —$CH_2$—O—(C=O)—$R^{18}$; or $R^8$ in combination with $R^2$, or $R^9$ in combination with $R^8$, or both, form a saturated 5- or 6-membered ring that is optionally substituted by one or more methyls; or $R^8$ in combination with $R^9$ forms a saturated 5- or 6-membered heterocycle that is a piperidine, a morpholine, a pyrrolidine or a piperazine, each of which is optionally substituted by methyl, carboxylic acid, a salt of carboxylic acid, a carboxylic acid ester of a $C_1$–$C_6$ alkyl, or a carboxylic acid ester of —$CH_2$—O—(C=O)—$R^{18}$; or one of $R^8$ and $R^9$ is —L—$R_x$; and $R^{10}$ is F, carboxylic acid, a salt of carboxylic acid, a carboxylic acid ester of a $C_1$–$C_6$ alkyl, or a carboxylic acid ester of —$CH_2$—O—(C=O)—$R^{18}$; or $R^{10}$ is $C_1$–$C_{18}$ alkyl, alkenyl or alkynyl that is optionally substituted one or more times by F, Cl, Br, carboxylic acid, a salt of carboxylic acid, a carboxylic acid ester of a $C_1$–$C_6$ alkyl, a carboxylic acid ester of —$CH_2$—O—(C=O)—$R^{18}$, sulfonic acid, salt of sulfonic acid, amino, alkylamino, or dialkylamino, the alkyl groups of which have 1–6 carbons; or $R^{10}$ is an —L—$R_x$; or $R^{10}$ has the formula

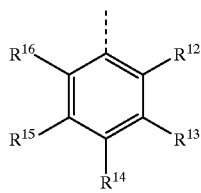

where $R^{12}$, $R^{13}$, $R^{14}$, $R^{15}$ and $R^{16}$ are independently H, F, Cl, Br, I; or sulfonic acid, salt of sulfonic acid, carboxylic acid, a salt of carboxylic acid, a carboxylic acid ester of a $C_1$–$C_6$ alkyl, a carboxylic acid ester of —$CH_2$—O—(C═O)—$R^{18}$, CN, nitro, hydroxy, azido, amino, hydrazino; or $C_1$–$C_{18}$ alkyl, $C_1$–$C_{18}$ alkoxy, $C_1$–$C_{18}$ alkylthio, $C_1$–$C_{18}$ alkylamino, $C_1$–$C_{18}$ alkylester, $C_1$–$C_{18}$ alkylamido or $C_1$–$C_{18}$ arylamido, the alkyl or aryl portions of which are optionally substituted one or more times by F, Cl, Br, I, hydroxy, carboxylic acid, a salt of carboxylic acid, a carboxylic acid ester of a $C_1$–$C_6$ alkyl, a carboxylic acid ester of —$CH_2$—O—(C═O)—$R^{18}$, sulfonic acid, salt of sulfonic acid, amino, alkylamino, dialkylamino or alkoxy, the alkyl portions of each having 1–6 carbons; or one pair of adjacent substituents $R^{13}$ and $R^{14}$, $R^{14}$ and $R^{15}$ or $R^{15}$ and $R^{16}$, when taken in combination, form a fused 6-membered aromatic ring that is optionally further substituted by carboxylic acid, a salt of carboxylic acid, a carboxylic acid ester of a $C_1$–$C_6$ alkyl, a carboxylic acid ester of —$CH_2$—O—(C═O)—$R^{18}$; or one or more of $R^{12}$, $R^{13}$, $R^{14}$, $R^{15}$ and $R^{16}$ is —L—$R_x$;

$R^{11}$ is H, hydroxy, CN or a $C_1$–$C_6$ alkoxy; or $R^{10}$ in combination with $R^{11}$ forms a 5-membered spirolactone ring or a 5-membered spirosultone ring; or $R^{11}$ in combination with $R^{12}$ forms a 5- or 6-membered spirolactone ring or a 5- or 6-membered spirosultone ring that is optionally and independently substituted by H, F or $CH_3$; or $R^{10}$ when taken in combination with $R^{11}$ is a carbonyl oxygen;

provided that at least one of $R^1$, $R^2$, $R^3$, $R^4$, $R^5$, $R^6$, and $R^{10}$ is F, or at least three of $R^{12}$, $R^{13}$, $R^{14}$, $R^{15}$ and $R^{16}$ are F; and further provided that at least one of $R^2$, $R^3$, $R^4$, $R^5$, $R^7$, $R^8$, $R^9$, $R^{10}$, $R^{12}$, $R^{13}$, $R^{14}$, $R^{15}$ and $R^{16}$ is —L—$R_x$, where each —L—$R_x$ is optionally the same or different;

wherein

L is a single covalent bond, or L is a covalent linkage having 1–24 nonhydrogen atoms selected from the group consisting of C, N, O and S and is composed of any combination of single, double, triple or aromatic carbon-carbon bonds, carbon-nitrogen bonds, nitrogen-nitrogen bonds, carbon-oxygen bonds and carbon-sulfur bonds; and $R_x$ is a reactive site.

24. A compound, as claimed in claim 23, wherein $R_x$ is an acrylamide, an activated ester of a carboxylic acid, an acyl azide, an acyl halide, an acyl nitrile, hydroxy, an aldehyde, an alkyl halide, a sulfonate, an amine, an anhydride, an aniline, an aryl halide, an azide, an aziridine, a boronate, a carboxylic acid, a carbodiimide, a diazoalkane, an epoxide, a glycol, a haloacetamide, a halotriazine, a hydrazine, a hydroxylamine, an imido ester, an isocyanate, an isothiocyanate, a ketone, a maleimide, a phosphoramidite, a silyl halide, a sulfonyl halide, or a thiol group.

25. A compound, as claimed in claim 23, wherein exactly one of $R^2$, $R^3$, $R^4$, $R^5$, $R^7$, $R^8$, $R^9$, $R^{10}$, $R^{12}$, $R^{13}$, $R^{14}$, $R^{15}$ or $R^{16}$ is —L—$R_x$.

26. A compound, as claimed in claim 23, wherein $R^{11}$ is H.

27. A compound, as claimed in claim 23, wherein L contains 1–6 carbon atoms.

28. A compound, as claimed in claim 25, wherein L is a single covalent bond.

29. A compound, as claimed in claim 25, wherein exactly one of $R^2$, $R^3$, $R^4$, $R^5$, $R^7$, $R^8$, $R^9$ or $R^{10}$ is —L—$R_x$.

30. A compound, as claimed in claim 25, wherein exactly one of $R^{13}$, $R^{14}$, $R^{15}$ and $R^{16}$ is —L—$R_x$.

31. A compound, as claimed in claim 30, wherein $R_x$ is an acrylamide, an activated ester of a carboxylic acid, an acyl azide, an acyl halide, an acyl nitrile, hydroxy, an aldehyde, an alkyl halide, a sulfonate, an amine, an anhydride, an aniline, an aryl halide, an azide, an aziridine, a boronate, a carboxylic acid, a carbodiimide, a diazoalkane, an epoxide, a glycol, a haloacetamide, a halotriazine, a hydrazine, a hydroxylamine, an imido ester, an isocyanate, an isothiocyanate, a ketone, a maleimide, a phosphoramidite, a silyl halide, a sulfonyl halide, or a thiol group.

32. A compound, as claimed in claim 31, wherein L is a single covalent bond.

33. A compound, as claimed in claim 30, wherein at least one of $R^1$, $R^2$, $R^3$, $R^4$, $R^5$ or $R^6$ is F.

34. A compound, as claimed in claim 30, wherein $R^2$ and $R^5$ are F.

35. A compound, as claimed in claim 30, wherein $R^1$ and $R^6$ are H and $R^2$, $R^3$, $R^4$, $R^5$ are H, F, Cl, Br or I.

36. A compound, as claimed in claim 30, wherein at least one of $R^{12}$, $R^{13}$, $R^{14}$, $R^{15}$ or $R^{16}$ is F.

37. A compound, as claimed in claim 36, wherein L incorporates a thioether bond.

38. A compound, as claimed in claim 30, wherein L is a single covalent bond and $R_x$ is a carboxylic acid, an activated ester of a carboxylic acid, an amine, an azide, a haloacetamide, an alkyl halide, a sulfonyl halide, an isothiocyanate, or a maleimide group.

39. A compound, as claimed in claim 31, wherein A is $OR^7$.

40. A compound, as claimed in claim 31, wherein A is $NR^8R^9$.

41. A compound, as claimed in claim 23, wherein one or both of $R^7$ and $R^8$ are independently $C_1$–$C_{18}$ acyl, the alkyl portions of which are optionally substituted one or more times by amino, hydroxy, carboxylic acid, a salt of carboxylic acid, a carboxylic acid ester of a $C_1$–$C_6$ alkyl, or a carboxylic acid ester of —$CH_2$—O—(C═O)—$R^{18}$, where $R^{18}$ is a $C_1$–$C_4$ alkyl.

42. A compound, as claimed in claim 30, wherein each of $R^1$, $R^3$, $R^4$, $R^6$ and $R^7$ are H; $R^2$ and $R^5$ are F; $R^{12}$ is selected from the group consisting of carboxylic acid, a salt of carboxylic acid, a carboxylic acid ester of a $C_1$–$C_6$ alkyl, a carboxylic acid ester of —$CH_2$—O—(C═O)—$R^{18}$, sulfonic acid, and salt of sulfonic acid; and exactly one of $R^{13}$, $R^{14}$, $R^{15}$ or $R^{16}$ is —L—$R_x$, where L is a single covalent bond, and the remaining of $R^{13}$, $R^{14}$, $R^{15}$ or $R^{16}$ are H.

43. A compound, as claimed in claim 30, wherein each of $R^1$, $R^2$, $R^3$, $R^4$, $R^5$, $R^6$ and $R^7$ are H; $R^{12}$ is carboxylic acid, a salt of carboxylic acid, a carboxylic acid ester of a $C_1$–$C_6$ alkyl, a carboxylic acid ester of —$CH_2$—O—(C═O)—$R^{18}$, sulfonic acid, salt of sulfonic acid; one of $R^{13}$, $R^{14}$, $R^{15}$ or $R^{16}$ is —L—$R_x$, and the remaining of $R^{13}$, $R^{14}$, $R^{15}$ and $R^{16}$ are F.

44. A compound, as claimed in claim 30, wherein each of $R^1$, $R^3$, $R^4$, $R^6$ and $R^7$ are H; $R^2$ and $R^5$ are F; $R^{12}$ is carboxylic acid, a salt of carboxylic acid, a carboxylic acid ester of a $C_1$–$C_6$ alkyl, a carboxylic acid ester of —$CH_2$—

O—(C=O)—$R^{18}$, sulfonic acid, or salt of sulfonic acid; exactly one of $R^{13}$, $R^{14}$, $R^{15}$ or $R^{16}$ is —L—$R_x$ and the remaining of $R^{13}$, $R^{14}$, $R^{15}$ or $R^{16}$ are all F.

45. A compound, as claimed in claim 23, that is
5-(acryloylamino)fluorescein,
4'-(((acryloyl)amino)methyl)fluorescein,
6-amino-9-(2,4-dicarboxyphenyl)-3H-xanthene-3-one, succinimidyl ester,
5-amino-2',7'-difluorofluorescein,
6-amino-2',7'-difluorofluorescein,
5-amino-2',4',5',7'-tetrafluorofluorescein,
5-azido-2',7'-difluorofluorescein,
4'-aminomethyl-2',7'-difluorofluorescein,
5-aminomethyl-2',7'-difluorofluorescein,
4',5'-bis(aminomethyl)-2',7'-difluorofluorescein,
5-bromomethyl-2',7'-difluorofluorescein,
9-(4-carboxy-2-sulfophenyl)-2',7'-difluorofluorescein,
9-(4-carboxy-2-sulfophenyl)2',7'-difluorofluorescein, succinimidyl ester,
6-(carboxymethyl)thio-2',4,5,7,7'-pentafluorofluorescein, succinimidyl ester,
6-(carboxymethyl)thio-2',4,5,7,7'-pentafluorofluorescein diacetate, succinimidyl ester,
6-carboxymethyl)thio-4,5,7-trifluorofluorescein diacetate, succinimidyl ester,
4-(carboxymethyl)thio-5,6,7-trifluorofluorescein diacetate, succinimidyl ester,
6-(carboxymethyl)thio-4,5,7-trifluorofluorescein, succinimidyl ester,
4-(carboxymethyl)thio-5,6,7-trifluorofluorescein, succinimidyl ester,
6-(carboxymethyl)thio-4,5,6,7-tetrafluoro-2',4',5',7'-tribromo-fluorescein, succinimidyl ester,
9-(2-carboxyphenyl)-2',7'-difluorodihydrofluorescein, succinimidyl ester,
9-(2-carboxyphenyl)-2',7'-difluorodihydrofluorescein diacetate, succinimidyl ester,
5-((4-(chloromethyl)benzoyl)amino)-2',7'-difluorofluorescein,
5-((4-(chloromethyl)benzoyl)amino)-2',7'-difluorofluorescein diacetate,
5-chloromethyl-2',7'-difluorofluorescein,
5-chloromethyl-2',7'-difluorofluorescein diacetate,
5-(4,6-dichlorotriazinyl)amino-2',7'-difluorofluorescein,
2-((((2',7'-difluorofluorescein-5-amino)carbonyl)methyi) thio)acetic acid, succinimidyl ester,
6-(2',7'-difluorofluorescein-5-carbonyl)aminohexanoic acid, succinimidyl ester,
2',7'-difluorofluorescein-5-carboxylic acid, succinimidyl ester,
2',7'-difluorofluorescein-5-carboxylic acid, sulfosuccinimidyl ester, sodium salt,
2',7'-difluorofluorescein-5-carboxylic acid, pentafluorophenyl ester,
2',7'-difluorofluorescein-5-carboxylic acid, p-nitrophenyl ester,
2',7'-difluorofluorescein-6-carboxylic acid, succinimidyl ester,
2',7'-difluorofluorescein-5-carboxylic acid diacetate, succinimidyl ester,
2',7'-difluorofluorescein-6-carboxylic acid diacetate, succinimidyl ester,
2',7'-difluorofluorescein-5-iodoacetamide,
2',7'-difluorofluorescein-6-iodoacetamide,
2',7'-difluorofluorescein-5-isothiocyanate,
2',7'-difluorofluorescein-6-isothiocyanate,
2',7'-difluorofluorescein-5-maleimide,
2',7'-difluorofluorescein-5-thiosemicarbazide,
2',7'-difluoro-5-((pentafluorobenzoyl)amino)fluorescein,
2',7'-difluoro-5-((pentafluorobenzoyl)amino)fluorescein diacetate,
6-(((hydrazino)carbonyl)methyl)thio-4,5,7-trifluorofluorescein,
4'-((iodoacetyl)arnino)methyl-2',7'-difluorofluorescein or
2',4',5',7'-tetrafluorofluorescein-5-carboxylic acid, succinimidyl ester.

46. A compound having the formula

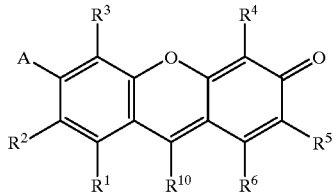

or the formula

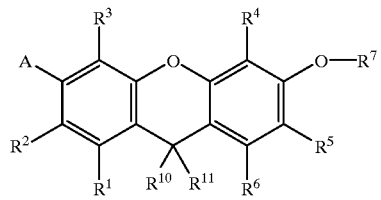

wherein
$R^1$ and $R^6$ are independently H, F, Cl, Br, I, $C_1$–$C_{18}$ alkyl or $C_1$–$C_{18}$ alkoxy;
$R^2$, $R^3$, $R^4$ and $R^5$ are independently H, F, Cl, Br, I, CN; or $C_1$–$C_{18}$ alkyl, $C_1$–$C_{18}$ alkoxy or $C_1$–$C_{18}$ alkylthio, where each alkyl, alkoxy or alkylthio is optionally further substituted by F, Cl, Br, I, sulfonic acid, salt of sulfonic acid, carboxylic acid, a salt of carboxylic acid, a carboxylic acid ester of a $C_1$–$C_6$ alkyl, a carboxylic acid ester of —$CH_2$—O—(C=O)—$R^{18}$ where $R^{18}$ is a $C_1$–$C_4$ alkyl; or amino, alkylamino, dialkylamino, or alkoxy, the alkyl portions of which independently have 1–6 carbons; or one or more of $R^2$, $R^3$, $R^4$, and $R^5$ is —L—$S_c$;
A is $OR^7$ or $NR^8R^9$,
where each $R^7$ is independently H, $C_1$–$C_{18}$ alkyl, a $C_1$–$C_{18}$ acyl wherein each alkyl group independently has 1–6 carbons and is optionally substituted by amino, hydroxy, carboxylic acid, a salt of carboxylic acid, a carboxylic acid ester of a $C_1$–$C_6$ alkyl, a carboxylic acid ester of —$CH_2$—O—(C=O)—$R^{18}$; or $R^7$ is —L—$S_c$;
$R^8$ and $R^9$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, a salt of $C_1$–$C_6$ sulfoalkyl, or $C_1$–$C_{18}$ acyl wherein the alkyl portions are optionally substituted by amino, hydroxy, carboxylic acid, a salt of carboxylic acid, a carboxylic acid ester of a $C_1$–$C_6$ alkyl, a carboxylic acid ester of —$CH_2$—O—(C=O)—$R^{18}$; or $R^8$ in combination with $R^2$, or $R^9$ in combination with $R^3$, or both, form a saturated 5- or 6-membered ring that is optionally substituted by one or more methyls; or $R^8$ in combination with $R^9$ forms a saturated 5- or 6-membered heterocycle that is a piperidine, a morpholine, a pyrrolidine or a piperazine, each of which is optionally substituted by methyl, carboxylic acid, a salt of carboxylic acid, a carboxylic acid ester of a $C_1$–$C_6$ alkyl, or a carboxylic acid ester of —$CH_2$—O—(C=O)—$R^{18}$; or one of $R^8$ and $R^9$ is —L—$S_c$; and $R^{10}$ is F, carboxylic acid, a salt of carboxylic acid, a carboxylic acid ester of a $C_1$–$C_6$ alkyl, or a carboxylic acid ester of —$CH_2$—O—(C=O)—$R^{18}$; or $R^{10}$ is $C_1$–$C_{18}$ alkyl, alkenyl or alkynyl that is optionally substituted one or more times by F, Cl, Br, carboxylic acid, a salt of carboxylic acid, a carboxylic acid ester of a $C_1$–$C_6$ alkyl, a carboxylic acid ester of —$CH_2$—O—(C=O)—$R^{18}$, sulfonic acid, salt of sulfonic acid, amino, alkylamino, or dialkylamino, the alkyl groups of which have 1–6 carbons; or $R^{10}$ is —L—$S_c$; or $R^{10}$ has the formula

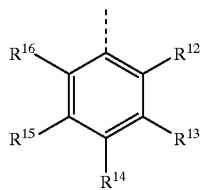

where $R^{12}$, $R^{13}$, $R^{14}$, $R^{15}$ and $R^{16}$ are independently H, F, Cl, Br, I; or sulfonic acid, salt of sulfonic acid, carboxylic acid, a salt of carboxylic acid, a carboxylic acid ester of a $C_1$–$C_6$ alkyl, a carboxylic acid ester of —$CH_2$—O—(C=O)—$R^{18}$, CN, nitro, hydroxy, azido, amino, hydrazino; or $C_1$–$C_{18}$ alkyl, $C_1$–$C_{18}$ alkoxy, $C_1$–$C_{18}$ alkylthio, $C_1$–$C_{18}$ alkylamino, $C_1$–$C_{18}$ alkylester, $C_1$–$C_{18}$ alkylamido or $C_1$–$C_{18}$ arylamido, the alkyl or aryl portions of which are optionally substituted one or more times by F, Cl, Br, I, hydroxy, carboxylic acid, a salt of carboxylic acid, a carboxylic acid ester of a $C_1$–$C_6$ alkyl, a carboxylic acid ester of —$CH_2$—O—(C=O)—$R^{18}$, sulfonic acid, salt of sulfonic acid, amino, alkylamino, dialkylamino or alkoxy, the alkyl portions of each having 1–6 carbons; or one pair of adjacent substituents $R^{13}$ and $R^{14}$, $R^{14}$ and $R^{15}$ or $R^{15}$ and $R^{16}$, when taken in combination, form a fused 6-membered aromatic ring that is optionally further substituted by carboxylic acid, a salt of carboxylic acid, a carboxylic acid ester of a $C_1$–$C_6$ alkyl, a carboxylic acid ester of —$CH_2$—O—(C=O)—$R^{18}$; or one or more of $R^{12}$, $R^{13}$, $R^{14}$, $R^{15}$ and $R^{16}$ is —L—$S_c$;

$R^{11}$ is H, hydroxy, CN or a $C_1$–$C_6$ alkoxy; or $R^{10}$ in combination with $R^{11}$ forms a 5-membered spirolactone ring or a 5-membered spirosultone ring; or $R^{11}$ in combination with $R^{12}$ forms a 5- or 6-membered spirolactone ring or a 5- or 6-membered spirosultone ring that is optionally and independently substituted by H, F or $CH_3$; or $R^{10}$ in combination with $R^{11}$ is a carbonyl oxygen;

provided that at least one of $R^1$, $R^2$, $R^3$, $R^4$, $R^5$, $R^6$ and $R^{10}$ is F, or at least three of $R^{12}$, $R^{13}$, $R^{14}$, $R^{15}$ and $R^{16}$ are F; and further provided that at least one of $R^2$, $R^3$, $R^4$, $R^5$, $R^7$, $R^8$, $R^9$, $R^{10}$, $R^{12}$, $R^{13}$, $R^{14}$, $R^{15}$ and $R^{16}$ is an —L—$S_c$;

L is a single covalent bond, or L is a covalent linkage having 1–24 nonhydrogen atoms selected from the group consisting of C, N, O and S and is composed of any combination of single, double, triple or aromatic carbon-carbon bonds, carbon-nitrogen bonds, nitrogen-nitrogen bonds, carbon-oxygen bonds and carbon-sulfur bonds; and $S_c$ is a conjugated substance.

47. A compound, as claimed in claim 46, wherein exactly one of $R^2$, $R^3$, $R^4$, $R^5$, $R^7$, $R^8$, $R^9$, $R^{10}$, $R^{11}$, $R^{12}$ $R^{13}$, $R^{14}$, $R^{15}$ and $R^{16}$ is —L—$S_c$.

48. A compound, as claimed in claim 47, wherein one of $R^{13}$, $R^{14}$, $R^{15}$ or $R^{16}$ is an L—$S_c$.

49. A compound, as claimed in claim 48, wherein $R^7$ is H; $R^{12}$ is H, F, carboxylic acid, a salt of carboxylic acid, a carboxylic acid ester of a $C_1$–$C_6$ alkyl, a carboxylic acid ester of —$CH_2$—O—(C=O)—$R^{18}$, sulfonic acid or a salt of sulfonic acid.

50. A compound, as claimed in claim 49, wherein $R^{13}$, $R^{14}$, $R^{15}$ and $R^{16}$ are all F.

51. A compound, as claimed in claim 49, wherein $R^{13}$, $R^{14}$, $R^{15}$ and $R^{16}$ are all H.

52. A compound, as claimed in claim 49, wherein A is $NR^8R^9$.

53. A compound, as claimed in claim 47, wherein one of $R^2$, $R^3$, $R^4$, $R^5$, $R^7$, $R^8$, $R^9$ or $R^{10}$ is an L—$S_c$.

54. A compound, as claimed in claim 49, wherein $S_c$ is an amino acid, peptide, protein, polysaccharide, ion-complexing moiety, nucleotide, oligonucleotide, nucleic acid, hapten, drug, lipid, phospholipid, lipoprotein, lipopolysaccharide, liposome, lipophilic polymer, non-biological organic polymer, polymeric microparticle, animal cell, plant cell, bacterium, yeast, or virus.

55. A compound, as claimed in claim 54, wherein one of $R^{12}$, $R^{13}$, $R^{14}$, $R^{15}$ or $R^{16}$ is an L—$S_c$.

56. A compound, as claimed in claim 55, wherein $S_c$ is an amino acid, peptide or protein.

57. A compound, as claimed in claim 56, wherein $S_c$ is an antibody, antibody fragment, avidin, streptavidin, lectin, protein A or protein G.

58. A compound, as claimed in claim 55, wherein $S_c$ is a polysaccharide.

59. A compound, as claimed in claim 55, wherein $S_c$ is an ion-complexing moiety.

60. A compound, as claimed in claim 59, wherein the ion-complexing moiety is a BAPTA or APTRA or a phenanthroline.

61. A compound, as claimed in claim 55, wherein $S_c$ is a crown ether.

62. A compound, as claimed in claim 55, wherein $S_c$ is a nucleotide, an oligonucleotide or a nucleic acid.

63. A compound, as claimed in claim 55, wherein $S_c$ is a hapten or drug.

64. A compound, as claimed in claim 55, wherein $S_c$ is a lipid, phospholipid, lipoprotein, lipopolysaccharide, liposome or lipophilic polymer.

65. A compound, as claimed in claim 55, wherein $S_c$ is a non-biological organic polymer or polymeric microparticle.

66. A compound, as claimed in claim 55, wherein $S_c$ is a animal cell, plant cell, bacterium, yeast or virus.

67. A compound having the formula

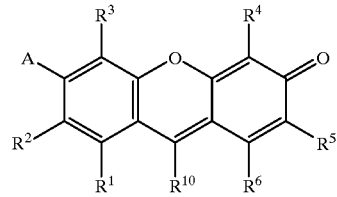

or the formula

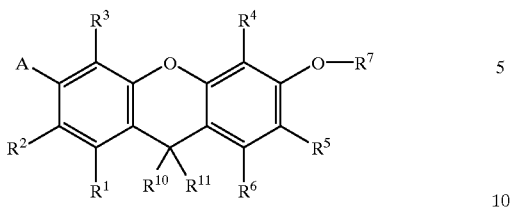

wherein $R^1$ and $R^6$ are independently H, F, Cl, Br, I, $C_1$–$C_{18}$ alkyl or $C_1$–$C_{18}$ alkoxy;

$R^2$, $R^3$, $R^4$ and $R^5$ are independently H, F, Cl, Br, I, CN; or $C_1$–$C_{18}$ alkyl, $C_1$–$C_{18}$ alkoxy or $C_1$–$C_{18}$ alkylthio, where each alkyl, alkoxy or alkylthio is optionally further substituted by F, Cl, Br, I, sulfonic acid, salt of sulfonic acid, carboxylic acid, a salt of carboxylic acid, a carboxylic acid ester of a $C_1$–$C_6$ alkyl, a carboxylic acid ester of —$CH_2$—O—(C=O)—$R^{18}$ where $R^{18}$ is a $C_1$–$C_4$ alkyl; or amino, alkylamino, dialkylamino, or alkoxy, the alkyl portions of which independently have 1–6 carbons; or one or both of $R^3$ and $R^4$ are —$CH_2$N($CH_2COOR^{17}$)$_2$, where $R^{17}$ is H, a biologically compatible counterion, a linear or branched alkyl having 1–6 carbons, or —$CH_2$—O—(C=O)—$R^{18}$; or one or more of $R^2$, $R^3$, $R^4$, and $R^5$ is —L—$R_x$; or one or more of $R^2$, $R^3$, $R^4$, and $R^5$ is —L—$S_c$;

A is $OR^7$ or $NR^8R^9$, where each $R^7$ is independently a BLOCK, or $R^7$ is —L—$R_x$, or $R^7$ is —L—$S_c$;

$R^8$ and $R^9$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, a salt of $C_1$–$C_6$ sulfoalkyl, or $C_1$–$C_{18}$ acyl wherein the alkyl portions are optionally substituted by amino, hydroxy, carboxylic acid, a salt of carboxylic acid, a carboxylic acid ester of a $C_1$–$C_6$ alkyl, a carboxylic acid ester of —$CH_2$—O—(C=O)—$R^{18}$; or $R^8$ in combination with $R^2$, or $R^9$ in combination with $R^3$, or both, form a saturated 5- or 6-membered ring that is optionally substituted by one or more methyls; or $R^8$ in combination with $R^9$ forms a saturated 5- or 6-membered heterocycle that is a piperidine, a morpholine, a pyrrolidine or a piperazine, each of which is optionally substituted by methyl, carboxylic acid, a salt of carboxylic acid, a carboxylic acid ester of a $C_1$–$C_6$ alkyl, or a carboxylic acid ester of —$CH_2$—O—(C=O)—$R^{18}$; or one of $R^8$ and $R^9$ is a BLOCK; or one of $R^8$ and $R^9$ is —L—$R_x$; or one of $R^8$ and $R^9$ is —L—$S_c$; and $R^{10}$ is F, carboxylic acid, a salt of carboxylic acid, a carboxylic acid ester of a $C_1$–$C_6$ alkyl, or a carboxylic acid ester of —$CH_2$—O—(C=O)—$R^{18}$; or $R^{10}$ is $C_1$–$C_{18}$ alkyl, alkenyl or alkynyl that is optionally substituted one or more times by F, Cl, Br, carboxylic acid, a salt of carboxylic acid, a carboxylic acid ester of a $C_1$–$C_6$ alkyl, a carboxylic acid ester of —$CH_2$—O—(C=O)—$R^{18}$, sulfonic acid, salt of sulfonic acid, amino, alkylamino, or dialkylamino, the alkyl groups of which have 1–6 carbons; or $R^{10}$ is —L—$R_x$; or $R^{10}$ is —L—$S_c$; or $R^{10}$ has the formula

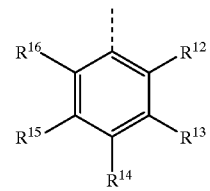

where $R^{12}$, $R^{13}$, $R^{14}$, $R^{15}$ and $R^{16}$ are independently H, F, Cl, Br, I; or sulfonic acid, salt of sulfonic acid, carboxylic acid, a salt of carboxylic acid, a carboxylic acid ester of a $C_1$–$C_6$ alkyl, a carboxylic acid ester of —$CH_2$—O—(C=O)—$R^{18}$, CN, nitro, hydroxy, azido, amino, hydrazino; or $C_1$–$C_{18}$ alkyl, $C_1$–$C_{18}$ alkoxy, $C_1$–$C_{18}$ alkylthio, $C_1$–$C_{18}$ alkylamino, $C_1$–$C_{18}$ alkylester, $C_1$–$C_{18}$ alkylamido or $C_1$–$C_{18}$ arylamido, the alkyl or aryl portions of which are optionally substituted one or more times by F, Cl, Br, I, hydroxy, carboxylic acid, a salt of carboxylic acid, a carboxylic acid ester of a $C_1$–$C_6$ alkyl, a carboxylic acid ester of —$CH_2$—O—(C=O)—$R^{18}$, sulfonic acid, salt of sulfonic acid, amino, alkylamino, dialkylamino or alkoxy, the alkyl portions of each having 1–6 carbons; or one pair of adjacent substituents $R^{13}$ and $R^{14}$, $R^{14}$ and $R^{15}$ or $R^{15}$ and $R^{16}$, when taken in combination, form a fused 6-membered aromatic ring that is optionally further substituted by carboxylic acid, a salt of carboxylic acid, a carboxylic acid ester of a $C_1$–$C_6$ alkyl, a carboxylic acid ester of —$CH_2$—O—(C=O)—$R^{18}$; or one or more of $R^{12}$, $R^{13}$, $R^{14}$, $R^{15}$ and $R^{16}$ is —L—$R_x$; or one or more of $R^{12}$, $R^{13}$, $R^{14}$, $R^{15}$ and $R^{16}$ is —L—$S_c$;

$R^{11}$ is H, hydroxy, CN or a $C_1$–$C_6$ alkoxy; or $R^{10}$ in combination with $R^{11}$ forms a 5-membered spirolactone ring or a 5-membered spirosultone ring; or $R^{11}$ in combination with $R^{12}$ forms a 5- or 6-membered spirolactone ring or a 5- or 6-membered spirosultone ring that is optionally and independently substituted by H, F or $CH_3$; or $R^{10}$ in combination with $R^{11}$ is a carbonyl oxygen;

provided that at least one of $R^1$, $R^2$, $R^3$, $R^4$, $R^5$, $R^6$, and $R^{10}$ is F, or at least three of $R^{12}$, $R^{13}$, $R^{14}$, $R^{15}$ and $R^{16}$ are F; and further provided at least one of $R^7$, $R^8$ or $R^9$ is a BLOCK;

each L is a single covalent bond, or L is a covalent linkage having 1–24 nonhydrogen atoms selected from the group consisting of C, N, O and S and is composed of any combination of single, double, triple or aromatic carbon-carbon bonds, carbon-nitrogen bonds, nitrogen-nitrogen bonds, carbon-oxygen bonds and carbon-sulfur bonds; and $R_x$ is a reactive site;

$S_c$ is a conjugated substance; and each BLOCK moiety is independently a monovalent moiety derived by removal of a hydroxy group from phosphate or from sulfate, or a biologically compatible salt thereof; or a monovalent moiety derived by removal of a hydroxy group from a carboxy group of an aliphatic or aromatic carboxylic acid or of an amino acid, protected amino acid, peptide, or protected peptide; or a monovalent moiety derived by removal of a hydroxy group from an alcohol or from a mono- or polysaccharide, where said BLOCK is selected to be removable from said compound by action of an enzyme;

or

BLOCK is a photolabile caging group.

68. A compound, as claimed in claim 67, wherein none of $R^2$, $R^3$, $R^4$, $R^5$, $R^7$, $R^8$, $R^9$, $R^{10}$, $R^{13}$, $R^{14}$, $R^{15}$ or $R^6$ is an —L—$R_x$ or —L—$S_c$.

69. A compound, as claimed in claim 68, wherein at least one of $R^1$, $R^2$, $R^3$, $R^4$, $R^5$ or $R^6$ is F.

70. A compound, as claimed in claim 68, wherein at least one of $R^{13}$, $R^{14}$, $R^{15}$ or $R^{16}$ is F.

71. A compound, as claimed in claim 68, wherein each of $R^{13}$, $R^{14}$, $R^{15}$ and $R^{16}$ is F.

72. A compound, as claimed in claim 68, wherein A is $OR^7$ and $R^7$ is BLOCK.

73. A compound, as claimed in claim 72, wherein $R^2$ and $R^5$ are each F.

74. A compound, as claimed in claim 68, wherein BLOCK is an ester of phosphate, sulfate or an aliphatic or aromatic carboxylic acid.

75. A compound, as claimed in claim 72, wherein BLOCK is an ester of phosphate, sulfate or an aliphatic or aromatic carboxylic acid.

76. A compound, as claimed in claim 68, wherein BLOCK is an ether of an alcohol or a mono- or polysaccharide.

77. A compound, as claimed in claim 67, wherein $R^7$ and $R^8$ are BLOCK and BLOCK is a photolabile caging group.

78. A compound, as claimed in claim 77, wherein said photolabile caging group is an o-nitroarylmethine, a 2-methoxy-5-nitrophenyl or a desyl moiety.

79. A compound, as claimed in claim 67, wherein one of $R^2$, $R^3$, $R^4$, $R^5$, $R^{13}$, $R^{14}$, $R^{15}$ or $R^{16}$ is an —L—$R_x$.

80. A compound, as claimed in claim 79, wherein $R_x$ is a carboxylic acid, an activated ester of a carboxylic acid, a succinimidyl ester, an amine, an azide, a haloacetamide, an alkyl halide, a sulfonyl halide, an isothiocyanate, or a maleimide group.

81. A compound, as claimed in claim 67, wherein one of $R^2$, $R^3$, $R^4$, $R^5$, $R^{13}$, $R^{14}$, $R^{15}$ or $R^{16}$ is an —L—$S_c$.

82. A compound, as claimed in claim 81, wherein $S_c$ is an amino acid, peptide, protein, polysaccharide, ion-complexing moiety, nucleotide, oligonucleotide, nucleic acid, hapten, drug, lipid, phospholipid, lipoprotein, lipopolysaccharide, liposome, lipophilic polymer, non-biological organic polymer, polymeric microparticle, animal cell, plant cell, bacterium, yeast, or virus.

83. A compound, as claimed in claim 67, wherein A is $NR^8R^9$.

84. A compound, as claimed in claim 67, wherein $R^9$ is H; $R^8$ is BLOCK where BLOCK is an amino acid, a peptide or a protected peptide; or $R^8$ is a $C_1$–$C_{18}$ aliphatic carboxylic acid, arylalkanoic carboxylic acid or alkylaromatic carboxylic acid, the alkyl and aryl portion of which are optionally substituted one or more times by F, Cl, Br, I, hydroxy, carboxylic acid, a salt of carboxylic acid, a carboxylic acid ester of a $C_1$–$C_6$ alkyl, or a carboxylic acid ester of —$CH_2$—O—(C=O)$R^{18}$.

85. A compound, as claimed in claim 67 wherein $R^{11}$ is H.

86. A compound, as claimed in claim 67, that is
3'-acetoxy-6'-acetylamino-4,5,6,7-tetrafluorospiro (isobenzofuran)-1(3H),9'-(9H)xanthen-3-one,
6'-acetylamino-3'-phosphoryloxy-4,5,6,7-tetrafluorospiro (isobenzofuran)-1(3H),9'-(9H)xanthen-3-one, tetrasodium salt,
6'-amino-3'-methoxy-4,5,6,7-tetrafluorospiro (isobenzofuran)-1(3H),9'-(9H)xanthen-3-one,
5-chloromethyl-2',7'-difluorofluorescein diacetate,
5-chloromethyl-2',7'-difluorofluorescein di-β-D-galactopyranoside,
2',7'-difluoro-5-dodecanoylaminofluorescein di-β-D-galactopyranoside,
2',7'-difluorofluorescein diacetate,
2',7'-difluorofluorescein-5-carboxylic acid diacetate,
2',7'-difluorofluoreseein-5-carboxylic acid diacetate, succinimidyl ester,
2',7'-difluorofluorescein-5-carboxylic acid di(2-nitrobenzyl ether),
2',7'-difluorofluorescein dibutyrate,
2',7'-difluorofluorescein di(4,5-dimethoxy-2-nitrobenzyl ether),
2',7'-difluorofluorescein diethyl ether,
2',7'-difluorofluorescein dioctadecanoate,
2',7'-difluorofluorescein di-β-D-galactopyranoside,
2',7'-difluorofluorescein di-β-D-glucuronide,
2',7'-difluorofluorescein di(4-guanidinobenzoate),
2',7'-difluorofluorescein diphosphate, tetrasodium salt,
2',7'-difluorofluorescein mono(4-guanidinobenzoate),
2',7'-difluoro-3-O-methylfluorescein phosphate,
2',7'-difluoro-5-((pentafluorobenzoyl)amino)fluorescein diacetate,
2',4,5,6,7,7'-hexafluorofluorescein diacetate,
6'-L-leucylamino-3'-methoxy-4,5,6,7-tetrafluorospiro (isobenzofuran)-1(3H),9'-(9H)xanthen-3-one,
2',4',5',7'-tetrafluorofluorescein diacetate,
4,5,6,7-tetrafluorofluorescein diacetate,
4,5,6,7-tetrafluorofluorescein di-β-D-galactopyranoside or
4,5,6,7-tetrafluorofluorescein diphosphate, tetraammonium salt.

87. A method of staining a biological sample, comprising the steps of:

a) preparing a dye solution comprising a dye compound of the formula:

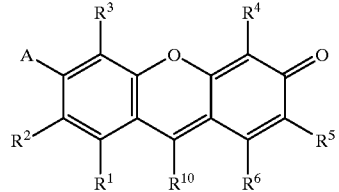

or the formula

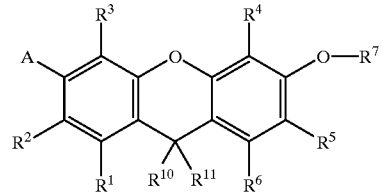

wherein
$R^1$ and $R^6$ are independently H, F, Cl, Br, I, $C_1$–$C_{18}$ alkyl or $C_1$–$C_{18}$ alkoxy;
$R^2$, $R^3$, $R^4$ and $R^5$ are independently H, F, Cl, Br, I, CN; or $C_1$–$C_{18}$ alkyl, $C_1$–$C_{18}$ alkoxy or $C_1$–$C_{18}$ alkylthio, where each alkyl, alkoxy or alkylthio is optionally further substituted by F, Cl, Br, I, sulfonic acid, salt of sulfonic acid, carboxylic acid, a salt of carboxylic acid, a carboxylic acid ester of a $C_1$–$C_6$ alkyl, a carboxylic acid ester of —$CH_2$—O—(C=O)—$R^{18}$ where $R^{18}$ is a $C_1$–$C_4$ alkyl; or amino, alkylamino, dialkylamino, or alkoxy, the alkyl portions of which independently have 1–6 carbons; or one or both of $R^3$ and $R^4$ are —$CH_2$N ($CH_2COOR^{17}$)$_2$, where $R^{17}$ is H, a biologically compatible counterion, a linear or branched alkyl having 1–6 carbons, or —$CH_2$—O—(C=O)—$R^{18}$; or one or more of $R^2$, $R^3$, $R^4$, and $R^5$ is —L—$R_x$; or one or more of $R^2$, $R^3$, $R^4$, and $R^5$ is —L—$S_c$;

A is $OR^7$ or $NR^8R^9$, where each $R^7$ is independently a BLOCK, or $R^7$ is —L—$R_x$, or $R^7$ is —L—$S_c$;

$R^8$ and $R^9$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, a salt of $C_1$–$C_6$ sulfoalkyl, or $C_1$–$C_{18}$ acyl wherein the alkyl portions are optionally substituted by amino, hydroxy, carboxylic acid, a salt of carboxylic acid, a carboxylic acid ester of a $C_1$–$C_6$ alkyl, a carboxylic acid ester of —$CH_2$—O—(C=O)—$R^{18}$; or $R^8$ in combination with $R^2$, or $R^9$ in combination with $R^3$, or both, form a saturated 5- or 6-membered ring that is optionally substituted by one or more methyls; or $R^8$ in combination with $R^9$ forms a saturated 5- or 6-membered heterocycle that is a piperidine, a morpholine, a pyrrolidine or a piperazine, each of which is optionally substituted by methyl, carboxylic acid, a salt of carboxylic acid, a carboxylic acid ester of a $C_1$–$C_6$ alkyl, or a carboxylic acid ester of —$CH_2$—O—(C=O)—$R^{18}$; or one of $R^8$ and $R^9$ is a BLOCK; or one of $R^8$ and $R^9$ is —L—$R_x$; or one of $R^8$ and $R^9$ is —L—$S_c$; and $R^{10}$ is F, carboxylic acid, a salt of carboxylic acid, a carboxylic acid ester of a $C_1$–$C_6$ alkyl, or a carboxylic acid ester of —$CH_2$—O—(C=O)—$R^{18}$; or $R^{10}$ is $C_1$–$C_{18}$ alkyl, alkenyl or alkynyl that is optionally substituted one or more times by F, Cl, Br, carboxylic acid, a salt of carboxylic acid, a carboxylic acid ester of a $C_1$–$C_6$ alkyl, a carboxylic acid ester of —$CH_2$—O—(C=O)—$R^{18}$, sulfonic acid, salt of sulfonic acid, amino, alkylamino, or dialkylamino, the alkyl groups of which have 1–6 carbons; or $R^{10}$ is —L—$R_x$; or $R^{10}$ is —L—$S_c$; or $R^{10}$ has the formula

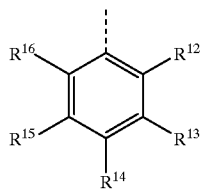

where $R^{12}$, $R^{13}$, $R^{14}$, $R^{15}$ and $R^{16}$ are independently H, F, Cl, Br, I; or sulfonic acid, salt of sulfonic acid, carboxylic acid, a salt of carboxylic acid, a carboxylic acid ester of a $C_1$–$C_6$ alkyl, a carboxylic acid ester of —$CH_2$—O—(C=O)—$R^{18}$, CN, nitro, hydroxy, azido, amino, hydrazino; or $C_1$–$C_{18}$ alkyl, $C_1$–$C_{18}$ alkoxy, $C_1$–$C_{18}$ alkylthio, $C_1$–$C_{18}$ alkylamino, $C_1$–$C_{18}$ alkylester, $C_1$–$C_{18}$ alkylamido or $C_1$–$C_{18}$ arylamido, the alkyl or aryl portions of which are optionally substituted one or more times by F, Cl, Br, I, hydroxy, carboxylic acid, a salt of carboxylic acid, a carboxylic acid ester of a $C_1$–$C_6$ alkyl, a carboxylic acid ester of —$CH_2$—O—(C=O)—$R^{18}$, sulfonic acid, salt of sulfonic acid, amino, alkylamino, dialkylamino or alkoxy, the alkyl portions of each having 1–6 carbons; or one pair of adjacent substituents $R^{13}$ and $R^{14}$, $R^{14}$ and $R^{15}$ or $R^{15}$ and $R^{16}$, when taken in combination, form a fused 6-membered aromatic ring that is optionally further substituted by carboxylic acid, a salt of carboxylic acid, a carboxylic acid ester of a $C_1$–$C_6$ alkyl, a carboxylic acid ester of —$CH_2$—O—(C=O)—$R^{18}$; or one or more of $R^{12}$, $R^{13}$, $R^{14}$, $R^{15}$ and $R^{16}$ is —L—$R_x$; or one or more of $R^{12}$, $R^{13}$, $R^{14}$, $R^{15}$ and $R^{16}$ is —L—$S_c$;

$R^{11}$ is H, hydroxy, CN or a $C_1$–$C_6$ alkoxy; or $R^{10}$ in combination with $R^{11}$ forms a 5-membered spirolactone ring or a 5-membered spirosultone ring; or $R^{11}$ in combination with $R^{12}$ forms a 5- or 6-membered spirolactone ring or a 5- or 6-membered spirosultone ring that is optionally and independently substituted by H, F or $CH_3$; or $R^{10}$ in combination with $R^{11}$ is a carbonyl oxygen;

provided that at least one of $R^1$, $R^2$, $R^3$, $R^4$, $R^5$, $R^6$, and $R^{10}$ is F, or at least three of $R^{12}$, $R^{13}$, $R^4$, $R^{15}$ and $R^{16}$ are F;

each L is a single covalent bond, or L is a covalent linkage having 1–24 nonhydrogen atoms selected from the group consisting of C, N, O and S and is composed of any combination of single, double, triple or aromatic carbon-carbon bonds, carbon-nitrogen bonds, nitrogen-nitrogen bonds, carbon-oxygen bonds and carbon-sulfur bonds; and $R_x$ is a reactive site;

$S_c$ is a conjugated substance; and each BLOCK moiety is independently a monovalent moiety derived by removal of a hydroxy group from phosphate or from sulfate, or a biologically compatible salt thereof; or a monovalent moiety derived by removal of a hydroxy group from a carboxy group of an aliphatic or aromatic carboxylic acid or of an amino acid, protected amino acid, peptide, or protected peptide; or a monovalent moiety derived by removal of a hydroxy group from an alcohol or from a mono- or polysaccharide, where said BLOCK is selected to be removable from said compound by action of an enzyme;

or

BLOCK is a photolabile caging group;

in a concentration sufficient to yield a detectable optical response under the desired conditions;

b) combining the sample of interest with the dye solution for a period of time sufficient for the dye compound to yield a detectable optical response upon illumination; and c) illuminating said sample at a wavelength selected to elicit said optical response.

88. A method of staining, as claimed in claim 87, further comprising washing the sample after combining the sample with the dye solution.

89. A method of staining, as claimed in claim 88, further comprising combining the sample with an additional detection reagent that has spectral properties that are detectably different from said optical response.

90. A method of staining, as claimed in claim 88, further comprising the step of determining a characteristic of the sample by comparing the optical response with a standard response parameter.

91. A method of staining, as claimed in claim 90, wherein the characteristic of the sample being determined is the activity of an oxidative enzyme in a sample, and where for said dye compound $R^{11}$ is H.

92. A method of staining, as claimed in claim 90, wherein said sample comprises cells, and the characteristic of the sample being determined is the retention efficiency of said cells, and wherein the dye solution comprises a dye of the formula

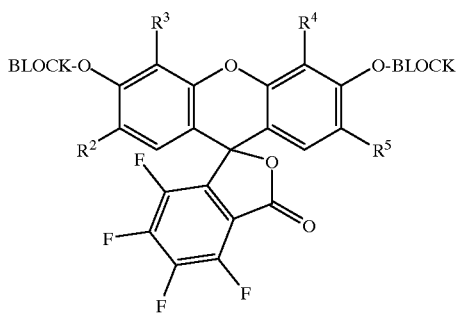

wherein $R^2$, $R^3$, $R^4$ and $R^5$ are independently H, F, Cl, Br, I, CN, $C_1$-$C_{18}$ alkyl, $C_1$-$C_{18}$ alkoxy or $C_1$-$C_{18}$ alkylthio, where each alkyl, alkoxy or alkylthio is optionally further substituted by F, Cl, Br, I, amino, alkylamino, dialkylamino, or alkoxy, the alkyl portions of which independently have 1–6 carbons; or one or both of $R^3$ and $R^4$ are —$CH_2N(CH_2COOR^{17})_2$, where $R^{17}$ is a linear or branched alkyl having 1–6 carbons, or —$CH_2$—O—(C=O)—$R^{18}$ where $R^{18}$ is a $C_1$-$C_4$ alkyl;

in the minimum concentration that gives a detectable optical response that is fluorescence emission.

93. A method of staining, as claimed in claim 92, wherein comparing comprises comparing the fluorescence emission within the cells in the sample with the fluorescence within in cells having a known cellular efflux pump efficiency, and where for said dye compound BLOCK is a monovalent moiety derived by removal of a hydroxy group from phosphate or from sulfate, or a biologically compatible salt thereof; or a monovalent moiety derived by removal of a hydroxy group from a carboxy group of an aliphatic or aromatic carboxylic acid; or a monovalent moiety derived by removal of a hydroxy group from an alcohol, where said BLOCK is selected to be removable from said compound by action of an enzyme.

94. A method of staining, as claimed in claim 92, wherein BLOCK is acetate.

95. A method of staining, as claimed in claim 90, wherein comparing comprises tracing the temporal or spatial location of the optical response within the biological sample.

96. A method of staining, as claimed in claim 95, wherein for said dye compound $R^2$, $R^3$, $R^4$ and $R^5$ are independently H or F;

$R^{12}$ is carboxylic acid, a salt of carboxylic acid, a carboxylic acid ester of a $C_1$-$C_6$ alkyl, a carboxylic acid ester of —$CH_2$—O—(C=O)—$R^{18}$, sulfonic acid or a salt of sulfonic acid,;

$R^{13}$, $R^{14}$, $R^{15}$ and $R^{16}$ are independently H, F, carboxylic acid, a salt of carboxylic acid, a carboxylic acid ester of a $C_1$-$C_6$ alkyl, a carboxylic acid ester of —$CH_2$—O—(C=O)—$R^{18}$, sulfonic acid, salt of sulfonic acid, or $C_1$-$C_6$ alkylthio that is optionally substituted by carboxylic acid, a salt of carboxylic acid, a carboxylic acid ester of a $C_1$-$C_6$ alkyl, or a carboxylic acid ester of —$CH_2$—O—(C=O)—$R^{18}$.

97. A method of staining, as claimed in claim 95, wherein for said dye compound one or both of $R^3$ and $R^4$ are —$CH_2N(CH_2COOR^{17})_2$, where $R^{17}$ is H, a biologically compatible counterion, a linear or branched alkyl having 1–carbons, or —$CH_2$—O—(C=O)—$R^{18}$ where $R^{18}$ is a $C_1$-$C_4$ alkyl;

or one or $R^{13}$, $R^{14}$, $R^{15}$ and $R^{16}$ is carboxylic acid, a salt of carboxylic acid, a carboxylic acid ester of a $C_1$-$C_6$ alkyl, a carboxylic acid ester of —$CH_2$—O—(C=O)—$R^{18}$ where $R^{18}$ is a $C_1$-$C_4$ alkyl, sulfonic acid, salt of sulfonic acid, $C_1$-$C_{18}$ alkyl, $C_1$-$C_{18}$ alkoxy, $C_1$-$C_{18}$ alkylthio, $C_1$-$C_{18}$ alkylamino, $C_1$-$C_{18}$ alkylamido or $C_1$-$C_{18}$ arylamido.

98. A method of staining, as claimed in claim 97, wherein one of $R^{13}$, $R^{14}$, $R^{15}$ and $R^{16}$ is $C_1$-$C_{18}$ alkyl, $C_1$-$C_{18}$ alkoxy, $C_1$-$C_{18}$ alkylthio, $C_1$-$C_{18}$ alkylamino, $C_1$-$C_{18}$ alkylamido or $C_1$-$C_{18}$ arylamido.

99. A method of staining, as claimed in claim 95, wherein for said dye compound at least one of $R^{13}$, $R^{14}$, $R^{15}$ and $R^{16}$ is —L—$R_x$;

where $R_x$ is a haloacetamide, an alkyl halide, halomethylbenzamido or perfluorobenzamido.

100. A method of staining, as claimed in claim 95, wherein for said dye compound at least one of $R^{13}$, $R^{14}$, $R^{15}$ and $R^{16}$ is —L—$S_c$;

where $S_c$ is a protein, a polysaccharide, an ion-complexing moiety, a lipid, or a non-biological organic polymer or polymeric microparticle, that is optionally bound to one or more additional fluorophores that are the same or different.

101. A method of staining, as claimed in claim 95, wherein for said dye compound at least one $R^7$ is a BLOCK that is a monovalent moiety derived by removal of a hydroxy group from a carboxy group of a carboxylic acid, or BLOCK is a photolabile caging group.

102. A method of staining, as claimed in claim 87, wherein said sample further comprises cells, and wherein for said dye compound at least one $R^7$ is a BLOCK or H;

$R^{11}$ in combination with $R^{12}$ forms a 5- or 6-membered spirolactone ring or a 5- or 6-membered spirosultone ring; and each of $R^{13}$-$R^{16}$ is F;

further comprising optionally washing the cells, after combining the sample with the dye compound, to remove residual dye compound that is outside said cells.

103. One or more dye compounds of the formula

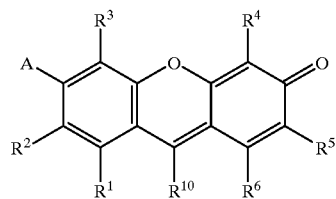

or the formula

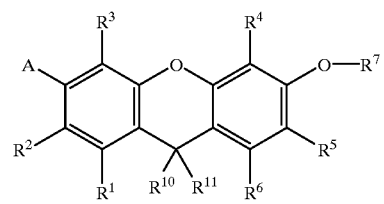

wherein $R^1$ and $R^6$ are independently H, F, Cl, Br, I, $C_1$–$C_{18}$ alkyl or $C_1$–$C_{18}$ alkoxy;

$R^2$, $R^3$, $R^4$ and $R^5$ are independently H, F, Cl, Br, I, CN; or $C_1$–$C_{18}$ alkyl, $C_1$–$C_{18}$ alkoxy or $C_1$–$C_{18}$ alkylthio, where each alkyl, alkoxy or alkylthio is optionally further substituted by F, Cl, Br, I, sulfonic acid, salt of sulfonic acid, carboxylic acid, a salt of carboxylic acid, a carboxylic acid ester of a $C_1$–$C_6$ alkyl, a carboxylic acid ester of —$CH_2$—O—(C=O)—$R^{18}$ where $R^{18}$ is a $C_1$–$C_4$ alkyl; or amino, alkylamino, dialkylamino, or alkoxy, the alkyl portions of which independently have 1–6 carbons;

A is $OR^7$ or $NR^8R^9$, where each $R^7$ is independently H, $C_1$–$C_{18}$ alkyl, a $C_1$–$C_{18}$ acyl wherein each alkyl group independently has 1–6 carbons and is optionally substituted by amino, hydroxy, carboxylic acid, a salt of carboxylic acid, a carboxylic acid ester of a $C_1$–$C_6$ alkyl, a carboxylic acid ester of —$CH_2$—O—(C=O)—$R^{18}$;

$R^8$ and $R^9$ are independently H, $C_1$–$C_6$ alkyl, $C_1$–$C_6$ carboxyalkyl, $C_1$–$C_6$ sulfoalkyl, a salt of $C_1$–$C_6$ carboxyalkyl, a salt of $C_1$–$C_6$ sulfoalkyl, or $C_1$–$C_{18}$ acyl wherein the alkyl portions are optionally substituted by amino, hydroxy, carboxylic acid, a salt of carboxylic acid, a carboxylic acid ester of a $C_1$–$C_6$ alkyl, a carboxylic acid ester of —$CH_2$—O—(C=O)—$R^{18}$; or $R^8$ in combination with $R^2$, or $R^9$ in combination with $R^3$, or both, form a saturated 5- or 6-membered ring that is optionally substituted by one or more methyls; or $R^8$ in combination with $R^9$ forms a saturated 5- or 6-membered heterocycle that is a piperidine, a morpholine, a pyrrolidine or a piperazine, each of which is optionally substituted by methyl, carboxylic acid, a salt of carboxylic acid, a carboxylic acid ester of a $C_1$–$C_6$ alkyl, or a carboxylic acid ester of —$CH_2$—O—(C=O)—$R^{18}$;

$R^{10}$ is F, carboxylic acid, a salt of carboxylic acid, a carboxylic acid ester of a $C_1$–$C_6$ alkyl, or a carboxylic acid ester of —$CH_2$—O—(C=O)—$R^{18}$; or $R_{10}$ is $C_1$–$C_{18}$ alkyl, alkenyl or alkynyl that is optionally substituted one or more times by F, Cl, Br, carboxylic acid, a salt of carboxylic acid, a carboxylic acid ester of a $C_1$–$C_6$ alkyl, a carboxylic acid ester of —$CH_2$—O—(C=O)—$R^{18}$, sulfonic acid, salt of sulfonic acid, amino, alkylamino, or dialkylamino, the alkyl groups of which have 1–6 carbons; or $R^{10}$ is —L—; or $R^{10}$ has the formula

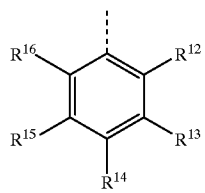

where $R^{12}$, $R^{13}$, $R^{14}$, $R^{15}$ and $R^{16}$ are independently H, F, Cl, Br, I; or sulfonic acid, salt of sulfonic acid, carboxylic acid, a salt of carboxylic acid, a carboxylic acid ester of a $C_1$–$C_6$ alkyl, a carboxylic acid ester of —$CH_2$—O—(C=O)—$R^{18}$, CN, nitro, hydroxy, azido, amino, hydrazino; or $C_1$–$C_{18}$ alkyl, $C_1$–$C_{18}$ alkoxy, $C_1$–$C_{18}$ alkylthio, $C_1$–$C_{18}$ alkylamino, $C_1$–$C_{18}$ alkylester, $C_1$–$C_{18}$ alkylamido or $C_1$–$C_{18}$ arylamido, the alkyl or aryl portions of which are optionally substituted one or more times by F, Cl, Br, I, hydroxy, carboxylic acid, a salt of carboxylic acid, a carboxylic acid ester of a $C_1$–$C_6$ alkyl, a carboxylic acid ester of —$CH_2$—O—(C=O)—$R^{18}$, sulfonic acid, salt of sulfonic acid, amino, alkylamino, dialkylamino or alkoxy, the alkyl portions of each having 1–6 carbons; or one pair of adjacent substituents $R^{13}$ and $R^{14}$, $R^{14}$ and $R^{15}$ or $R^{15}$ and $R^{16}$, when taken in combination, form a fused 6-membered aromatic ring that is optionally further substituted by carboxylic acid, a salt of carboxylic acid, a carboxylic acid ester of a $C_1$–$C_6$ alkyl, a carboxylic acid ester of —$CH_2$—O—(C=O)—$R^{18}$;

$R^{11}$ is H, hydroxy, CN or a $C_1$–$C_6$ alkoxy; or $R^{10}$ in combination with $R^{11}$ forms a 5-membered spirolactone ring or a 5-membered spirosultone ring; or $R^{11}$ in combination with $R^{12}$ forms a 5- or 6-membered spirolactone ring or a 5- or 6-membered spirosultone ring that is optionally and independently substituted by H, F or $CH_3$; or $R^{10}$ in combination with $R^{11}$ is a carbonyl oxygen;

provided that at least one of $R^1$, $R^2$, $R^3$, $R^4$, $R^5$, $R^6$, and $R^{10}$ is F, or at least three of $R^{12}$, $R^{13}$, $R^{14}$, $R^{15}$ and $R^{16}$ are F; and further provided that one of $R^2$, $R^3$, $R^4$, $R^5$, $R^7$, $R^8$, $R^9$, $R^{10}$, $R^{12}$, $R^{13}$, $R^{14}$, $R^{15}$ or $R^{16}$ on each dye is —L—; where each L is a single covalent bond, or L is a covalent linkage having 1–24 nonhydrogen atoms selected from the group consisting of C, N, O and S and is composed of any combination of single, double, triple or aromatic carbon-carbon bonds, carbon-nitrogen bonds, nitrogen-nitrogen bonds, carbon-oxygen bonds and carbon-sulfur bonds; and each —L— is bound to a $S_c$ that is a conjugated substance.

104. A compound, as claimed in claim 54, wherein $S_c$ is an ion-complexing moiety.

105. A compound, as claimed in claim 104, wherein the ion-complexing moiety is a BAPTA or APTRA or a phenanthroline.

106. A compound, as claimed in claim 105, wherein A is $OR^7$; $R^2$ and $R^5$ are each F; $R^{10}$ is —L—$S_c$; and the conjugated substance is an ion-complexing moiety that is a BAPTA.

107. A compound, as claimed in claim 106, wherein L is a single covalent bond.

* * * * *

UNITED STATES PATENT AND TRADEMARK OFFICE
CERTIFICATE OF CORRECTION

PATENT NO.    : 6,162,931
DATED         : December 19, 2000
INVENTOR(S)   : Gee et al.

It is certified that error appears in the above-identified patent and that said Letters Patent is hereby corrected as shown below:

<u>Column 23,</u>
Line 45, "(9B)" should read -- (9H) --.

<u>Column 28,</u>
Line 17, there is a line underneath "antigen" and "antibody" and there should not be a line.
Line 25, "apNA" should read -- "aDNA" --.
Line 41, "$H^{30}$" should read -- $H^+$ --.

<u>Column 29,</u>
Line 17, "undexpected" should read -- unexpected --.

<u>Column 45,</u>
Line 41, "(t, 13.0Hz)" should read -- (t, J=13.0Hz) --.

<u>Column 82,</u>
Line 46, "with $R^8$" should read -- with $R^3$ --.

<u>Column 88,</u>
Line 21, "claim 49" should read -- claim 46 --.

<u>Column 91,</u>
Line 4, "$R^6$" should read -- $R^{16}$ --.

<u>Column 95,</u>
Line 65, "1-carbons should read -- 1-6 carbons --.

UNITED STATES PATENT AND TRADEMARK OFFICE
CERTIFICATE OF CORRECTION

PATENT NO. : 6,162,931
DATED : December 19, 2000
INVENTOR(S) : Gee et al.

It is certified that error appears in the above-identified patent and that said Letters Patent is hereby corrected as shown below:

<u>Column 96,</u>
Line 6, "$C_1$-Cls alkoxy" should read -- $C_1$-$C_{18}$ alkoxy --.

Signed and Sealed this

Twenty-fourth Day of December, 2002

JAMES E. ROGAN
*Director of the United States Patent and Trademark Office*